United States Patent [19]
Kitada et al.

[11] Patent Number: 6,136,781
[45] Date of Patent: *Oct. 24, 2000

[54] LH-RH RECEPTOR ANTAGONISTS

[75] Inventors: Chieko Kitada, Osaka; Shuichi Furuya; Koichi Kato, both of Ibaraki, all of Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/656,244

[22] PCT Filed: Apr. 25, 1996

[86] PCT No.: PCT/JP96/01140

§ 371 Date: Jun. 6, 1996

§ 102(e) Date: Jun. 6, 1996

[87] PCT Pub. No.: WO96/34012

PCT Pub. Date: Oct. 31, 1996

[30] Foreign Application Priority Data

Apr. 28, 1995 [JP] Japan .................................. 7-106775
May 9, 1995 [JP] Japan .................................. 7-110933

[51] Int. Cl.$^7$ .................................................. A61K 38/12
[52] U.S. Cl. ................................ 514/9; 514/17; 530/317; 530/330; 424/64; 424/813; 424/814
[58] Field of Search ..................... 530/317, 330; 514/9, 17; 424/64, 813, 814

[56] References Cited

U.S. PATENT DOCUMENTS

| 4,508,711 | 4/1985 | Coy et al. ........................... 514/11 |
| 5,516,889 | 5/1996 | Hollenberg et al. ................... 530/317 |

FOREIGN PATENT DOCUMENTS

| 0190946 | 8/1986 | European Pat. Off. . |
| 0436189 | 7/1991 | European Pat. Off. . |
| 0 528 312 | 2/1993 | European Pat. Off. . |
| 0606881 | 7/1994 | European Pat. Off. . |
| 1606881 | 7/1994 | European Pat. Off. . |
| 3-94692 | 4/1991 | Japan . |
| 3-130299 | 6/1991 | Japan . |
| 5-59098 | 3/1993 | Japan . |
| 5-194589 | 8/1993 | Japan . |
| 6-192293 | 7/1994 | Japan . |

OTHER PUBLICATIONS

Kessler et al, Liebigs Ann. Chem, 1989 (3) pp. 269–294.
Ehrlich et al, Tetrahedron Lett. (1993) 34(30) p. 4781–4.
Etzkorn, et al, (1994) pp. 10412–10425, J. Am Chem Soc.
Ehrlich et al, Synthesis of Cyclic Peptides via Efficient New Coupling Reagents, *Tetrahedron Letters,* vol. 34, No. 30, pp. 4781–4784, 1993.
Aumailley et al., "Strong and selective inhibitors of cell adhesion to vitronectin and laminin fragment P1", FEBS LETTERS, vol. 291, No. 1, pp. 50–54, 1991.
"PEPTIDES, Structure and Function", Charles M. Deber, et al., Proceedings of the Ninth American Peptide Symposium, pp. 549–552, 1985.
"Bioactive Conformation of Luteinizing Hormone–Releasing Hormone: Evidence from a Conformationally Constrained Analog", Roger M. Freidinger, et al., SCIENCE, vol. 210, No. 4470, pp. 656–658, 1980.
"A potent cyclic hexapeptide analogue of somatostatin", Daniel F. Veber, et al, NATURE, vol. 292, 2 pp. 55–58, 1981.

*Primary Examiner*—F. T. Moezie
*Attorney, Agent, or Firm*—Wenderoth, Lind & Ponack, L.L.P.

[57] ABSTRACT

The LH-RH receptor antagonists containing cyclic pentapeptides or salts thereof and novel cyclic pentapeptide or salts thereof are provided.

The LH-RH receptor antagonists of the present invention are effective as medicines for preventing and curing sex hormone-dependent cancers (e.g., prostatic cancer, uterine cancer, mammary cancer, pituitary tumor, etc.), prostatomegaly, endometriosis, hysteromyoma, puberty precox, amenorrheal syndromes, multilocular ovarian syndromes, comedo, etc. and are also effective as pregnancy controlling agents (e.g., contraceptives, etc.) and menstrual cycle controlling agents. Moreover, these are also useful in the livestock industry for the control of the estrus of animals and also for the improvement in the quality of meat and for the control of the growth of animals, as well as in the marine products industry as spawning promoters for fishes.

19 Claims, No Drawings

LH-RH RECEPTOR ANTAGONISTS

This is a §371 national stage application of international application PCT/JP96/01140 filed Apr. 25, 1996.

BACKGROUND OF THE INVENTION

1. Field of the Invention

The present invention provides LH-RH receptor antagonists containing cyclic pentapeptides or salts thereof having an LH-RH receptor antagonistic effect and novel cyclic pentapeptides or salts thereof having an excellent LH-RH receptor antagonistic effect.

2. Description of Related Art

The secretion of anterior pituitary hormones is controlled by peripheral hormones to be secreted by the organs, which are targeted by the individual anterior pituitary hormones, and also by secretion-promoting or secretion-retarding hormones to be secreted by the hypothalamus which is the upper center of the anterior lobe of hypophysis (these hormones are hereinafter referred to as hypothalamus hormones). At present, the presence of nine hypothalamus hormones has been confirmed, which include, for example, thyrotropin releasing hormone (TRH) and gonadotropin releasing hormone (GnRH) [this is also referred to as luteinizing hormone releasing hormone (LH-RH)] (Irie, M. & Toyama, K., Physiology 2, Bunkodo Publishing, pp. 610–618, 1986). It is presumed that these hypothalamus hormones exhibit their hormone effects, etc. via the receptors which are considered to exist in the anterior lobe of hypophysis (ibid.), and the analysis of receptor genes specific to these, including those of human beings, is being promoted (Imura, H. et al.; Bases and Clinics of Receptors, Asakura Shoten Publishing, pp. 297–304, 1993). Therefore, antagonists and agonists which are specific and selective to these receptors shall control the action of hypothalamus hormones and control the secretion of anterior pituitary hormones. As a result, such antagonists and agonists are expected to be useful for prevention and curing of disorders dependent on such anterior pituitary hormones.

The repeated administration of leuprorelin acetate, a highly-active derivative of luteinizing hormone releasing hormone (hereinafter referred to as LH-RH) which is one of hypothalamus hormones (Fujino et al., Biochemical and Biophysical Research Communication, Vol. 60, pp. 406–413, 1975; Oliver, R. T. D., et al., Br. J. Cancer, Vol. 59, p. 823, 1989; and Toguchi, et al., J. Int. Med. Res., Vol. 18, pp. 35–41, 1990) lowers the release and production of luteinizing hormone at hypophysis, lowers the reactivity of testis and ovarium on luteinizing hormone and retards the secretion of testosterone and estrogen. Accordingly, it is known that leuprorelin acetate exhibits anti-tumoral activity against cancers dependent on such hormones, such as prostatic cancer, and it has been applied to clinical use. In addition, leuprorelin acetate has been widely applied to clinical use as a medicine for curing endometriosis, puberty precox, etc. It is presumed that the high carcinostatic activity of leuprorelin acetate will result from the fact that it is more resistant to proteases than natural LH-RH and the fact that it has high affinity with LH-RH receptors thereby causing the desensitization of the reactivity of LH-RH due to the decrease in the number of its receptors. However, since leuprorelin acetate is an super-agonist for LH-RH receptors, it is reported that the acetate causes transient exacerbation that is accompanied by the increase in the serum testosterone concentration, due to its pituitary-gonadotropic effect (acute effect), immediately after the first administration thereof.

Given the background situations as above, LH-RH antagonists are desired which have more excellent curing effect while not exhibiting the above-mentioned transient pituitary-gonadotropic effect (acute effect).

The various cyclic pentapeptides (FEBS LETTERS, vol. 291, No. 1, 50–54 (1991), Biochemical Society Transactions, Current Techniques in Polypeptide Structure and Synthesis, 1049–1052 (1994), U.S. Pat. No. 4,508,711, EP-A 436,189, EP-A 528,312, EP-A 606881, Japanese Patent Laid-Open No. 3-94692, 3-130299, 6-192293, 5-59098 and 5-194589) have been reported. However, they have not disclosed about LH-RH receptor antagonistic effect.

As compounds showing LH-RH antagonistic effect, linear peptides (U.S. Pat. Nos. 5,140,009 and 5,171,835), cyclic hexapeptide derivatives (Japanese Patent Laid-Open No. 61-191698, EP-A 0190946), bicyclic peptide derivatives (Journal of Medicinal Chemistry, Vol. 36, pp. 3265–3273, 1993), etc have been reported.

SUMMARY OF THE INVENTION

The present invention relates to LH-RH receptor antagonists containing cyclic pentapeptides or salts thereof having an excellent luteinizing hormone releasing hormone (LH-RH) receptor antagonistic effect and novel cyclic pentapeptide or salts thereof having an excellent LH-RH receptor antagonistic effect.

Considering the above-mentioned situations, the present inventors have diligently studied so as to obtain compounds usable in LH-RH antagonistic medicines and, as a result, found that cyclic pentapeptides of the following formula (I) or salts thereof show an excellent LH-RH antagonistic effect. On the basis of these findings, the present inventors have further studied and have accomplished the present invention.

Thus, the present invention relate to:

(1) A LH-RH receptor antagonistic composition comprising a cyclic pentapeptide of the formula (I):

$$\text{cyclo } (-A_1-A_2-A_3-A_4-A_5-) \tag{I}$$

wherein $A_1$, $A_2$, $A_3$, $A_4$ and $A_5$ independently represent an α-amino acid residue or a salt thereof (SEQ ID No. 1).

(2) The composition according to above (1), wherein $A_1$, $A_2$, $A_3$, $A_4$ and $A_5$ independently represent a group of the formula: —NH—CHX—CO—, in which X represents (1) —$(CH_2)_m$—R, wherein m represents an integer of from 0 to 10, and R represents a hydrogen atom, an optionally substituted hydroxyl group, an optionally substituted amino group, an optionally substituted mercapto group or an organic residue or (2) —$(CH_2)_n$—NH—C(=NH)—NH—R', wherein n represents an integer of from 1 to 10, and R', wherein represents a hydrogen atom, a nitro group or an optionally substituted benzenesulfonyl group.

(3) The composition according to above (2), wherein the organic residue of R is an optionally substituted alkyl group, an optionally substituted aryl group, an optionally substituted heterocyclic group, an acyl group, or an esterified or amidated carboxyl group.

(4) The composition according to above (2), wherein $A_1$ is a group of the formula: —NH—CHX$_1$—CO—, in which X$_1$ represents (1) —$(CH_2)_{m^1}$—R, wherein $m^1$ represents an integer of from 0 to 10, and R$_1$ represents a hydrogen atom, an optionally substituted amino group, an optionally substituted alkyl group, an optionally substituted aryl group or an optionally substituted heterocyclic group, or (2) —(CH$_2$)n$^1$—NH—C(=NH)—NH—R$_2$, wherein n$^1$ represents an integer of from 1 to 5, and R$_2$ represents a hydrogen atom, nitro or an optionally substituted benzenesulfonyl group.

(5) The composition according to above (1), wherein A$_1$ is an α-amino acid residue selected from the group consisting of Phe, Gly, Ala, Arg, Lys, Tyr, Leu and their derivatives.

(6) The composition according to above (1), wherein A$_1$ is an α-amino acid residue selected from the group consisting of Phe, (p-Cl)Phe, (p-F)Phe, Phg, Ala, Thg(2), Arg, Lys, Tyr, Leu, Arg(Tos) and Lys(Isopropyl).

(7) The composition according to above (2), wherein A$_2$ is a group of the formula: —NH—CHX$_2$—CO—, in which X$_2$ represents (1) —(CH$_2$)m$^2$—R$_3$, wherein m$^2$ represents an integer of from 0 to 10, and R$_3$ represents an optionally substituted amino group, an optionally substituted heterocyclic group, or an acyl group, or (2) —(CH$_2$)n$^2$—NH—C(=NH)—NH—R$_4$, wherein n$^2$ represents an integer of from 1 to 5, and R$_4$ represents a hydrogen atom, nitro or an optionally substituted benzenesulfonyl group.

(8) The composition according to above (1), wherein A$_2$ is an α-amino acid residue selected from the group consisting of Arg, Lys, Trp, Glu and their derivatives.

(9) The composition according to above (1), wherein A$_2$ is an α-amino acid residue selected from the group consisting of Arg, Arg(Mtr), Arg(Tos), Lys, Lys(SO$_2$Nap(1)), Lys(SO$_2$Nap(2)), Lys(COPh), Lys(COCH$_2$Ph), Trp, Glu, Glu(NH—CH$_2$CH$_2$-Ph), Glu(NH—CH$_2$-Ph), Glu(NH—CH-Ph$_2$), Glu(NH—CH$_2$-Nap(1)), Glu(Php), Glu(Bzlp), Glu((2)-Pyp), Glu(2-MeOPhp), Glu(4-MeOPhp), Lys(CO—(CH$_2$)$_3$-Ph), Lys(CO—(CH$_2$)$_5$-Ph) and Lys(Ac).

(10) The composition according to above (2), wherein A$_3$ is a group of the formula —NH—CHX$_3$—CO—, in which X$_3$ represents —(CH$_2$)m$^3$—R$_8$, wherein m$^3$ represents an integer of from 0 to 10, and R$_8$ represents an optionally substituted aryl group, an optionally substituted amino group, an optionally substituted heterocyclic group, or an acyl group.

(11) The composition according to above (1), wherein A$_3$ is an α-amino acid residue selected from the group consisting of Phe, Ala, Tyr, Lys, Asp, Trp and their derivatives.

(12) The composition according to above (1), wherein A$_3$ is an α-amino acid residue selected from the group consisting of Phe, Nal, (p-Cl)Phe, (p-F)Phe, Tyr, Lys(CO-Ph), Lys(CO-Nap(1)), Asp(NH—CH$_2$-Ph), Trp and Lys(SO$_2$Nap(1)).

(13) The composition according to above (2), wherein A$_4$ is a group of the formula: —NH—CHX$_4$—CO—, in which X$_4$ represents (1) —(CH$_2$)m$^4$—R$_{11}$, wherein m$^4$ represents an integer of from 0 to 10, and R$_{11}$ represents a hydrogen atom, an optionally substituted hydroxyl group, an optionally substituted amino group, an optionally substituted alkyl group, an optionally substituted aryl group, or an optionally substituted heterocyclic group, or (2) —(CH$_2$)n$^4$—NH—C(=NH)—NH—R$_{12}$, wherein n$^4$ represents an integer of from 1 to 5, and R$_{12}$ represents a hydrogen atom, nitro or an optionally substituted benzenesulfonyl group.

(14) The composition according to above (1), wherein A$_4$ is an α-amino acid residue selected from the group consisting of Ala, Leu, Phe, Trp, Ser, Arg, Lys, Tyr and their derivatives.

(15) The composition according to above (1), wherein A$_4$ is an α-amino acid residue selected from the group consisting of Ala, Leu, Phe, Trp, Ser, Arg, Lys(Nic) and Tyr.

(16) The composition according to above (2), wherein A$_5$ is a group of the formula: —NH—CHX$_5$—CO—, in which X$_5$ represents —(CH$_2$)m$^5$—R$_{14}$, wherein m$^5$ represents an integer of from 0 to 10, and R$_{14}$ represents an optionally substituted aryl group, an optionally substituted heterocyclic group, an optionally substituted alkyl group, or an optionally substituted amino group.

(17) The composition according to above (1), wherein A$_5$ is an α-amino acid residue selected from the group consisting of Trp, Phe, Leu, Lys and their derivatives.

(18) The composition according to above (1), wherein A$_5$ is an α-amino acid residue selected from the group consisting of Trp, Phe, Leu and Lys(SO$_2$Nap(1)).

(19) The composition according to above (1), wherein the α-amino acid residue is of a L- or D-configuration.

(20) The composition according to above (1), wherein A$_1$, A$_3$ and A$_5$ independently represent an L-configuration, and A$_4$ is of a D-configuration.

(21) The composition according to above (1), wherein A$_1$, A$_3$ and A$_5$ independently represent a D-configuration, and A$_4$ is of a L-configuration.

(22) The composition according to above (1), which is medicament for preventing treating sex hormone-dependent disorders.

(23) The composition according to above (22), wherein the sex hormone-dependent disorders are sex hormone-dependent cancers.

(24) The composition according to above (23), wherein the sex hormone-dependent cancers are prostatic cancer, uterine cancer, mammary cancer or pituitary tumor.

(25) The composition according to above (22), wherein the sex hormone-dependent disorders are prostatomegaly, endometriosis, hysteromyoma or puberty precox.

(26) The composition according to above (22), which is a pregnancy controlling agent.

(27) The composition according to above (22), which is a menstrual cycle controlling agent.

(28) The pregnancy controlling agent according to above (26), which is for contraception.

(29) A cyclic pentapeptide of the formula (II):

$$\text{cyclo(-A}_1\text{'-A}_2\text{'-A}_3\text{'-A}_4\text{'-A}_5\text{'-)} \qquad (II)$$

wherein A$_1$' represents Arg or derivatives thereof, and A$_2$', A$_3$', A$_4$' and A$_5$' independently represents an amino acid residue except Gly, Pro and an acidic amino acid residue, or a salt thereof.

(30) The cyclic pentapeptide according to above (29), wherein the compound of the formula (II) contains at least Arg, Lys, Trp and Leu, in which Arg, Lys, Trp or Leu may be its derivatives.

(31) The cyclic pentapeptide according to above (29), wherein the compound of the formula (II) contains at least Arg, Phe and ala, in which Arg, Phe or Ala may be its derivatives.

(32) The cyclic pentapeptide according to above (29), wherein the derivatives of Arg is Arg(Mtr) or Arg(Tos).

(33) The cyclic pentapeptide according to above (29), wherein any one of $A_2'$-$A_3'$, $A_3'$-$A_4'$ and $A_4'$-$A_5'$ is Trp-Leu or Ala-Trp.

(34) The cyclic pentapeptide according to above (29), wherein $A_1'$, $A_2'$, $A_3'$, $A_4'$ and $A_5'$ independently are of L- or D-configuration.

(35) The cyclic pentapeptide according to above (29), wherein $A_1'$ and $A_3'$ are of L-configuration, and $A_2'$ and $A_4'$ are of D-configuration.

(36) The cyclic pentapeptide according to above (29), wherein $A_1'$, $A_4'$ and $A_5'$ are of L-configuration, and $A_3'$ is of D-configuration.

(37) A cyclic pentapeptide or a salt thereof according to above (29), which comprises Arg, Lys, Tyr, Trp and Leu, wherein Arg, Lys, Tyr, Trp or Leu may be its derivatives.

(38) A cyclic pentapeptide or a salt thereof according to above (29), which comprise Arg, Glu, Lys, Trp and Leu, wherein Arg, Glu, Lys, Trp or Leu may be its derivatives.

(39) A cyclic pentapeptide or a salt thereof according to above (29), which comprise Gly, Arg, Phe, Ala and Trp, wherein Gly, Arg, Phe, Ala or Trp may be its derivatives.

(40) A cyclic pentapeptide or a salt thereof according to above (29), which comprise Ala, Arg, Phe, Ala and Trp, wherein Ala, Arg, Phe, Ala or Trp may be its derivatives.

(41) A cyclic pentapeptide or a salt thereof according to above (29), which comprise Gly, Arg, Phe, Ala and Phe, wherein Gly, Arg, Phe, Ala or Phe may be its derivatives.

(42) A cyclic pentapeptide or a salt thereof according to above (29), which comprises Arg, Phe, Phe, Trp and Ala, wherein Arg, Phe, Phe, Trp or Ala may be its derivatives.

(43) A cyclic pentapeptide or a salt thereof according to above (29), which is a cyclo(-Arg-D-Lys(COCH$_2$CH$_2$CH$_2$CH$_2$Ph)-Tyr-D-Trp-Leu-), a cyclo(-Arg-D-Glu(NHCH$_2$CH$_2$Ph)-Lys(CONap(1))-D-Trp-Leu-), a cyclo(-Phg-D-Arg(Tos)-Phe-D-Ala-Trp-), a cyclo(-Ala-D-Arg(Tos)-Phe-D-Ala-Trp-), A cyclo(-Phg-D-Arg(Tos)-Phe-D-Ala-Phe-) or a cyclo(-Phg-D-Arg-Phe-D-Ala-Trp-).

(44) A method for antagonizing LH-RH in a mammal in need thereof comprising administering an effective amount of the cyclic pentapeptide of the formula:

$$\text{cyclo}(-A_1-A_2-A_3-A_4-A_5-) \quad (I)$$

wherein $A_1$, $A_2$, $A_3$, $A_4$ and $A_5$ independently represent an α-amino acid residue, or a salt thereof, for the mammal suffering from a LH-RH derived disorder.

(45) Use of a cyclic pentapeptide of the formula (I):

$$\text{cyclo}(-A_1-A_2-A_3-A_4-A_5-) \quad (I)$$

wherein $A_1$, $A_2$, $A_3$, $A_4$ and $A_5$ independently represent an α-amino acid residue, or a salt thereof, for the manufacture of a LH-RH receptor antagonistic composition.

(46) Use of a cyclic pentapeptide of the formula (I):

$$\text{cyclo}(-A_1-A_2-A_3-A_4-A_5-) \quad (I)$$

wherein $A_1$, $A_2$, $A_3$, $A_4$ and $A_5$ independently represent an α-amino acid residue, or a salt thereof, for the manufacture of a medicament for preventing or treating sex hormone-dependent disorders.

DETAILED DESCRIPTION OF THE PREFERRED EMBODIMENT(S)

Specifically, the present invention relates to LH-RH receptor antagonists containing cyclic pentapeptides of the formula (I):

$$\text{cyclo}(-A_1-A_2-A_3-A_4-A_5-) \quad (I)$$

wherein $A_1$, $A_2$, $A_3$, $A_4$ and $A_5$ represent, independently, an α-amino acid residue, or salts thereof.

$A_1$, $A_2$, $A_3$, $A_4$, and $A_5$ represent, independently, an α-amino acid residue of —NH—CHX—CO—, in which X is preferably a group of —(CH$_2$)$_m$—R (where m represents an integer of from 0 to 10, and R represents a hydrogen atom an optionally substituted hydroxyl group, an optionally substituted amino group, an optionally substituted mercepto group or an organic residue) or —(CH$_2$)$_n$—NH—C(=NH)—NH—R' (where n represents an integer of from 1 to 10, and R' represents a hydrogen atom, nitro group or an optionally substituted benzenesulfonyl group.

Referring to R and R', the substituted hydroxyl groups of R include (1) acyloxy groups, such as C$_{1-6}$ alkanoyloxy (for example, formyloxy, acetates or propionates), C$_{4-9}$ alicyclic carbonyloxy (for example, cyclopentanecarbonyloxy or cyclohexanecarbonyloxy), C$_{7-15}$ arylcarbonyloxy or (for example, benzoyloxy and 4-methylbenzoyloxy), C$_{8-18}$ aralkylcarbonyloxy (for example, phenylacetoxy, 2-phenylpropionyloxy, 3-phenylpropionyloxy or diphenylacetoxy), aromatic heterocycle-alkylcarbonyloxy (for example, indole-2-ylacetoxy or indole-3-ylacetoxy); (2) C$_{1-6}$ alkoxy (for example, methyl ether, ethyl ether, n-propyl ether or t-butyl ether); (3) C$_{3-8}$ cycloalkoxy (for example, cyclopentyloxy or cyclohexyloxy); (4) C$_{6-14}$ aryloxy (for example, phenyloxy or 4-methylphenyloxy); and (5) C$_{7-15}$ aralkyloxy (for example, benzyloxy, phenethyloxy or diphenylmethyloxy).

The substituted amino group of R may be any one of mono-substituted amino groups and di-substituted amino groups.

The substituted amino groups include mono- or di-C$_{1-6}$ alkylamino (for example, methylamino, dimethylamino, ethylamino, diethylamino, N-methyl-N-ethylamino, n-propylamino, iso-propylamino, t-butylamino or, N-ethyl-N-t-butylamino), C$_{3-8}$ cycloalkylamino (for example, N-cyclopentylamino or N-cyclohexylamino), C$_{6-14}$ arylamino (for example, N-phenylamino or N-(4-methylphenyl)amino, N-1-naphthylamino, N-2-naphthylamino), C$_{7-15}$ aralkylamino (for example, N-benzylamino, N-phenethyl-amino, N-(4-chlorobenzyl) amino, N-(2-methylbenzyl)amino, N-(3-methylbenzyl) amino, N-(4-methylbenzyl)amino, N-(2-methoxybenzyl) amino, N-(3-methoxybenzyl)amino or N-(4-methoxybenzyl)amino), N-C$_{1-6}$ alkyl-N-C$_{6-14}$ arylamino (for example, N-methyl-N-phenylamino), aromatic heterocycle-C$_{1-6}$ alkylamino (for example, 2-furylmethylamino, 3-furylmethylamino, 2-thienylmethylamino, 3-thienylmethylamino, indole-2- ylmethylamino or indole-3-ylmethylamino), —NHSO$_2$Y, wherein Y is an optionally substituted aromatic group, and acylamino group of NH—CO—(CH$_2$)n$^5$—R$_{15}$, wherein n$^5$ is an integer of from 0 to 10, R$_{15}$ is an optionally substituted aryl group, an alkyl group, or an optionally substituted heterocyclic group.

The above-mentioned aromatic group of Y is preferably an aromatic hydrocarbon group. The aromatic hydrocarbon group preferably has from 6 to 14 carbon atoms and preferably includes phenyl and naphthyl. The aromatic group may optionally be substituted by from 1 to 3 substituents. The substituents are for example, a halogen atom (e.g., fluorine, chlorine, bromine), a hydroxyl group, a C$_{1-6}$ alkyl group (e.g., methyl, ethyl), a C$_{1-6}$ alkoxy group (e.g., methoxy, ethoxy or hexyloxy), a carboxyl group or a C$_{1-6}$ alkylcarbonyl group (e.g., formyl, acetyl or hexanoyl).

The aryl group of the optionally substituted aryl group represented by R$_{15}$ has from 6 to 14 carbon atoms and preferably includes phenyl and naphthyl. The aryl group may optionally be substituted by from 1 to 3 substituents. The substituents are, for example, a halogen atom (e.g., fluorine, chlorine, bromine), a hydroxyl group, a C$_{1-6}$ alkyl group (e.g., methyl, ethyl), a C$_{1-6}$ alkoxy group (e.g., methoxy, ethoxy), a carboxyl group, a C$_{1-6}$ alkylcarbonyl group (e.g., formyl, acetyl).

The alkyl group represented by R$_{15}$ is a C$_{1-6}$ alkyl group, such as methyl, ethyl, n-propyl, iso-propyl, n-butyl, iso-butyl, (1-methyl)propyl, tert-butyl, n-pentyl, (2-methyl)butyl, (3-methyl)butyl, neopentyl, n-hexyl, (2,2-dimethyl)butyl or (3,3-dimethyl)butyl groups.

The heterocyclic group of the optionally substituted heterocyclic group represented by R$_{15}$ is preferably a 5- or 6-membered heterocyclic group having from 1 to 4 hetero atoms, such as oxygen, sulfur and/or nitrogen (e.g., pyrrolyl, pyrrolinyl, pyrrolidinyl, imidazolyl, imidazolidiyl, piperidinyl, pyrazolyl, pyrazolidinyl, pyridyl, pyrimidyl, pyrazinyl, piperazinyl, pyridazinyl, triazolyl, tetrazolyl, dihydrotriazinyl, pyridyl, oxazolyl, isoxazilyl, oxadiazolyl, morpholinyl, furyl, thienyl, thiazolyl, isothiazolyl, thiazolinyl, thiadiazolyl or triazolidinyl), or a condensed heterocyclic group where any one of these groups is condensed with other ring(s) such as benzene ring(s), etc. (e.g., indolyl, isoindolyl, indolidinyl, benzimidazolyl, quinolyl, isoquinolyl, indazolyl, benzotriazolyl, tetrazolopyridyl, tetrazolopyridazinyl, benzoxazolyl, benzoxadiazolyl, benzothiazolyl or benzothiadiazolyl). These heterocyclic groups may optionally have 1 to 3 substituents on the carbon and/or nitrogen atom(s). The substituents on the carbon atom include a C$_{1-6}$ alkyl group (e.g., methyl, ethyl, n-propyl or n-butyl), a halogen atom (e.g., fluorine, chlorine, bromine or iodine), a hydroxyl group, a carboxyl group, a C$_{1-6}$ alkoxy group (e.g., methoxy, ethoxy, n-propoxy or n-butoxy), a C$_{1-6}$ alkanoyl group (e.g., formyl or acetyl). The substituents on the nitrogen atom include a C$_{1-6}$ alkyl group (e.g., methyl, ethyl, n-propyl or n-butyl), a C$_{1-6}$ alkylcarbonyl group (e.g., formyl, acetyl, etc.), a hydroxy-C$_{1-6}$ alkyl group (e.g., hydroxymethyl or 2-hydroxyethyl).

The substituted mercapto groups of R include (1) acylthio groups such as C$_{1-6}$ alkanoylthio (for example, formylthio, acetylthio or propionylthio), C$_{4-9}$ alicyclic carbonylthio (for example, cyclopentanecarbonylthio or cyclohexanecarbonylthio), C$_{7-15}$ arylcarbonylthio (for example, benzoylthio or 4-methylbenzoylthio) and C$_{8-16}$ aralkylcarbonylthio (for example, phenylacetylthio, 2-phenylpropionylthio, 3-phenylpropionylthio or diphenylacetylthio); (2) C$_{1-6}$ alkylthio (for example, methylthio, ethylthio, n-propylthio or t-butylthio); (3) C$_{3-8}$ cycloalkylthio (for example, cyclopentylthio or cyclohexylthio); (4) C$_{6-12}$ arylthio (for example, phenylthio or 4-methylphenylthio); and (5) C$_{7-15}$ aralkylthio (for example, benzylthio, phenethylthio or diphenylmethylthio).

The organic residue of R may be any one of substituents which contain carbon atom in the molecule and which have a chemical bond on the carbon atom. Especially preferred is optionally substituted alkyl group, optionally substituted aryl group, optionally substituted heterocyclic group, acyl group, or esterified or amidated carboxyl group.

The alkyl group of the optionally substituted alkyl group of R is preferably a C$_{1-6}$ alkyl group, which includes methyl, ethyl, n-propyl, iso-propyl, n-butyl, iso-butyl, (1-methyl)propyl, tert-butyl, n-pentyl, (2-methyl)butyl, (3-methyl)butyl, neopentyl, n-hexyl, (2,2-dimethyl)butyl and (3,3-dimethyl)butyl groups. The substituents for the alkyl group include a hydroxyl group, an amino group, a carboxyl group, a C$_{1-6}$ alkylamino group (e.g., methylamino, ethylamino), a C$_{1-6}$ alkoxy group (e.g., methoxy, ethoxy), and a halogen atom (e.g., fluorine, chlorine or bromine).

The aryl group of the optionally substituted aryl group of R has from 6 to 14 carbon atoms and preferably is phenyl and naphthyl. The aryl group may optionally be substituted by from 1 to 3 substituents. The substituents are, for example, a halogen atom (e.g., fluorine, chlorine or bromine), a hydroxyl group, a C$_{1-6}$ alkyl group (e.g., methyl, ethyl), a C$_{1-6}$ alkoxy group (e.g., methoxy, ethoxy), a carboxyl group, a C$_{1-6}$ alkylcarbonyl group (e.g., formyl, acetyl) and a C$_{1-6}$ alkoxycarbonyl group (e.g., acetoxy).

The heterocyclic group of the optionally substituted heterocyclic group of R is preferably a or 6-membered heterocyclic group having from 1 to 4 hetero atoms of O, S and/or N. (e.g., pyrrolyl, pyrrolinyl, pyrrolidinyl, imidazolyl, imidazolidiyl, piperidinyl, pyrazolyl, pyrazolidinyl, pyridyl, pyrimidyl, pyrazinyl, piperazinyl, pyridazinyl, triazolyl, tetrazolyl, dihydrotriazinyl, pyridyl, oxazolyl, isoxazolyl, oxadiazolyl, morpholinyl, furyl, thienyl, thiazolyl, isothiazolyl, thiazolinyl, thiadiazolyl or triazolidinyl), or a condensed heterocyclic group where any one of these groups is condensed with other ring(s) such as benzene ring(s), etc. (e.g., indolyl, isoindolyl, indolidinyl, benzimidazolyl, quinolyl, isoquinolyl, indazolyl, benzotriazolyl, tetrazolopyridyl, tetrazolopyridazinyl, benzoxazolyl, benzoxadiazolyl or benzothiazolyl, benzothiadiazolyl). These heterocyclic groups may optionally have from 1 to 3 substituents on the carbon and/or nitrogen atom(s). The substituents on the carbon atom include a C$_{1-6}$ alkyl group (e.g., methyl, ethyl, n-propyl or n-butyl), a halogen atom (e.g., fluorine, chlorine, bromine or iodine), a hydroxyl group, a carboxyl group, a C$_{1-6}$ alkoxy group (e.g., methoxy, ethoxy, n-propoxy or n-butoxy), a C$_{1-6}$ alkylcarbonyl group (e.g., formyl, acetyl), etc. The substituents on the nitrogen atom include a C$_{1-6}$ alkyl group (e.g., methyl, ethyl, n-propyl or n-butyl), a C$_{1-6}$ alkylcarbonyl group (e.g., formyl or acetyl) and a hydroxy-C$_{1-6}$ alkyl group (e.g., hydroxymethyl or 2-hydroxyethyl).

The acyl group of R include an acyl group derived from organic acid, includes an acyl group derived from organic carboxylic acid, organic sulfonic acid, organic phosphoric acid. Preferred is a C$_{1-13}$ acyl (for example, a C$_{1-10}$ alkanoyl group (e.g., formyl, acetyl, propionyl or butylyl, etc.), a C$_{3-10}$ alkenoyl group (e.g., propenoyl, 2-butenoyl, 3-propenoyl, etc.), a C$_{3-10}$ alkynoyl group (e.g., propynoyl, 2-butynoyl or 3-butynoyl), a C$_{7-13}$ aroyl group (e.g., benzoyl, 1-naphthalenecarbonyl or 2-naphthalenecarbonyl), or acyl group to be represented by —CO—R$_5$ mentioned hereinafter.

The amidate carboxyl group of the carboxyl groups includes carbamoyl (—CONH$_2$), N-C$_{1-6}$ alkylcarbamoyl (for example, N-methylcarbamoyl, N-ethylcarbamoyl, N-(n-propyl)carbamoyl and N-t-butylcarbamoyl), N-C$_{3-8}$ cycloalkylcarbamoyl (for example, N-cyclopentylcarbamoyl and N-cyclohexylcarbamoyl), N-C$_{6-12}$ arylcarbamoyl (for example, N-phenylcarbamoyl and N-(4-methylphenyl)carbamoyl), N-C$_{7-15}$ aralkylcarbamoyl (for example, N-benzylcarbamoyl, N-phenethylcarbamoyl, N-(1,2-diphenylethyl)carbamoyl), N-(aromatic heterocycle-C$_{1-6}$ alkyl)carbamoyl (for example, N-[2-(indole-2-yl)ethyl]carbamoyl and N-[2-(indole-3-yl)ethyl]carbamoyl), piperidinecarbamoyl, piperazinecarbamoyl, N$^4$—C$_{1-6}$ alkylpiperazinecarbamoyl (for example, N$^4$-methylpiperazinecarbamoyl and N$^4$-ethylpiperazinecarbamoyl), N$^4$—C$_{3-8}$ cycloalkylpiperazinecarbamoyl (for example, N$^4$-cyclopentylpiperazinecarbamoyl and N$^4$-cyclohexylpiperazinecarbamoyl), N$^4$-(5 to 7 membered heterocyclicpiperazinecarbamoyl (for example N$^4$-pyridylpiperazinecarbamoyl, N$^4$-furylpiperazinecarbamoyl, N$^4$-thienylpiperazinecarbamoyl), N$^4$-C$_{6-12}$ arylpiperazinecarbamoyl (for example, N$^4$-phenylpiperazinecarbamoyl and N$^4$-(4-methylphenyl)piperazinecarbamoyl), N$^4$-C$_{7-15}$ aralkylpiperazinecarbamoyl (for example, N$^4$-benzylpiperazinecarbamoyl, N$^4$-pheneylpiperazinecarbamoyl, N$^4$-(1,2-diphenylethyl) piperazinecarbamoyl), N$^4$-(aromatic heterocycle-C$_{1-6}$ alkyl) piperazinecarbamoyl (for example, N$^4$-[2-(indole-2-yl) ethyl]piperazinecarbamoyl and N$^4$-[2-(indole- 3-yl)ethyl] piperazinecarbamoyl), N$^4$-C$_{1-6}$ aliphatic acylpiperazinecarbamoyl (for example, N$^4$-acetylpiperazinecarbamoyl and N$^4$-propionylpiperazinecarbamoyl), N$^4$—C$_{4-9}$ alicyclic acylpiperazinecarbamoyl (for example, N$^4$-cyclopentanecarbonylpiperazinecarbamoyl and N$^4$-cyclohexanecarbonylpiperazinecarbamoyl), N$^4$—C$_{7-15}$ arylacylpiperazinecarbamoyl (for example, N$^4$-benzoylpiperazinecarbamoyl and N$^4$-(4-methylbenzoyl) piperazinecarbamoyl), N$^4$—C$_{8-16}$ aralkylacylpiperazinecarbamoyl (for example, N$^4$-phenylacetylpiperazinecarbamoyl, N$^4$-(2-phenylpropion)piperazinecarbamoyl, N$^4$-(3-phenylpropionyl)piperazinecarbamoyl, N$^4$-diphenylacetylpiperazinecarbamoyl), N$^4$-(1-naphthylacetyl)piperazinecarbamoyl and N$^4$-(2-naphthylacetyl)piperazinecarbamoyl), N$^4$-(aromatic heterocycle-carbonyl)piperazinecarbamoyl (for example, N$^4$-(indole-2-ylcarbonyl)piperazinecarbamoyl and N$^4$-(indole-3-ylcarbonyl)piperazinecarbamoyl), and N$^4$-(aromatic heterocyclic-alkylcarbonyl)piperazinecarbamoyl (for example, N$^4$-(indole-2-ylacetyl)piperazinecarbamoyl and N$^4$-(indole-3-ylacetyl)-piperazinecarbamoyl).

The esterified carboxyl C$_{1-6}$ alkoxycarbonyl (for example, methoxycarbonyl, ethoxycarbonyl, n-propoxycarbonyl), C$_{3-8}$ cycloalkoxycarbonyl (for example, cyclopentyloxycarbonyl or cyclohexyloxycarbonyl) and C$_{7-15}$ aralkyloxycarbonyl (for example, benzyloxycarbonyl, phenetyloxycarbonyl, 1-phenylethyloxycarbonyl or diphenylmethyloxycarbonyl). The above-mentioned amidated carboxyl group forms also include amido groups with α-amino acids and amido groups with oligopeptides (for example, dipeptides, tripeptides and tetrapeptides).

The substituent(s) of the optionally substituted benzenesulfonyl group of R' may be positioned at any substitutable position(s) on the benzene ring. The substituents include, for example, a halogen atom (e.g., fluorine, chlorine or bromine), a C$_{1-8}$ alkyl group (e.g., methyl, ethyl, propyl, isopropyl or neopentyl) optionally substituted by 1 to 3 halogen atoms (e.g., fluorine, chlorine or bromine), a C$_{1-8}$ alkoxy group (e.g., methoxy, ethoxy, propoxy, isopropoxy, butoxy or isobutoxy) optionally substituted by 1 to 3 halogen atoms (e.g., fluorine, chlorine or bromine), an optionally halogenated alkylthio group having 1 to 8 carbon atoms (e.g., methylthio, ethylthio, propylthio, isopropylthio, butylthio, isobutylthio, sec-butylthio, tert-butylthio, pentylthio, isopentylthio or neopentylthio) optionally substituted by 1 to 3 halogen atoms (e.g., fluorine, chlorine, bromine), a C$_{1-6}$ acyloxy group (e.g., formyloxy, acetoxy, propionyloxy, etc.) and a hydroxyl group. Especially preferred is C$_{1-8}$ alkyl group or C$_{1-8}$ alkoxy group. The benzenesulfonyl group may be substituted by from 1 to 5 substituents as defined above. When the group is substituted by two or more substituents, the plural substituents may be the same or different.

The preferable example of the optionally substituted benzenesulfonyl group include tosyl, p-methoxybenzenesulfonyl, pentamethylbenzenesulfonyl and 4-methoxy-2,3,6-trimethylbenzenesulfonyl.

The α-amino acid residue represented by A$_1$ in the formula (I) is preferably represented by —NH—CHX$_1$—CO—.

Herein, X$_1$ is preferably a group of (1) —(CH$_2$)m$^1$—R$_1$, wherein m$^1$ represents an integer of from 0 to 10; and R$_1$ is preferably a hydrogen atom, an optionally substituted amino group, an optionally substituted alkyl group, an optionally substituted aryl group, or an optionally substituted heterocyclic group, or (2) —(CH$_2$)n$^1$—NH—C(=NH)—NH—R$_2$, wherein n$^1$ represents an integer of from 1 to 5; and R$_2$ is a hydrogen atom, nitro or an optionally substituted benzenesulfonyl group. m$^1$ is an integer of from 0 to 10, preferably an integer of from 0 to 5. n$^1$ is an integer of from 1 to 5 and preferably is 3.

The substituted amino group of the optionally substituted amino group represented by R$_1$ has the same meaning as defined in the substituted amino groups of R. The substituted amino group are preferably mono- or di-C$_{1-6}$ alkylamino such as methylamino, dimethylamino, ethylamino, diethylamino, N-methyl-N-ethylamino, n-propylamino, iso-propylamino, n-butylamino, iso-butylamino, (1-methyl) propylamino, tert-butylamino, N-ethyl-N-t-butylamino, n-pentylamino, (2-methyl)butylamino, (3-methyl) butylamino, neopentylamino, n-hexylamino, (2,2-dimethyl) butylamino or (3,3-dimethyl)butylamino. Of the optionally substituted amino groups mentioned above, especially preferred are amino and iso-propylamino.

The optionally substituted alkyl group represented by R$_1$ has the same meaning as defined in the optionally substituted alkyl group of R. Especially preferred is an iso-propyl group.

The aryl group in the optionally substituted aryl group represented by R$_1$ has the same meaning as defined in the aryl of R. The substituents of the aryl group of R$_1$ is preferably a halogen atom or a hydroxyl group. Examples of the optionally substituted aryl group include phenyl, 4-fluorophenyl, 4-chlorophenyl, 4-bromophenyl, 4-hydroxyphenyl, 4-methoxyphenyl, 4-methylphenyl, 1-naphthyl and 2-naphthyl groups, etc. Preferred are phenyl, 4-fluorophenyl, 4-chlorophenyl and 4-hydroxyphenyl groups.

The optionally substituted heterocyclic group represented by R$_1$ has the same meaning as defined in the optionally substituted heterocyclic group of R. Especially preferred is a thienyl group.

$R_2$ has the same meaning as defined in R'. $R_2$ is especially preferably a hydrogen atom or a p-toluenesulfonyl group (tosyl group).

$A_1$ is preferably an α-amino acid residue selected from Phe, Gly, Ala, Arg, Lys, Tyr, Leu or their derivatives. More concretely, $A_1$ is preferably an α-amino acid residue selected from Phe, (p-Cl)Phe, (p-F)Phe, Phg, Ala, Thg(2), Arg, Lys, Tyr, Leu, Arg(Tos), Lys(Isopropyl).

The α-amino acid residue represented by $A_2$ in the formula (I) is preferably represented by —NH—CHX$_2$—CO—.

Herein, $X_2$ is preferably (1) —(CH$_2$)m$^2$—R$_3$, wherein m$^2$ represents an integer of from 0 to 10; and $R_3$ is preferably an optionally substituted amino group, an optionally substituted heterocyclic group, or an acyl group (—CO—R$_5$), or (2) —(CH$_2$)n$^2$—NH—C(=NH)—NH—R$_4$, wherein n$^2$ represents an integer of from 1 to 5; and $R_4$ is a hydrogen atom, nitro or an optionally substituted benzenesulfonyl group. m$^2$ is an integer of from 0 to 10, preferably an integer of from 0 to 5. n$^2$ is an integer of from 1 to 5 and preferably is 3.

The substituted amino group of the optionally substituted amino group represented by $R_3$ may be any one of mono-substituted amino groups and di-substituted amino groups. The substituted amino groups include mono- or di-$C_{1-6}$ alkylamino (for example, methylamino, dimethylamino, ethylamino, diethylamino, N-methyl-N-ethylamino and t-butylamino, N-ethyl-N-t-butylamino), $C_{3-8}$ cycloalkylamino (for example, N-cyclopentylamino or N-cyclohexylamino, $C_{6-14}$ arylamino (for example, N-phenylamino or N-(4-methylphenyl)amino, N-1-naphthylamino, N-2-naphthylamino), $C_{7-20}$ aralkylamino (for example, N-benzylamino, N-phenethyl-amino, N-(4-chlorobenzyl)amino, N-(2-methylbenzyl)amino, N-(3-methylbenzyl)amino, N-(4-methylbenzyl)amino, N-(2-methoxybenzyl)amino, N-(3-methoxybenzyl)amino or N-(4-methoxybenzyl)amino, N-$C_{1-6}$ alkyl-N-$C_{6-14}$ arylamino (for example, N-methyl-N-phenylamino), aromatic heterocycle-$C_{1-6}$ alkylamino (for example, 2-furylmethylamino, 3-furyl-methylamino, 2-thienylmethylamino, 3-thienylmethylamino, indole-2-ylmethylamino and indole-3-ylmethylamino), acylamino group of —NH—CO—(CH$_2$)n$^3$—R$_7$, or —NHSO$_2$Y$_1$, wherein $Y_1$ is an optionally substituted aromatic group. Preferably are —NH—CO—(CH$_2$)n$^3$—R$_7$ or —NHSO$_2$Y$_1$.

n$^3$ represents 0 or an integer of 1 or more, preferably 0 or an integer of from 1 to 10, more preferably 0 or an integer of from 1 to 7.

$R_7$ is preferably an optionally substituted aromatic group or an alkyl group.

The aromatic group of the optionally substituted aromatic group represented by $R_7$ is preferably an aromatic hydrocarbon group. The aromatic hydrocarbon group has from 6 to 14 carbon atoms and is preferably phenyl or naphthyl. The aromatic group may optionally be substituted by from 1 to 3 substituents. The substituents include, for example, a halogen atom (e.g., fluorine, chlorine or bromine), a hydroxyl group, a $C_{1-6}$ alkyl group (e.g., methyl, ethyl), a $C_{1-6}$ alkoxy group (e.g., methoxy, ethoxy), a carboxyl group or a $C_{1-6}$ alkylcarbonyl group (e.g., formyl, acetyl). Examples of the optionally substituted aromatic group include phenyl, 4-fluorophenyl, 4-chlorophenyl, 4-bromophenyl, 4-hydroxyphenyl, 4-methoxyphenyl, 4-methylphenyl, 1-naphthyl and 2-naphthyl groups, etc. Especially preferred are phenyl and naphthyl such as 1-naphthyl and 2-naphthyl groups.

The alkyl group represented by $R_7$ is a $C_{1-6}$ alkyl group, which includes, for example, methyl, ethyl, n-propyl, iso-propyl, iso-butyl,(l-methyl)propyl, tert-butyl, (2-methyl)butyl, (3-methyl)butyl, neopentyl, (2,2-dimethyl)butyl or (3,3-dimethyl)butyl groups. Preferred is a methyl group.

$Y_1$ is preferably an aromatic hydrocarbon group. The aromatic hydrocarbon group preferably has from 6 to 14 carbon atoms and preferably includes phenyl and naphthyl. The aromatic group may optionally be substituted by from 1 to 3 substituents. The substituents are, for example, a halogen atom (e.g., fluorine, chlorine or bromine), a hydroxyl group, a $C_{1-6}$ alkyl group (e.g., methyl, ethyl), a $C_{1-6}$ alkoxy group (e.g., methoxy, ethoxy), a carboxyl group, a $C_{1-6}$ alkylcarbonyl group (e.g., formyl, acetyl) and a $C_{1-6}$ alkoxycarbonyl group (e.g., acetoxy). Examples of the optionally substituted aromatic group of $Y_1$ include phenyl, 4-fluorophenyl, 4-chlorophenyl, 4-bromophenyl, 4-hydroxyphenyl, 4-methoxyphenyl, 4-methylphenyl, 1-naphthyl 2-naphthyl groups. Especially preferred is naphthyl such as 1-naphthyl and 2-naphthyl groups.

The optionally substituted heterocyclic group represented by $R_3$ has the same meaning as defined in the optionally substituted heterocyclic group of R. Preferred is an indolyl group, especially an indole-3-yl group.

$R_5$ in the acyl group (—CO—R$_5$) represented by $R_3$ is preferably an optionally substituted heterocyclic group, or an optionally substituted amino group. The heterocyclic group of the optionally substituted heterocyclic group of $R_5$ is preferably a 5- or 6-membered heterocyclic group having from 1 to 4 hetero atoms of O, S and/or N (e.g., pyrrolyl, pyrrolinyl, pyrrolidinyl, imidazolyl, imidazolidiyl, piperidinyl, pyrazolyl, pyrazolidinyl, pyridyl, pyrimidyl, pyrazinyl, piperazinyl, pyridazinyl, triazolyl, tetrazolyl, dihydrotriazinyl, pyridyl, oxazolyl, isoxazolyl, oxadiazolyl, morpholinyl, furyl, thienyl, thiazolyl, isothiazolyl, thiazolinyl, thiadiazolyl or triazolidinyl), or a condensed heterocyclic group where any one of these groups is condensed with other ring(s) such as benzene ring(s), etc. (e.g., indolyl, isoindolyl, indolidinyl, benzimidazolyl, quinolyl, isoquinolyl, indazolyl, benzotriazolyl, tetrazolopyridyl, tetrazolopyridazinyl, benzoxazolyl, benzoxadiazolyl, benzothiazolyl or benzothiadiazolyl). Especially preferred is a piperazinyl group. These heterocyclic groups may optionally have from 1 to 3 substituents, which are preferably an optionally substituted aryl group, an optionally substituted $C_{7-15}$ aralkyl group and an optionally substituted heterocyclic group. The aryl group of the optionally substituted aryl group has from 6 to 14 carbon atoms and preferably includes phenyl and naphthyl. The aryl group which is the substituents of the heterocyclic group of $R_5$ may optionally be substituted by from 1 to 3 substituents. The substituent is, for example, a halogen atom (e.g., fluorine, chlorine or bromine), a hydroxyl group, a $C_{1-6}$ alkyl group (e.g., methyl, ethyl), a $C_{1-6}$ alkoxy group (e.g., methoxy, ethoxy), a carboxyl group, a $C_{1-6}$ alkylcarbonyl group (e.g., formyl, acetyl). Examples of the optionally substituted aryl group include phenyl, 4-fluorophenyl, 4-chlorophenyl, 4-bromophenyl, 4-hydroxyphenyl, 4-methoxyphenyl, 4-methylphenyl, 2-methoxyphenyl, 4-methoxyphenyl, 1-naphthyl and 2-naphthyl groups, etc. Preferred are phenyl, 2-methoxyphenyl and 4-methoxyphenyl groups.

The examples of the optionally substituted $C_{7-15}$ aralkyl group which is the substituents of the heterocyclic group of $R_5$ include benzyl, phenethyl, 4-chlorobenzyl, 2-methylbenzyl, 3-methylbenzyl, 4-methoxybenzyl, diphenylmethyl, triphenylmethyl, 1-naphthylmethyl, 2-naphthylmethyl. Preferably is a benzyl.

The heterocyclic group of the optionally substituted heterocyclic group which is the substituents of the heterocyclic group of $R_5$ includes a 5- or 6-membered heterocyclic group having from 1 to 4 hetero atoms of O, S and/or N (e.g., pyrrolyl, pyrrolinyl, pyrrolidinyl, imidazolyl, imidazolidiyl, piperidinyl, pyrazolyl, pyrazolidinyl, pyridyl, pyrimidyl, pyrazinyl, piperazinyl, pyridazinyl, triazolyl, tetrazolyl, dihydrotriazinyl, pyridyl, oxazolyl, isoxazolyl, oxadiazolyl, morpholinyl, furyl, thienyl, thiazolyl, isothiazolyl, thiazolinyl, thiadiazolyl or triazolidinyl), or a condensed heterocyclic group where any one of these groups is condensed with other ring(s) such as benzene ring(s), etc. (e.g., indolyl, isoindolyl, indolidinyl, benzimidazolyl, quinolyl, isoquinolyl, indazolyl, benzotriazolyl, tetrazolopyridyl, tetrazolopyridazinyl, benzoxazolyl, benzoxadiazolyl or benzothiazolyl, benzothiadiazolyl, etc.). Preferred is a pyridyl group. These heterocyclic groups may optionally have from 1 to 3 substituents on the carbon and/or nitrogen atom(s). The substituents on the carbon atom include a $C_{1-6}$ alkyl group (e.g., methyl, ethyl, n-propyl or n-butyl), a halogen atom (e.g., fluorine, chlorine, bromine or iodine), a hydroxyl group, a carboxyl group, a $C_{1-6}$ alkoxy group (e.g., methoxy, ethoxy, n-propoxy or n-butoxy), a $C_{1-6}$ alkylcarbonyl group (e.g., formyl, acetyl), etc. The substituents on the nitrogen atom include a $C_{1-6}$ alkyl group (e.g., methyl, ethyl, n-propyl or n-butyl), a $C_{1-6}$ alkylcarbonyl group (e.g., formyl, acetyl), a hydroxy-$C_{1-6}$ alkyl group (e.g., hydroxymethyl, 2-hydoxyethyl).

The substituted amino group represented by $R_5$ may be any one of mono-substituted amino groups and di-substituted amino groups.

The substituted amino groups include mono- or di $C_{1-6}$ alkylamino (for example, methylamino, dimethylamino, ethylamino, diethylamino, N-methyl-N-ethylamino and t-butylamino, N-ethyl-N-t-butylamino), $C_{3-8}$ cycloalkylamino (for example, N-cyclopentylamino or N-cyclohexylamino, $C_{6-14}$ arylamino (for example, N-phenylamino, N-(4-methylphenyl)amino, N-1-naphthylamino, N-2-maphthylamino, $C_{7-20}$ aralkylamino (for example, N-benzylamino, N-phenethylamino, N-(4-chlorobenzyl)amino, N-(2-methylbenzyl)amino, N-(3-methylbenzyl)amino, N-(4-methylbenzyl)amino, N-(2-methoxybenzyl)amino, N-(3-methoxybenzyl)amino, N-(4-methoxybenzyl)amino, diphenylmethylamino, triphenylmethylamino, 1-naphthylmethylamino or 2-naphthylmethylamino), N-$C_{1-6}$ alkyl-N-$C_{6-14}$ arylamino (for example, N-methyl-N-phenylamino), aromatic heterocycle —$C_{1-6}$ alkylamino (for example, 2-furylmethylamino, 3-furylmethylamino, 2-thienylmethylamino, 3-thienylmethylamino, indole-2-ylmethylamino or indole-3-ylmethylamino). Preferably is mono-substituted amino group —$NHR_6$.

$R_6$ is preferably $C_{6-14}$ aryl (for example, phenyl, naphthyl) or $C_{7-20}$ aralkyl (for example, benzyl, phenethyl, 4-chlorobenzyl, 2-methylbenzyl, 3-methylbenzyl, 4-methylbenzyl, 2-methoxylbenzyl, 3-methoxylbenzyl, 4-methoxylbenzyl, diphenylmethyl, triphenylmethyl, 1-naphthylmethyl, 2-naphthylmethyl).

$R_4$ has the same meaning as defined in R'. $R_4$ is preferably a hydrogen atom, a p-toluenesulfonyl (tosyl) group or a 4-methoxy-2,3,6-trimethylbenzenesulfonyl group.

$A_2$ is preferably an α-amino acid residue selected from Arg, Lys, Trp, Glu, or their derivatives. More concretely, $A_2$ is preferably an α-amino acid residue selected from Arg, Arg(Mtr), Arg(Tos), Lys, Lys(SO$_2$Nap(1)), Lys(SO$_2$Nap(2)), Lys(COPh), Lys(COCH$_2$Ph), Trp, Glu, Glu(NH—CH$_2$CH$_2$-Ph), Glu(NH—CH$_2$-Ph), Glu(NH—CH-Ph$_2$), Glu(NH—CH$_2$-Nap(1)), Glu(Php), Glu(Bzlp), Glu((2)-Pyp), Glu(2-MeOPhp), Glu(4-MeOPhp), Lys(CO—(CH$_2$)$_3$-Ph), Lys(CO—(CH$_2$)$_5$-Ph), Lys(Ac).

The α-amino acid residue represented by $A_3$ in the formula (I) is preferably represented by —NH—CHX$_3$—CO—.

Herein, $X_3$ is preferably a group of —(CH$_2$)m$^3$—$R_8$, in which m$^3$ represents an integer of from 0 to 10. m$^3$ is an integer of from 0 to 10 and preferably is an integer of from 0 to 5.

$R_8$ is preferably an optionally substituted aryl group, an optionally substituted amino group, an optionally substituted heterocyclic group, or an acyl group.

The aryl group of the optionally substituted aryl group represented by $R_8$ has the same meaning as defined in the aryl of R. Examples of the optionally substituted aryl group include, for example, phenyl, 4-fluorophenyl, 4-chlorophenyl, 4-bromophenyl, 4-hydroxyphenyl, 4-methoxyphenyl, 4-methylphenyl, 1-naphthyl or 2-naphthyl groups. Especially preferred are phenyl, 4-fluorophenyl, 4-chlorophenyl, 4-hydroxyphenyl, 1-naphthyl and 2-naphthyl groups.

The substituted amino group of the optionally substituted amino group represented by $R_8$ include mono- or di-$C_{1-6}$ alkylamino (for example, methylamino, dimethylamino, ethylamino, diethylamino, N-methyl-N-ethylamino, N-t-butylamino or, N-ethyl-N-t-butylamino), $C_{3-8}$ cycloalkylamino (for example, N-cyclopentylamino or N-cyclohexylamino, $C_{6-14}$ arylamino (for example, N-phenylamino or N-(4-methylphenyl)amino, N-1-naphthylamino, N-2-naphthylamino), $C_{7-15}$ aralkylamino (for example, N-benzylamino, N-phenethyl-amino, N-(4-chlorobenzyl)amino, N-(2-methylbenzyl)amino, N-(3-methylbenzyl)amino, N-(4-methylbenzyl)amino, N-(2-methoxybenzyl)amino, N-(3-methoxybenzyl)amino or N-(4-methoxybenzyl)amino), aromatic heterocycle-$C_{1-6}$ alkylamino (for example, 2-furylmethylamino, 3-furylmethylamino, 2-thienylmethylamino, 3-thienylmethylamino, indole-2-ylmethylamino or indole-3-ylmethylamino), acylamino group of —NH—CO—$R_{10}$, and —NHSO$_2$Y$_2$, wherein $Y_2$ is an optionally substituted aromatic group. Preferably is an acylamino group of —NH—CO—$R_{10}$ or —NHSO$_2$Y$_2$.

$R_{10}$ is preferably an optionally substituted aromatic group or an alkyl group, especially preferably an optionally substituted aromatic group.

The optionally substituted aromatic group represented by $R_{10}$ is preferably an aromatic hydrocarbon group. The aromatic hydrocarbon group has from 6 to 15 carbon atoms and is preferably phenyl or naphthyl. The aromatic group may optionally be substituted by from 1 to 3 substituents. The substituents are, for example, a halogen atom (e.g., fluorine, chlorine, bromine), a hydroxyl group, a $C_{1-6}$ alkyl group (e.g., methyl, ethyl), a $C_{1-6}$ alkoxy group (e.g., methoxy, ethoxy or hexyloxy), a carboxyl group, a $C_{1-6}$ alkylcarbonyl group (e.g., formyl, acetyl or hexanoyl). Examples of the optionally substituted aromatic group include, for example, phenyl, 4-fluorophenyl, 4-chlorophenyl, 4-bromophenyl, 4-hydroxyphenyl, 4-methoxyphenyl, 4-methylphenyl, 1-naphthyl and 2-naphthyl groups. Especially preferred are a phenyl group and a naphthyl group such as 1-naphthyl and 2-naphthyl groups.

The alkyl group represented by $R_{10}$ is a $C_{1-6}$ alkyl group, which includes, for example, methyl, ethyl, n-propyl, iso-propyl, n-butyl, iso-butyl, (1-methyl)propyl, tert-butyl, n-pentyl, (2-methyl)butyl, (3-methyl)butyl, neopentyl, n-hexyl, (2,2-dimethyl)butyl or (3,3-dimethyl)butyl groups.

$Y_2$ is preferably an optionally substituted aryl group. The aryl group has from 6 to 14 carbon atoms and is preferably phenyl or naphthyl. The aryl group may optionally be substituted by from 1 to 3 substituents. The substituents are, for example, a halogen atom (e.g., fluorine, chlorine, bromine), a hydroxyl group, a $C_{1-6}$ alkyl group (e.g., methyl, ethyl), a $C_{1-6}$ alkoxy group (e.g., methoxy, ethoxy), a carboxyl group, a $C_{1-6}$ alkylcarbonyl group (e.g., formyl, acetyl). Examples of the optionally substituted aryl group include, for example, phenyl, 4-fluorophenyl, 4-chlorophenyl, 4-bromophenyl, 4-hydroxyphenyl, 4-methoxyphenyl, 4-methylphenyl, 1-naphthyl or 2-naphthyl groups. Especially preferred are naphthyl groups such as 1-naphthyl and 2-naphthyl groups.

The heterocyclic group of the optionally substituted heterocyclic group represented by $R_8$ has the same meaning as defined in the optionally substituted heterocyclic group of R. Preferred is an indolyl group, especially preferably an indole-3-yl group.

The acyl group represented by $R_8$ has the same meaning as defined in the acyl group of R. Preferred is N-monosubstituted carbamoyl group (—CO—$NHR_9$).

$R_9$ is preferably $C_{1-6}$ alkyl (e.g., methyl, ethyl, t-butyl) or $C_{7-20}$ aralkyl (e.g., benzyl, phenethyl, 4-chlorobenzyl, 2-methylbenzyl, 3-methylbenzyl, 4-methylbenzyl, 2-methoxybenzyl, 3-methoxybenzyl, 4-methoxybenzyl, diphenylmethyl, triphenylmethyl, 1-naphthylmethyl, 2-naphthylmethyl). Especially preferably is benzyl.

$A_3$ is preferably an α-amino acid residue selected from Phe, Ala, Tyr, Lys, Asp, Trp, or their derivatives. More concretely, $A_3$ is preferably an α-amino acid residue selected from Phe, Nal, (p-Cl)Phe, (p-F)Phe, Tyr, Lys(CO-Ph), Lys (CO-Nap(1)), Asp(NH—$CH_2$-Ph), Trp, Lys($SO_2$Nap(1)).

The α-amino acid residue represented by $A_4$ in the formula (I) is preferably represented by —NH—$CHX_4$—CO—.

Herein, $X_4$ is preferably a group of (1) —$(CH_2)m^4$—$R_{11}$, wherein $m^4$ represents an integer of from 0 to 10; and $R_{11}$ is preferably a hydrogen atom, a hydroxyl group, an optionally substituted amino group, an optionally substituted alkyl group, an optionally substituted aryl group, or an optionally substituted heterocyclic group. or (2) —$(CH_2)n^4$—NH—C(=NH)—NH—$R_{12}$, wherein $n^4$ represents an integer of from 1 to 5; and $R_{12}$ is a hydrogen atom, nitro or an optionally substituted benzenesulfonyl group. $m^4$ is an integer of from 0 to 10, preferably an integer of from 0 to 5. $n^4$ is an integer of from 1 to 5 and preferably is 3.

The substituted amino group of the optionally substituted amino group represented by $R_{11}$ has the same meaning as defined in the substituted amino groups of R. The substituted amino group is preferably an acyl amino group represented by —NH—CO—$R_{13}$.

$R_{13}$ is preferably a $C_{1-6}$ alkyl (for example, methyl, ethyl or propyl, an optionally substituted $C_{6-14}$ aryl group (for example, phenyl, naphthyl), an optionally substituted heterocyclic group.

The above mentioned aryl group of $R_{13}$ may optionally be substituted by from 1 to 3 substituents. The substituents include $C_{1-6}$ alkyl (e.g., methyl, ethyl, n-propyl or n-butyl), halogen atom (e.g., fluorine, chlorine, bromine or iodine), hydroxyl, carboxyl, $C_{1-6}$ alkoxy (methoxy, ethoxy, n-propoxy or n-butoxy), $C_{1-6}$ alkanoyl (formyl or acetyl).

The optionally substituted heterocyclic group represented by $R_{13}$ has the same meaning as defined in the optionally substituted heterocyclic group of $R_{15}$. Preferred is a pyridyl group.

The optionally substituted alkyl group represented by $R_{11}$ has the same meaning as defined in the optionally substituted alkyl group of R. Preferred is an iso-propyl group.

The aryl group of the optionally substituted aryl group represented by $R_{11}$ has the same meaning as defined in the optionally substituted aryl group of R. Examples of the optionally substituted aryl group of $R_{11}$ include phenyl, 4-fluorophenyl, 4-chlorophenyl, 4-bromophenyl, 4-hydroxyphenyl, 4-methoxyphenyl, 4-methylphenyl, 1-naphthyl or 2-naphthyl groups. Of these, preferred are phenyl and 4-hydroxyphenyl groups.

The heterocyclic group of the optionally substituted heterocyclic group represented by $R_{11}$ has the same meaning as defined in the optionally substituted heterocyclic group of R. Preferred is an indolyl group, especially preferably an indole-3-yl group.

$R_{12}$ has the same meaning as defined in R'. $R_{12}$ is preferably a hydrogen atom or a p-toluenesulfonyl group (tosyl group).

$A_4$ is preferably an α-amino acid residue selected from Ala, Leu, Phe, Trp, Ser, Arg, Lys, Tyr, or their derivatives. More concretely, $A_4$ is preferably an α-amino acid residue selected from Ala, Leu, Phe, Trp, Ser, Arg, Lys(Nic), Tyr.

The α-amino acid residue represented by $A_5$ in the formula (I) is preferably represented by —NH—$CHX_5$—CO—.

Herein, $X_5$ is preferably a group of —$(CH_2)m^5$—$R_{14}$, wherein $m^5$ represents an integer of from 0 to 10), wherein $m^5$ is an integer of from 0 to 0 and preferably is an integer of from 0 to 5.

$R_{14}$ is preferably an optionally substituted aryl group, an optionally substituted heterocyclic group, an optionally substituted alkyl group, or an optionally substituted amino group.

The aryl group of the optionally substituted aryl group of $R_{14}$ has the same meaning as defined in the aryl group of R. Examples of the optionally substituted aryl group include phenyl, 4-fluorophenyl, 4-chlorophenyl, 4-bromophenyl, 4-hydroxyphenyl, 4-methoxyphenyl, 4-methylphenyl, 1-naphthyl or 2-naphthyl groups. Especially preferred is a phenyl group.

The heterocyclic group of the optionally substituted heterocyclic group represented by $R_{14}$ has the same meaning as defined in the optionally substituted heterocyclic group of R. Preferred is an indolyl group, especially preferably an indole-3-yl group.

The optionally substituted alkyl group represented by $R_{14}$ has the same meaning as defined in the optionally substituted alkyl group of R. Preferred is an iso-propyl group.

The substituted amino group of $R_{14}$ has the same meaning as defined in the substituted amino group of R.

The optionally substituted amino group represented by $R_{14}$ is preferably —$NHSO_2Y_3$, wherein $Y_3$ is an optionally substituted aromatic group. The aromatic group of $Y_3$ is preferably an aromatic hydrocarbon group. The aromatic hydrocarbon group has from 6 to 14 carbon atoms and preferably includes phenyl and naphthyl. The aromatic group may be substituted by from 1 to 3 substituents. The substituents are, for example, a halogen atom (e.g., fluorine, chlorine, bromine), a hydroxyl group, a $C_{1-6}$ alkyl group (e.g., methyl, ethyl), a $C_{1-6}$ alkoxy group (e.g., methoxy, ethoxy or hexyloxy), a carboxyl group, a $C_{1-6}$ alkylcarbonyl group (e.g., formyl, acetyl) or hexanoyl. Examples of the optionally substituted aromatic group include phenyl, 4-fluorophenyl, 4-chlorophenyl, 4-bromophenyl, 4-hydroxyphenyl, 4-methoxyphenyl, 4-methylphenyl, 1-naphthyl and 2-naphthyl groups, etc. Especially preferred is a naphthyl group such as 1-naphthyl or 2-naphthyl groups.

$A_5$ is preferably an α-amino acid residue selected from Trp, Phe, Leu, Lys, or their derivatives. Concretely, $A_5$ is preferably an α-amino acid residue selected from Trp, Phe, Leu, Lys(SO₂Nap(1)).

Any one of α-amino acid residues in the cyclic pentapeptide of formula (I) is L- or D-configuration.

Preferably $A_1$, $A_3$ and $A_5$ are of L-configuration and $A_4$ is of a D-configuration or where $A_1$, $A_3$ and $A_5$ are of D-configuration and $A_4$ is of an L-configuration are preferred in view of their physiological activity.

A cyclic pentapeptide in this invention preferably comprises Arg or derivatives thereof for showing LH-RH receptor antagonistic activity.

A cyclic pentapeptide or a salt thereof of a formula (II):

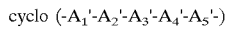  (II)

is a novel compound among the cyclic pentapeptide to be represented by formula (I), wherein $A_1'$ represents Arg or derivative thereof, and $A_1'$, $A_3'$, $A_4'$ and $A_5'$ independently represent an amino acid residue except Gly, Pro and an acidic amino acid residue, or a salt thereof.

The cyclic pentapeptide preferably contains (1) at least Arg, Lys, Trp and Leu, wherein Arg, Lys, Trp or Leu may be its derivatives, or (2) at least Arg, Phe and Ala, wherein Arg, Phe or Ala may be its derivatives.

Herein, $A_1'$, $A_2'$, $A_3'$, $A_4'$ and $A_5'$ independently represent L- or D-configuration. In one embodiment, preferably $A_1'$ and $A_3'$ represent L-configuration and $A_2'$ and $A_4'$ represent D-configuration. In another embodiment, preferably $A_2'$, $A_4'$ and $A_5'$ represent L-configuration and $A_3'$ represent D-configuration.

An Arg derivative preferably includes Arg containing protecting group at the guanidino group in Arg.

The protecting group include for example, nitro, tosil (TOS), p-methoxybenzenesulfonyl, mesitylenesulfonyl, pentamethylbenzenesulfonyl, 4-methoxy-2,3,6-trimethylbenzenesulfonyl(Mtr), carbobenzoxy, isobornyloxycarbonyl or adamantyloxycarbonyl.

Of the above-mentioned ones, the protecting group is preferably nitro, tosil, p-methoxybenzenesulfonyl, mesitylenesulfonyl, pentamethylbenzenesulfonyl, 4-methoxy-2,3,6-trimethylbenzenesulfonyl, especially preferably tosil(TOS), 4-methoxy-2,3,6-trimethylbenzenesulfonyl(Mtr).

The guanidino group may be protected in the form of salts of acids (such as benzenesulfonic acid, toluenesulfonic acid, hydrochloric acid and sulfuric acid).

The acidic amino acid is, for example, an amino acid with an acidic group such as carboxyl, sulfonyl or tetrazolyl as a side chain. Examples of such amino acids include glutamic acid, aspartic acid, cysteic acid, homocysteic acid, β-(5-tetrazolyl)alanine and 2-amino-4-(5-tetrazolyl)butyric acid.

The cyclic pentapeptide or salt thereof doesn't contain any acidic amino acid residues. However, if the amino acid residue which the acidic property is lost, can be included in the cyclic pentapeptide of this invention. For example, Glu or Asp is an acidic amino acid residue which has an acidic (carboxyl) group, however, for example Glu (NH—CH₂-Ph), Asp (NH—CH₂-Ph), etc. which the acidic group thereof is substituted, is not acidic. Therefore these amino acid residues can include Any one of $A_2'$-$A_3'$, $A_3'$-$A_4'$ and $A_4'$-$A_5'$ is preferably Trp-Leu or Ala-Trp.

The cyclic pentapeptide or salt thereof includes for example, a cyclic pentapeptide comprising Arg, Glu, Lys, Trp and Leu, or their derivatives, a cyclic pentapeptide comprising Gly, Arg, Phe, Ala and Trp, or their derivatives, a cyclic pentapeptide comprising Ala, Arg, Phe, Ala and Trp, or their derivatives, a cyclic pentapeptide comprising Gly, Arg, Phe, Ala and Phe, or their derivatives, or a cyclic pentapeptide comprising Arg, Phe, Phe, Trp and Ala, or their derivatives.

Arg derivatives is preferably Arg(Mtr), Arg(Tos). Lys derivatives is preferably Lys(Isopropyl), Lys(SO₂Nap(1)), Lys(SO₂Nap(2)), Lys(COPh), Lys(COCH₂Ph), Lys(CO—(CH₂)₃-Ph), Lys(CO—(CH₂)₅-Ph), Lys(Ac), Lys(CO-Nap (1), Lys(Nic). Glu derivatives is preferably Glu(NH—CH₂CH₂-Ph). Glu(NH—CH₂-Ph), Glu(NH—CH-Ph₂), Glu (NH—CH₂-Nap(1)), Glu(Php), Glu(Bzlp), Glu((2)-Pyp), Glu(2-MeOPhp), Glu(4-MeOPhp). Gly derivatives is preferably Phg, Thg. Phe derivatives is preferably (p-Cl)Phe, (p-F)Phe. Ala derivatives is preferably Nal.

For example, a cyclic pentapeptide includes the cyclic pentapeptide described in working examples.

Preferred is cyclo(-Arg-D-Lys (COCH₂CH₂CH₂CH₂CH₂Ph)-Tyr-D-Trp-Leu-), cyclo(-Arg-D-Glu(NHCH₂CH₂Ph)-Lys(CONap(1))-D-Trp-Leu-), cyclo(-Phg-D-Arg(Tos)-Phe-D-Ala-Trp-), cyclo(-Ala-D-Arg(Tos)-Phe-D-Ala-Trp-), cyclo(-Phg-D-Arg(Tos)-Phe-D-Ala-Phe-), cyclo(-Phg-D-Arg-Phe-D-Ala-Trp-), or salt thereof.

Salts (or pharmaceutically-acceptable salts) of the cyclic pentapeptides (I) of the present invention include, for example, metal salts (e.g., sodium salts, potassium salts, calcium salts, magnesium salts, etc.) thereof, salts thereof with bases or basic compounds (e.g., ammonium salts, arginine salts, etc.), inorganic acid-added salts (e.g., hydrochlorides, sulfates, phosphates, etc.) thereof, organic acid-added salts (e.g., acetates, propionates, citrates, tartrates, malates, oxalates, etc.) thereof, etc.

The abbreviations for amino acids and peptides as referred to herein are those which are defined in IUPAC-IUB Commission Biochemical Nomenclature are those which are popularly used in the art. Examples of the abbreviations are mentioned below.

Ala: Alanine

Leu: Leucine

Trp: Tryptophan

Tyr: Tyrosine

Phe: Phenylalanine

Glu: Glutamic acid

Asp: Aspartic acid

Phg: Phenylglycine (p-Cl)Phe: Parachlorophenylalanine (p-F)Phe: Parafluorophenylalanine Thi: 2-Thienylalanine Lys: Lysine Arg: Arginine Nal: 2-Naphthylalanine Thg: Thienylglycine Thg(2): 2-Thienylglycine Arg(Tos): $N^g$-pToluenesulfonylarginine Arg(Mtr): $N^g$-(4-Methoxy-2,3,6-trimethylbenzenesulfonyl)arginine Lys(Isopropyl): $N^\epsilon$-Isopropyllysine Lys (SO₂Nap(1)): $N^\epsilon$-(1-Naphthalenesulfonyl)lysine Lys (SO₂Nap(2)): $N^\epsilon$-(2-Naphthalenesulfonyl)lysine Lys(COPh): $N^\epsilon$-Benzoyllysine Lys(COCH₂Ph): $N^\epsilon$-Phenylacetyllysine Lys (CO—(CH₂)₃-Ph): $N^\epsilon$-(4-phenyl)butyryllysine Lys (CO—(CH₂)₃-Ph): $N^\epsilon$-(6-phenyl)hexanoyllysine Lys(Ac): $N^\epsilon$-Acetyllysine
Lys(CO-Nap(1)): $N^\epsilon$-(1-Naphthoyl)lysine
Lys(Nic): $N^\epsilon$-Nicotinoyllysine
Glu(NH—CH$_2$CH$_2$-Ph): N-γ-Glutamylphenethylamine
Glu(NH—CH$_2$-Ph): N-γ-Glutamylbenzylamine
Glu(NH—CH$_2$-Ph$_2$): (N-γ-Glutamyl)diphenylmethylamine
Glu(NH—CH$_2$-Nap(1)): (N-γ-Glutamyl)-1-naphthylmethylamine
Glu(Php): 1-γ-Glutamyl-4-phenylpiperazine
Glu(Bzlp): 1-γ-Glutamyl-4-benzylpiperazine
Glu((2)-Pyp): 1-γ-Glutamyl-4-(2-pyridyl)piperazine
Glu(2-MeOPhp): 1-γ-Glutamyl-4-(2-methoxyphenyl)piperazine
Glu(4-MeOPhp): 1-γ-Glutamyl-4-(4-methoxyphenyl)piperazine
Asp(NH—CH$_2$-Ph): N-β-Aspartylbenzylamine The substituents, the protective groups and the reagents referred to herein are represented by the following abbreviations.

DMF: N,N-dimethylformamide
AcOEt: Ethyl acetate
Boc: Tert-butoxycarbonyl
Bzl: Benzyl
OPac: Phenacyl ester
HONB: N-hydroxy-5-norbornene-2,3-dicarboximide
ONB: HONB ester
HOBt: 1-Hydroxybenzotriazole
DCC: N,N'-dicyclohexylcarbodiimide
DCU: N,N'-dicyclohexylurea
DCHA: N,N-dicyclohexylamine
CHA: Cyclohexylamine
WSCD: 1-Ethyl-3-(3-dimethylaminopropyl)carbodiimide
Tos: Tosyl
TosOH: Paratoluenesulfonic acid
Ph: Phenyl
Php: Phenylpiperazine
Bzlp: Benzylpiperazine
(2)-Pyp: 2-Pyridylpiperazine
MeOPhp: Methoxyphenylpiperazine
Nap(1): 1-Naphthalene
Nap(2): 2-Naphthalene
Nic: Nicotinoyl
Br-Z: 2-Bromobenzyloxycarbonyl
Cl-Z: 2-Chlorobenzyloxycarbonyl
DIEA: Diisopropylethylamine
TFA: Trifluoroacetic acid
Fmoc: 9-Fluorenylmethoxycarbonyl
Mtr: 4-Methoxy-2,3,6-trimethylbenzenesulfonyl
DCM: Dichloromethane
HBTU: 2-Benzotriazolyl-1,1,3,3-tetramethylammonium hexafluorophosphate
PyBop: Benzotriazolyloxytrispyrrolidinophosphonium hexafluorophosphate
Pyr: Pyridine
Ac: Acetyl
Wang Resin: 4-(hydroxymethyl)phenoxymethyl resin The cyclic pentapeptides of the formula (I) or salts thereof of the present invention can be produced by conventional means of producing peptides. Namely, the compound of the formula (I) can be produced either by liquid phase synthesis or by solid phase synthesis, but liquid phase synthesis is preferred in some cases. The means of producing peptides can be conducted in accordance with known methods such as those written by Bodansky, M. & Ondetti, M. A. in Peptide Synthesis, Interscience, New York, 1996; by Finn, F. M. & Hofman, K. in The Proteins, Vol. 2 (edited by Henrath, H. & Hill, R. L.), Academic Press Inc., New York, 1976; by Izumiya, N., et al. in Bases and Experiments of Peptide Synthesis, Maruzen, 1985; by Yajima, H., Sakakibara, S., et al. in Biochemical Experiments, Lecture 1 (edited by the Biochemical Society of Japan), Tokyo Kagaku Dojin, 1977; by Kimura, T., et al. in Continuation of Biochemical Experiments, Lecture 2 (edited by the Biochemical Society of Japan), Tokyo Kagaku Dojin, 1987; by Steward, J. M. & Young, J. D. in Solid Phase Peptide Synthesis, Pierce Chemical Co., Illinois, 1984, etc. For example, mentioned are azide methods, chloride methods, acid anhydride methods, mixed acid anhydride methods, DCC methods, active ester methods, methods of using Woodward Reagent K, carbonyldiimidazole methods, redox methods, DCC/HONB methods, methods of using BOP reagent, etc. As one example, it is possible to produce a cyclic pentapeptide of formula (I) or a salt thereof by condensing a starting compound having a reactive carboxyl group, which corresponds to one of two fragments to be obtained by dividing a cyclic pentapeptide of formula (I) at any desired position, with another starting compound having a reactive amino group, which corresponds to the other one of the fragments, by ordinary means known in the art of peptide synthesis to give a linear tetrapeptide, followed by ring-closing and condensing the resulting intermediate by known condensation. If the condensate thus produced have protective group (s), the protective group(s) can be removed by known means to obtain the intended peptide. In particular, in solid phase peptide synthesis, an amino acid of which the functional group(s) that shall not participate in the reaction has/have been protected is bonded to an insoluble carrier such as a Pam resin or the like via the carboxyl group of the amino acid, then the amino-protecting group(s) is/are removed, and thereafter the thus-fixed amino acid is condensed with another amino acid of which the functional group(s) that shall not participate in the reaction has/have been protected. This process is repeated until the intended, protected peptide is synthesized. Then, the protecting group(s) in the thus-synthesized peptide is/are removed by ordinary means, such as treatment with hydrogen fluoride, treatment with trifluoromethanesulfonic acid, treatment with trifluoroacetic acid or the like, while the bond of the peptide to the insoluble carrier is cut to isolate the intended peptide.

The above-mentioned first and second starting compounds are generally amino acids and/or peptide fragments. By bonding the two to each other, the intended cyclic pentapeptides of formula (I) or salts thereof are formed. These are generally linear or branched. The "reactive carboxyl group" indicates a carboxyl group itself or an activated carboxyl group. The "reactive amino group" indicates an amino group itself or an activated amino group. In general, one of the two functional groups that participate in the above-mentioned condensation is activated. The other carboxyl or amino group that does not participate in the condensation is protected prior to the condensation.

The protection of the functional groups that shall not participate in the reaction in the starting compounds and the protecting groups for the compounds, the removal of the protecting groups, and the activation of the functional groups that participate in the reaction in the compounds can be suitably selected from known groups and known means.

As examples of the protecting groups for the amino groups in the starting compounds, mentioned are benzyloxycarbonyl, tert-butyloxycarbonyl, tert-amyloxycarbonyl, isobornyloxycarbonyl, 4-methoxybenzyloxycarbonyl, 2-chlorobenzyloxycarbonyl, adamantyloxycarbonyl, trifluoroacetyl, phthaloyl, formyl, 2-nitrophenylsulfenyl, diphenylphosphinothioyl and 9-fluorenylmethyloxycarbonyl groups, etc. As examples of the protecting groups for the carboxyl groups in the starting compounds, mentioned are alkyl esters (for example, ester groups of methyl, ethyl, propyl, butyl, tert-butyl, cyclopentyl, cyclohexyl, cycloheptyl, cyclooctyl, 2-adamantyl, etc.), benzyl esters, 4-nitrobenzyl esters, 4-methoxybenzyl esters, 4-chlorobenzyl esters, benzhydryl esters, phenacyl esters, benzyloxycarbonyl hydrazides, tert-butyloxycarbonyl hydrazides, trityl hydrazides, etc.

Thiol-protecting groups for cysteine include, for example, 4-methoxybenzyl, 4-methylbenzyl, benzyl, tert-butyl, adamantyl, trityl, acetamidomethyl, carbomethoxysulfenyl, 3-nitro-2-pyridinesulfenyl, trimethylacetamidomethyl, etc.

The hydroxyl group in serine can be protected, for example, by esterification or etherification. The groups suitable for the esterification include, for example, lower alkanoyl groups such as acetyl group, etc., aroyl groups such as benzoyl group, etc., groups to be derived from carbonic acid such as benzyloxycarbonyl group, ethyloxycarbonyl group, etc. The groups suitable for the etherification include, for example, benzyl group, tetrahydropyranyl group, tert-butyl group, etc. However, it is not always necessary to protect the hydroxyl group in serine.

The protecting groups for the phenolic hydroxyl group in tyrosine include, for example, benzyl, 2,6-dichlorobenzyl, 2-nitrobenzyl, 2-Bromobenzyloxycarbonyl, tert-butyl, etc. However, the protection of the phenolic hydroxyl group is not always necessary.

Methionine may be protected in the form of its sulfoxide.

The protecting groups for the imidazole moiety in histidine includes, for example, paratoluenesulfonyl, 4-methoxy-2,3,6-trimethylbenzenesulfonyl, 2,4-dinitrophenyl, benzyloxymethyl, tert-butoxymethyl, tert-butoxycarbonyl, trityl, 9-fluorenylmethyloxycarbonyl, etc. However, the protection of the imidazole moiety is not always necessary.

The protecting groups for the indole moiety in tryptophan include, for example, formyl, 2,4,6-trimethylbenzenesulfonyl, 2,4,6-trimethoxybenzenesulfonyl, 4-methoxy-2,3,6-trimethylbenzenesulfonyl, 2,2,2-trichloroethyloxycarbonyl, diphenylphosphinothioyl, etc. However, the protection of the indole moiety is not always necessary.

The starting compounds of which the carboxyl group(s) has/have been protected include, for example, the corresponding acid anhydrides, azides, active esters [e.g., esters with alcohols (such as pentachlorophenol, 2,4,5-trichlorophenol, 2,4-dinitrophenol, cyanomethyl alcohol, paranitrophenol, N-hydroxy-5-norbornene-2,3-dicarboximide, N-hydroxysuccinimide, N-hydroxyphthalimide, N-hydroxybenzotriazole)], etc. The starting compounds of which the amino group(s) has/have been protected include, for example, the corresponding phosphoric acid amides.

The condensation can be conducted in the presence of solvents. The solvents can be suitably selected from those which are known usable in peptide condensation. For example, employable are anhydrous or hydrous dimethylformamide, dimethylsulfoxide, pyridine, chloroform, dioxane, dichloromethane, tetrahydrofuran, acetonitrile, ethyl acetate, N-methylpyrrolidone or appropriate mixtures of these. The reaction temperature can be suitably selected from the temperature range which is known applicable to peptide bond formation. In general, it is suitable selected from the range between about −20° C. and about 30° C. The reaction time is usually between 30 minutes and 24 hours.

The intramolecular cyclization is conducted in accordance with conventional means and can be effected at any desired position of the peptide to be cyclized by known methods. For example, the terminal α-carboxyl-protecting group of the C-terminal amino acid in a protected peptide is removed by known methods, then the thus-deprotected group is activated by known methods, and thereafter the terminal α-amino acid residue of the N-terminal amino acid in the peptide is removed by known methods while the peptide is intramolecularly cyclized. Alternatively, both the terminal α-carboxyl-protecting group of the C-terminal amino acid and the terminal α-amino-protecting group of the N-terminal amino acid in a protected peptide are removed at the same time and thereafter the thus-deprotected peptide is intramolecularly cyclized by known condensation. As the case may be, it will be preferable to conduct the intramolecular cyclization in a highly-diluted condition.

To remove the protecting groups, for example, employable is catalytic reduction of protected peptides in a hydrogen stream in the presence of a catalyst such as Pd black, Pd-carbon or the like, acid treatment thereof with anhydrous hydrogen fluoride, methanesulfonic acid, trifluoromethanesulfonic acid, trifluoroacetic acid or a mixture of these, or reduction thereof with sodium in liquid ammonia. The deprotection by acid treatment is conducted, in general, at a temperature falling between −20° C. and 40° C. In the acid treatment, the addition of a cation-sequestering agent, such as anisole, phenol, thioanisole, metacresol, paracresol, dimethylsulfide, 1,4-butane-dithiol or 1,2-ethane-dithiol, to the reaction system is effective. 2,4-Dinitrophenyl group to be used as the imidazole-protecting group in histidine can be removed by thiophenol treatment. Formyl group to be used as the indole-protecting group in tryptophan can be removed by alkali treatment with dilute sodium hydroxide, dilute ammonia or the like, apart from the deprotection by the above-mentioned acid treatment to be conducted in the presence of 1,2-ethane-dithiol, 1,4-butane-dithiol or the like.

The cyclic pentapeptides (I) thus produced in the manner as mentioned above are, after the reaction, can be collected by ordinary means of separation and purification of peptides, for example, by extraction, partition, re-precipitation, re-crystallization, column chromatography, high-performance liquid chromatography, etc.

The cyclic pentapeptides (I) of the present invention can be obtained as metal salts (e.g., sodium salts, potassium salts, calcium salts, magnesium salts, etc.) thereof, salts thereof with bases or basic compounds (e.g., ammonium salts, arginine salts, etc.), and acid-added salts thereof, especially as pharmaceutically-acceptable acid-added salts thereof, by per-se known methods. For example, mentioned are salts of the cyclic pentapeptides (I) with inorganic acids (e.g., hydrochloric acid, sulfuric acid, phosphoric acid) or organic acids (e.g., acetic acid, propionic acid, citric acid, tartaric acid, malic acid, oxalic acid, methanesulfonic acid), etc.

The thus-obtained cyclic pentapeptides (I) or salts thereof of the present invention have an excellent antagonistic effect against LH-RH receptors, while having low toxicity. Therefore, these can be safely used for curing mammals (e.g., human beings, monkeys, cattle, horses, dogs, cats, rabbits, rats, mice, etc.) of male hormone- or female hormone-dependent disorders and also those of disorders to be caused by the hyperhormogenesis of such sex hormones, by retarding the secretion of gonadotropic hormone in them due to the LH-RH receptor antagonistic effect of the compounds to thereby control the sex hormone concentration in the blood in them. Specifically, the compounds of the present invention are useful for curing sex hormone-dependent cancers (e.g., prostatic cancer, uterine cancer, mammary cancer, pituitary tumor, etc.), prostatomegaly, endometriosis, hysteromyoma, puberty precox, amenorrhea, premenstrual syndromes, multilocular ovarian syndromes, comedo, etc. In addition, the compounds of the present invention are also useful for the control of male and female propagation (for example, as pregnancy controlling agents, menstrual cycle controlling agents, etc.). Moreover, the compounds of the present invention can be used as contraceptive medicines for men and women and as evaluation inducers for women. Furthermore, the compounds of the present invention are useful in the livestock industry for the control of the estrus of animals and also for the improvement in the quality of meat and for the promotion of the growth of animals. In addition, the compounds of the present invention are useful as spawning promoters for fishes. The compounds of the present invention can be used singly but it is also effective to combine them with steroidal or non-steroidal anti-androgenic agents or anti-estrogenic agents. The compounds of the present invention can be used for inhibiting the transient increase in the testosterone concentration in blood (flare phenomenon) which may be caused by administration of super-agonists such as leuprorelin acetate, etc.

Where the compounds of the present invention are used as medicines for preventing and curing the above-mentioned disorders or are used in the livestock or marine products industry, they can be parenterally or perorally administered by per-se known methods.

It is mixed with a pharmaceutically acceptable carrier or diluent and usually administered orally as a solid preparation such as tablet, capsule, granule or powder, or non-orally as intravenous, subcutaneous or intramuscular injection, or as suppository or sublingually administrable tablet.

Where the cyclic pentapeptides (I) or salts thereof of the present invention are used as LH-RH antagonists for parenteral administration, in general, they are administered as liquid preparations (e.g., injections). The injections include intravenous injection and also subcutaneous injection, endermic injection, intramuscular injection, intravenous drip injection, etc. These injections can be prepared by per-se known methods, for example, by dissolving, suspending or emulsifying the compounds having an LH-RH receptor antagonistic effect in sterile, aqueous liquids or oily liquids. The aqueous liquids for injection include distilled water for injection, physiological saline solution, isotonic liquids containing glucose and other adminicula (e.g., D-sorbitol, D-mannitol, sodium chloride, etc.), etc. These may be combined with suitable dissolution aids, such as alcohols (e.g., ethanol), polyalcohols (e.g., propylene glycol, polyethylene glycol), nonionic surfactants (e.g., Polysorbate 80 (registered trade name), HCO-50 (registered trade name)), etc. The oily liquids for injection include sesame oil, soybean oil, etc., which may be combined with dissolution aids such as benzyl benzoate, benzyl alcohol, etc. In addition, these may also be combined with buffers (e.g., phosphate buffers, sodium acetate buffers), pain-relieving agents (e.g., benzalkonium chloride, procaine hydrochloride, etc.), stabilizers (e.g., human serum albumin, polyethylene glycol, etc.), preservatives (e.g., benzyl alcohol, phenol, etc.), etc. The prepared injections are generally filled in suitable ampoules. One dose of the preparations varies, depending on the subjects to which it is administered, the organs to which it is directed, the conditions of the patients, the administration routes, etc. For example, it is advantageous to conduct intravenous injection of from 0.01 mg to 100 mg or so, preferably from 0.01 mg to 50 mg or so, more preferably from 0.01 mg to 20 mg or so, in terms of the active compound, per kg of the body weight of the patient.

For peroral administration, the compounds of the present invention are administered as peroral preparations such as powders, tablets, granules, capsules, etc. To prepare such peroral preparations, the compounds may be mixed with pharmaceutically-acceptable carriers. The carriers include vehicles (e.g., lactose, starch, etc.), lubricants (e.g., magnesium stearate, talc, etc.), binders (e.g., hydroxypropyl cellulose, hydroxypropylmethyl cellulose, macrogol, etc.), disintegrators (e.g., starch, calcium carboxymethyl cellulose, etc.), etc. If desired, other additives, such as preservatives (e.g., benzyl alcohol, chlorobutanol, methyl parahydroxybenzoate, propyl parahydroxybenzoate, etc.), antioxidants, colorants, sweeteners, etc. may also be added to the preparations. One dose of the preparations is generally from 5 mg to 1 g or so, preferably from 10 mg to 100 mg or so, in terms of the active compound, per kg of the body weight of the patient.

In addition, the compounds of the present invention can be administered as slow-release preparations such as those disclosed in Japanese Patent Laid-Open No. 7-69917. Concretely, the cyclic pentapeptides (I) or salts thereof of the present invention are combined with biodegradable polymers (e.g., polyesters of fatty acids, copolymers of glycolic acid and lactose, etc.) to produce slow-release preparations.

EXAMPLES

The LH-RH receptor antagonists of the present invention are effective as medicines for preventing and curing sex hormone-dependent cancers (e.g., prostatic cancer, uterine cancer, mammary cancer, pituitary tumor, etc.), prostatomegaly, endometriosis, hysteromyoma, puberty precox, amenorrheal syndromes, multilocular ovarian syndromes, comedo, etc. and are also effective as pregnancy controlling agents (e.g., contraceptives, etc.) and menstrual cycle controlling agents. Moreover, these are also useful in the livestock industry for the control of the estrus of animals and also for the improvement in the quality of meat and for the control of the growth of animals, as well as in the marine products industry as spawning promoters for fishes.

The present invention is described more concretely hereinunder with reference to the following examples.

All amino acids except Gly in working examples are of L-configuration unless otherwise noted.

The conditions for thin layer chromatography and HPLC employed in the following examples are as follows:

(1) Thin layer chromatography (TLC):
   Merck Kieselgel 60F254
   TLC solvent: chloroform-methanol (95:5)
   $R_f$: Rate of flow (2) HPLC:
   Column: R-ODS-5-ST (4.6×150 m, produced by YMC Co.)

Eluents:
  Solution A (aqueous 0.1%-trifluoroacetic acid solution)
  Solution B (0.1%-trifluoroacetic acid-containing acetonitrile)
Conditions for elution:
  Solution A was applied to the column for 1 minute, and then linear concentration gradient elution was conducted for 35 minutes by applying to the column a mixture of Solution A and Solution B at varying ratios, Solution A:Solution B, of from 100:0 to 30:70.
Flow rate: 1.0 ml/min Example 1

Synthesis of cyclo(-Arg-D-Lys($SO_2$Nap(1))-Tyr-D-Trp-Leu-)

1) Synthesis of Boc-D-Trp-Leu-OBzl:

H-Leu-OBzl.Tos (27.6 g) was dissolved in DMF (100 ml) and cooled with ice, and diisopropylethylamine (13.9 ml) and Boc-D-Trp-ONB (prepared from 23.4 g of Boc-D-Trp-OH, 15.1 g of HONB and 17.3 g of DCC) were added thereto and stirred overnight. The DCU produced was removed by filtration, the resulting filtrate was concentrated, the resulting concentrate was dissolved in AcOEt (500 ml), and N,N-diisopropylethylamine (10.0 ml) was added thereto and stirred for 10 minutes. Water (500 ml) was added to the resulting mixture, and the AcOEt layer was separated. This was washed with aqueous 10%-citric acid solution, saturated saline solution, aqueous saturated sodium hydrogencarbonate solution and saturated saline solution, then dried with anhydrous sodium sulfate and concentrated to obtain an oily product.

Yield: 35.8 g (100%)
FAB-MS (M+H)$^+$: 508 (theoretical value: 508)

2) Synthesis of Boc-D-Trp-Leu-OPac:

Boc-D-Trp-Leu-OBzl (34.3 g) was dissolved in methanol (500 ml) and subjected to catalytic reduction in a hydrogen stream in the presence of 10%-Pd-carbon as the catalyst. The catalyst was removed by filtration, the resulting filtrate was concentrated to 100 ml, and an aqueous solution (10 ml) of $Cs_2CO_3$ (11.0 g) was dropwise added thereto. The solvent was removed by distillation, the residue was dissolved in DMF (200 ml), and a DMF (50 ml) solution of phenacyl bromide (13.5 g) was added thereto and stirred overnight. The solvent was removed by distillation, and the residue was dissolved in AcOEt (300 ml). Then, the resulting solution was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, chloroform), and the intended product was obtained as a precipitate from chloroform-petroleum ether.

Yield: 37.6 g (76.4%)
$R_f$: 0.46
m.p.: 111–113° C.
FAB-MS (M+H)$^+$: 535 (theoretical value: 535)

3) Synthesis of Boc-Tyr(Br-Z)-D-Trp-Leu-OPac:

Boc-D-Trp-Leu-OPac (16.1 g) was dissolved in 10 N-HCl/dioxane (20 ml) and stirred for 30 minutes while cooling with ice. The solvent was removed by distillation, and the residue was dried in the presence of sodium hydroxide. This was dissolved in DMF (100 ml), and diisopropylethylamine (5.94 ml) and Boc-Tyr(Br-Z)-ONB (prepared from 17.8 g of Boc-Tyr(Br-Z)-OH, 7.53 g of HONB and 8.67 g of DCC) were added thereto and stirred overnight while cooling with ice. The solvent was removed by distillation, the residue was dissolved in AcOEt, and N,N-diisopropylethylamine (4.68 ml) was added thereto and stirred for 10 minutes. Water (300 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 0.5% methanol-chloroform) and obtained as a precipitate from chloroform-petroleum ether.

Yield: 25.8 g (94.4%)
$R_f$: 0.77
m.p.: 109.5–110.5° C.
Elementary analysis: as $C_{47}H_{51}N_4O_{10}Br$
Calculated: C, 61.91; H, 5.64; N, 6.14
Measured: C, 61.53; H, 5.70; N, 6.17

4) Synthesis of Boc-D-Lys($SO_2$Nap(1))-OH.CHA:

Boc-D-Lys-OH (2.00 g) was dissolved in dioxane (28 ml)-water (14 ml), and 1 N-NaOH (17.1 ml), and a dioxane solution (10 ml) of 1-naphthalenesulfonyl chloride (2.03 g) were dropwise added thereto and stirred while cooling with ice. The solvent was removed by distillation, the residue was dissolved in AcOEt (100 ml)-water (100 ml), 1 N-HCl was added to the resulting solution, while cooling with ice, to thereby make it acidic, and the AcOEt layer was separated. The AcOEt layer was washed with saturated saline solution (100 ml×2), dried with anhydrous sodium sulfate and concentrated. The resulting concentrate was dissolved in $CHCl_3$, cyclohexylamine (1.01 ml) was added thereto, and the solvent was removed by distillation. Petroleum ether was added to the residue, and the intended product was obtained as a precipitate.

Yield: 3.26 g (74.9%)
m.p.: 93.0–96.0 ° C.
FAB-MS (M+H)$^+$ (as Boc-D-Lys($SO_2$Nap(1))-OH): 436 (theoretical value: 436)

5) Synthesis of Boc-D-Lys($SO_2$Na(1))-Tyr(Br-Z)-D-Trp-Leu-OPac:

Boc-Tyr(Br-Z)-D-Trp-Leu-OPac (1.37 g) was dissolved in 10 N-HCl/dioxane (10 ml) and stirred for 30 minutes, while cooling with ice. The solvent was removed by distillation, and the residue was dried in the presence of sodium hydroxide.

This was dissolved in DMF (5 ml), and diisopropylethylamine (0.30 ml) and Boc-D-Lys($SO_2$Nap(1))-ONB (prepared from 964 mg of Boc-D-Lys($SO_2$Nap(1))-OH.CHA, 376 mg of HONB and 433 mg of DCC) were added thereto and stirred overnight while cooling with ice. The solvent was removed by distillation, the residue was dissolved in AcOEt, and N,N-diisopropylethylamine (0.24 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.72 g (93.2%)
$R_f$: 0.70
m.p.: 98.0–99.0° C.
Elementary analysis: as $C_{63}H_{69}N_6O_{13}BrS.0.25 H_2O$
Calculated: C, 61.28; H, 5.67; N, 6.81
Measured: C, 61.06; H, 5.94; N, 7.10

6) Synthesis of Boc-Arg(Tos)-D-Lys(SO$_2$Nap(1))-Tyr(Br-Z)-D-Trp-Leu-OPac:

Boc-D-Lys(SO$_2$Na(1))-Tyr(Br-Z)-D-Trp-Leu-OPac (1.60 g) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.26 ml) and Boc-Arg(Tos)-ONB (prepared from 972 mg of Boc-Arg(Tos)-OH.¼ H$_2$O.¾ AcOEt, 420 mg of HONB and 483 mg of DCC) were added thereto and stirred overnight while cooling with ice. The solvent was removed by distillation, the residue was dissolved in AcOEt, and N,N-diisopropylethylamine (0.26 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 1.35 g (67.4%)

$R_f$: 0.67 m.p.: 115.0–117.0° C.

Elementary analysis: as $C_{76}H_{87}N_{10}O_{16}BrS_2.H_2O$

Calculated: C, 58.57; H, 5.76; N, 8.99

Measured: C, 58.20; H, 5.70; N, 8.74

7) Synthesis of cyclo(-Arg-D-Lys(SO$_2$Nap(1))-Tyr-D-Trp-Leu-):

Boc-Arg(Tos)-D-Lys (SO$_2$Nap(1))-Tyr(Br-Z)-D-Trp-Leu-OPac (500 mg) was dissolved in 90%-acetic acid (20 ml), and Zn (1.06 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (117 mg) and DCC (135 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 33.5 mg (30.0%)

Amino acid analysis (after hydrolyzed in 6 N-HCl at 110° C. for 24 hours) (Parenthesized are the theoretical data.):

Leu 1.00 (1); Tyr 0.90 (1); Lys 0.19 (1); Arg 0.99 (1)

FAB-MS (M+H)$^+$: 937 (theoretical value: 937)

Example 2

Synthesis of cyclo(-Arg-D-Lys(COPh)-Tyr-D-Trp-Leu-)

1) Synthesis of Boc-Arg(Tos)-OBzl:

An aqueous solution (15 ml) of Cs$_2$CO$_3$ (2.93 mg) was dropwise added to a methanol (40 ml) solution of Boc-Arg(Tos)-OH.0.25 H$_2$O.0.75 AcOEt (10 g), and the solvent was removed by distillation under reduced pressure. DMF (60 ml) was added to the residue to form a solution, and a DMF (30 ml) solution of benzyl bromide (3.08 g) was dropwise added thereto and then directly stirred overnight. The solvent was removed by distillation under reduced pressure, and the residue was dissolved in AcOEt (200 ml). This was washed with aqueous 10%-citric acid solution, saturated saline solution, aqueous saturated sodium hydrogencarbonate solution and saturated saline solution, dried with anhydrous sodium sulfate and concentrated to obtain the intended product as an oily substance.

Yield: 8.72 g (93.2%)

$R_f$: 0.41

FAB-MS (M+H)$^+$: 518 (theoretical value: 518)

2) Synthesis of Boc-Leu-Arg(Tos)-OBzl:

Boc-Arg(Tos)-OBzl (7.77 g) was dissolved in 10 N-HCl/dioxane (30 ml) and stirred for 30 minutes, while cooling with ice. The solvent was removed by distillation, and the residue was dried in the presence of sodium hydroxide. This was dissolved in DMF (10 ml), and diisopropylethylamine (2.86 ml) and Boc-Leu-ONB (prepared from Boc-Leu-OH.H$_2$O (4.50 g), HONB (3.53 g) and DCC (4.06 g)) were added thereto and stirred overnight while cooling with ice. The DCU formed was removed by filtration, the resulting filtrate was concentrated, the resulting concentrate was dissolved in AcOEt (150 ml), and N,N-diisopropylethylamine (2.34 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from petroleum ether.

Yield: 8.86 g (93.5%)

$R_f$: 0.40 m.p.: 71.0–73.0° C.

Elementary analysis: as $C_{31}H_{45}N_5O_7S$

Calculated: C, 58.93; H, 7.18; N, 11.08

Measured: C, 58.54; H, 7.14; N, 11.03

3) Synthesis of Boc-Leu-Arg(Tos)-OPac:

Boc-Leu-Arg(Tos)-OBzl (8.86 g) was dissolved in methanol (500 ml) and then subjected to catalytic reduction in a hydrogen steam in the presence of a catalyst of 10%-Pd-carbon. After the catalyst was removed by filtration, the resulting filtrate was concentrated to 100 ml. To this was dropwise added an aqueous solution (15 ml) of Cs$_2$CO$_3$ (2.28 g). The solvent was removed by distillation, the residue was dissolved in DMF (30 ml), and a DMF (10 ml) solution of phenacyl bromide (2.79 g) was added thereto and stirred overnight. The solvent was removed by distillation, the residue was dissolved in AcOEt (150 ml), and this was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from diethyl ether.

Yield: 8.95 g (97.1%)

$R_f$: 0.39 m.p.: 78.0–81.0° C.

Elementary analysis: as $C_{32}H_{45}N_5O_8S$

Calculated: C, 58.25; H, 6.87; N, 10.61

Measured: C, 58.03; H, 6.92; N, 10.24

4) Synthesis of Boc-D-Trp-Leu-Arg(Tos)-OPac:

Boc-Leu-Arg(Tos)-Opac (8.95 g) was dissolved in 10 N-HCl/dioxane (100 ml) and stirred for 30 minutes, while cooling with ice. The solvent was removed by distillation, and the residue was dried in the presence of sodium hydroxide. This was dissolved in DMF (30 ml), and diisopropylethylamine (3.71 ml) and Boc-D-Trp-ONB (prepared from Boc-D-Trp-OH (4.69 g), HONB (3.01 g) and DCC (3.47 g) were added thereto and stirred overnight, while cooling with ice. The DCU formed was removed by filtration, the filtrate was concentrated, the resulting concentrate was dissolved in AcOEt (150 ml), and N,N-diisopropylethylamine (2.00 ml) was added thereto and stirred for 10 minutes. Water (150 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from petroleum ether.

Yield: 10.61 g (92.2%)

$R_f$: 0.25 m.p.: 109.0–111.0° C.

Elementary analysis: as $C_{43}H_{55}N_7O_9S.0.71\ H_2O$

Calculated: C, 60.08; H, 6.55; N, 11.41

Measured: C, 60.37; H, 6.66; N, 11.17

5) Synthesis of Boc-Tyr(Br-Z)-D-Trp-Leu-Arg(Tos)-OPac:

Boc-D-Trp-Leu-Arg(Tos)-OPac (10.11 g) was dissolved in 10 N-HCl/dioxane (100 ml) and stirred for 30 minutes, while cooling with ice. The solvent was removed by distillation, and the residue was dried in the presence of sodium hydroxide. This was dissolved in DMF (20 ml), and diisopropylethylamine (4.54 ml) and Boc-Tyr(Br-Z)-ONB (prepared from Boc-Tyr(Br-Z)-OH (7.40 g), HONB (2.92 g) and DCC (3.37 g)) were added thereto and stirred overnight while cooling with ice. The DCU formed was removed by filtration, the filtrate was concentrated, the resulting concentrate was dissolved in AcOEt (150 ml), and N,N-diisopropylethylamine (1.95 ml) was added thereto and stirred for 10 minutes. Water (150 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from petroleum ether.

Yield: 14.67 g (100%)

$R_f$: 0.23 m.p.: 115.0–117.0° C.

Elementary analysis: as $C_{60}H_{69}N_8O_{13}BrS.0.25\ H_2O$

Calculated: C, 58.75; H, 5.71; N, 9.13

Measured: C, 58.49; H, 5.59; N, 9.02

6) Synthesis of Boc-D-Lys(COPh)-OH.CHA:

Boc-D-Lys-OH (2.00 g) was dissolved in dioxane (28 ml)-water (14 ml), and 1 N-NaOH (17.1 ml), and a dioxane solution (10 ml) of benzoyl chloride (1.26 g) were dropwise added thereto and stirred while cooling with ice. The solvent was removed by distillation, the residue was dissolved in AcOEt (100 ml)-water (100 ml), 1 N-HCl was added to the resulting solution, while cooling with ice, to thereby make it acidic, and the AcOEt layer was separated. The AcOEt layer was washed with saturated saline solution (100 ml×2), dried with anhydrous sodium sulfate and concentrated. The resulting concentrate was dissolved in $CHCl_3$, cyclohexylamine (1.01 ml) was added thereto, and the solvent was removed by distillation. Petroleum ether was added to the residue, and the intended product was obtained as a precipitate.

Yield: 2.75 g (75.3%)

m.p.: 84.0–86.0° C.

FAB-MS (M+H)$^+$ (as Boc-D-Lys(COPh)-OH): 350 (theoretical value: 350)

7) Synthesis of Boc-D-Lys(COPh)-Tyr(Br-Z)-D-Trp-Leu-Arg(Tos)-OPac:

Boc-Tyr(Br-Z)-D-Trp-Leu-Arg(Tos)-OPac (1.38 g) was dissolved in 10 N-HCl/dioxane (20 ml) and stirred for 30 minutes, while cooling with ice. The solvent was removed by distillation, and the residue was dried in the presence of sodium hydroxide. This was dissolved in DMF (10 ml), and diisopropylethylamine (0.43 ml) and Boc-D-Lys (COPh)-ONB (prepared from Boc-D-Lys (COPh)-OH.CHA (611 mg), HONB (292 mg) and DCC (336 mg)) were added thereto and stirred overnight while cooling with ice. The solvent was removed by distillation, the residue was dissolved in AcOEt, and N,N-diisopropylethylamine (0.18 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 1% methanol-chloroform), and the intended product was obtained as a precipitate from chloroform-petroleum ether.

Yield: 950 mg (57.8%)

$R_f$: 0.63 m.p.: 111.0–114.0° C.

Elementary analysis: as $C_{73}H_{85}N_{10}O_{15}BrS.0.75\ H_2O$

Calculated: C, 59.73; H, 5.93; N, 9.54

Measured: C, 59.40; H, 6.16; N, 9.46

8) Synthesis of cyclo(-Arg-D-Lys(CoPh)-Tyr-D-Trp-Leu-):

Boc-D-Lys(COPh)-Tyr(Br-Z)-D-Trp-Leu-Arg(Tos)-OPac (400 mg) was dissolved in 90%-acetic acid (20 ml), and Zn (899 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (101 mg) and DCC (116 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (100 ml) solution of diisopropylethylamine (0.50 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 26.0 mg (32.7%)

Amino acid analysis (after hydrolyzed in 6 N-HCl at 110° C. for 24 hours) (Parenthesized are the theoretical data.):

Leu 1.00 (1); Tyr 0.93 (1); Lys 0.91 (1); Arg 1.02 (1)

FAB-MS (M+H)$^+$: 851 (theoretical value: 851)

Example 3

Synthesis of cyclo(-Arg-D-Lys(SO$_2$Nap(2))-Trp-D-Trp-Leu-)

1) Synthesis of Boc-D-Lys(SO$_2$Nap(2))-OH.CHA:

Boc-D-Lys-OH (2.00 g) was dissolved in dioxane (28 ml)-water (14 ml), and 1 N-NaOH (17.1 ml), and a dioxane solution (10 ml) of 2-naphthalenesulfonyl chloride (2.03 g) were dropwise added thereto and stirred while cooling with ice. The solvent was removed by distillation, the residue was dissolved in AcOEt (100 ml)-water (100 ml), 1 N-HCl was added to the resulting solution, while cooling with ice, to thereby make it acidic, and the AcOEt layer was separated. The AcOEt layer was washed with saturated saline solution (100 ml×2), dried with anhydrous sodium sulfate and concentrated. The resulting concentrate was dissolved in CHCl$_3$, cyclohexylamine (1.01 ml) was added thereto, and the solvent was removed by distillation. Petroleum ether was added to the residue, and the intended product was obtained as a precipitate.

Yield: 2.58 g (59.3%)

m.p.: 95.0–97.5° C.

FAB-MS (M+H)$^+$ (as Boc-D-Lys(SO$_2$Nap(2))-OH): 436 (theoretical value: 436)

2) Synthesis of Boc-D-Lys(SO$_2$Na(2))-Tyr(Br-Z)-D-Trp-Leu-Arg(Tos)-OPac:

Boc-Tyr(Br-Z)-D-Trp-Leu-Arg(Tos)-OPac (1.38 g) as obtained in Example 2–5) was dissolved in 10 N-HCl/dioxane (20 ml) and stirred for 30 minutes, while cooling with ice. The solvent was removed by distillation, the residue was dried in the presence of sodium hydroxide. This was dissolved in DMF (10 ml), and diisopropylethylamine (0.43 ml) and Boc-D-Lys(SO$_2$Nap(2))-ONB (prepared from Boc-D-Lys(SO$_2$Nap(2))-OH.CHA (729 mg), HONB (292 mg) and DCC (336 mg)) were added thereto and stirred overnight while cooling with ice. The solvent was removed by distillation, the residue was dissolved in AcOEt, and N,N-diisopropylethylamine (0.18 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 1% methanol-chloroform), and the intended product was obtained as a precipitate from chloroform-petroleum ether.

Yield: 1.39 g (79.8%)

R$_f$: 0.33 m.p.: 109.0–111.5° C.

Elementary analysis: as C$_{76}$H$_{87}$N$_{10}$O$_{16}$BrS$_2$.0.25 H$_2$O

Calculated: C, 59.08; H, 5.70; N, 9.07

Measured: C, 58.66; H, 5.86; N, 9.00

3) Synthesis of cyclo(-Arg-D-Lys(SO$_2$Nap(2))-Tyr-D-Trp-Leu-):

Boc-D-Lys(SO$_2$Nap(2))-Tyr(Br-Z)-D-Trp-Leu-Arg(Tos)-OPac (400 mg) was dissolved in 90%-acetic acid (20 ml), and Zn (899 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml).

The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (94 mg) and DCC (108 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (100 ml) solution of diisopropylethylamine (0.47 ml) and directly stirred overnight. The solvent was removed by distillation, the residue was washed for a total of two times with AcOEt (100 ml), and a pale yellow powder was obtained. The thus-obtained powder (40 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration.

Yield: 22.0 mg (27.1%)

Amino acid analysis (after hydrolyzed in 6 N-HCl at 110° C. for 24 hours) (Parenthesized are the theoretical data.):

Leu 1.00 (1); Tyr 0.90 (1); Lys 0.21 (1); Arg 0.94 (1)

FAB-MS (M+H)$^+$: 937 (theoretical value: 937)

Example 4

Synthesis of cyclo(-Arg-D-Trp-Tyr-D-Trp-Leu-)

1) Synthesis of Boc-D-Trp-Tyr(Br-Z)-D-Trp-Leu-Arg(Tos)-OPac:

Boc-Tyr(Br-Z)-D-Trp-Leu-Arg(Tos)-OPac (1.38 g) as obtained in Example 2–5) was dissolved in 10 N-HCl/dioxane (20 ml) and stirred for 30 minutes, while cooling with ice. The solvent was removed by distillation, and the residue was dried in the presence of sodium hydroxide. This was dissolved in DMF (10 ml), and diisopropylethylamine (0.43 ml) and Boc-D-Trp-ONB (prepared from Boc-D-Trp-OH (414 mg), HONB (292 mg) and DCC (336 mg)) were added thereto and stirred overnight while cooling with ice. The solvent was removed by distillation, the residue was dissolved in AcOEt, and N,N-diisopropylethylamine (0.18 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 1.45 g (91.0%)

$R_f$: 0.71 m.p.: 116.0–119.0° C.

Elementary analysis: as $C_{71}H_{79}N_{10}O_{14}BrS \cdot 0.25\ H_2O$

Calculated: C, 60.35; H, 5.67; N, 9.91

Measured: C, 60.11; H, 5.76; N, 9.92

2) Synthesis of cyclo(-Arg-D-Trp-Tyr-D-Trp-Leu-):

Boc-D-Trp-Tyr(Br-Z)-D-Trp-Leu-Arg(Tos)-OPac (500 mg) was dissolved in 90%-acetic acid (20 ml), and Zn (899 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (128 mg) and DCC (147 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (30 ml), then dropwise added to a DMF (320 ml) solution of diisopropylethylamine (0.64 ml) and directly stirred overnight. The solvent was removed by distillation, the residue was washed for a total of two times with AcOEt (100 ml), and a pale yellow powder was obtained. The thus-obtained powder (40 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration.

Yield: 11.0 mg (11.5%)

Amino acid analysis (after hydrolyzed in 6 N-HCl at 110° C. for 24 hours) (Parenthesized are the theoretical data.):

Leu 1.00 (1); Tyr 0.85 (1); Arg 0.95 (1)

FAB-MS $(M+H)^+$: 805 (theoretical value: 805)

Example 5

Synthesis of cyclo(-Arg-D-Lys-Tyr-D-Trp-Leu-)

1) Synthesis of Boc-D-Lys(Cl-Z)-Tyr(Br-Z)-D-Trp-Leu-Arg(Tos)-OPac:

Boc-Tyr(Br-Z)-D-Trp-Leu-Arg(Tos)-OPac (1.38 g) as obtained in Example 2–5) was dissolved in 10 N-HCl/dioxane (20 ml) and stirred for 30 minutes, while cooling with ice. The solvent was removed by distillation, and the residue was dried in the presence of sodium hydroxide. This was dissolved in DMF (10 ml), and diisopropylethylamine (0.43 ml) and Boc-D-Lys(Cl-Z)-ONB (prepared from Boc-D-Lys(Cl-Z)-OH.TBA (664 mg), HONB (283 mg) and DCC (326 mg)) were added thereto and stirred overnight while cooling with ice. The solvent was removed by distillation, the residue was dissolved in AcOEt, and N,N-diisopropylethylamine (0.1B ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 1% methanol-chloroform), and the intended product was obtained as a precipitate from chloroform-petroleum ether.

Yield: 1.54 g (89.7%)

$R_f$: 0.33

M.p.: 97.5–100.0° C.

Elementary analysis: as $C_{74}H_{86}N_{10}O_{16}ClBrS$

Calculated: C, 58.51; H, 5.71; N, 9.22

Measured: C, 58.59; H, 6.02; N, 9.27

2) Synthesis of cyclo(-Arg-D-Lys-Tyr-D-Trp-Leu-):

Boc-D-Lys(Cl-Z)-Tyr(Br-Z)-D-Trp-Leu-Arg(Tos)-OPac (500 mg) was dissolved in 90%-acetic acid (20 ml), and Zn (1.08 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml).

The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (117 mg) and DCC (135 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (30 ml), then dropwise added to a DMF (320 ml) solution of diisopropylethylamine (0.59 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration.

Yield: 9.6 mg (11.7%)

Amino acid analysis (after hydrolyzed in 6 N-HCl at 110° C. for 24 hours) (Parenthesized are the theoretical data.):

Leu 1.00 (1); Tyr 0.93 (1); Lys 0.97 (1); Arg 0.98 (1)

FAB-MS $(M+H)^+$: 747 (theoretical value: 747)

Example 6

Synthesis of cyclo(-Arg-D-Lys(COCH$_2$Ph)-Tyr-D-Trp-Leu-)

1) Synthesis of Boc-D-Lys(COCH$_2$Ph)-OH.CHA:

Boc-D-Lys-OH (2.00 g) was dissolved in dioxane (28 ml)-water (14 ml), and 1 N-NaOH (17.1 ml) and a dioxane solution (10 ml) of phenylacetyl chloride (1.38 g) were dropwise added thereto and stirred while cooling with ice. The solvent was removed by distillation, the residue was dissolved in AcOEt (100 ml)-water (100 ml), then 1 N-HCl was added to the resulting solution, while cooling with ice, to thereby make it acidic, and the AcOEt layer was separated. The AcOEt layer was washed with saturated saline solution (100 ml×2), dried with anhydrous sodium sulfate and concentrated. The resulting concentrate was dissolved in CHCl$_3$, then cyclohexylamine (1.01 ml) was added thereto, and the solvent was removed by distillation. Petroleum ether was added to the residue, and the intended product was obtained as a precipitate.

Yield: 1.35 g (35.9%)

m.p.: 102.0–104.5° C.

FAB-MS (M+H)$^+$ (as Boc-D-Lys(COCH$_2$Ph)-OH): 364 (theoretical value: 364)

2) Synthesis of Boc-D-Lys(COCH$_2$Ph)-Tyr(Br-Z)-D-Trp-Leu-OPac:

Boc-Tyr(Br-Z)-D-Trp-Leu-OPac (1.37 g) as obtained in Example 1–3) was dissolved in 10 N-HCl/dioxane (10 ml) and stirred for 30 minutes, while cooling with ice. The solvent was removed by distillation, and the residue was dried in the presence of sodium hydroxide.

This was dissolved in DMF (5 ml), and diisopropylethylamine (0.30 ml) and Boc-D-Lys(COCH$_2$Ph)-ONB (prepared from Boc-D-Lys(COCH$_2$Ph)-OH.CHA (835 mg), HONB (376 mg) and DCC (433 mg)) were added thereto and stirred overnight while cooling with ice. The solvent was removed by distillation, the residue was dissolved in AcOEt, and N,N-diisopropylethylamine (0.24 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.68 g (96.7%)

R$_f$: 0.64 m.p.: 122.0–124.0° C.

Elementary analysis: as C$_{61}$H$_{69}$N$_6$O$_{12}$Br

Calculated: C, 63.26; H, 6.01; N, 7.26

Measured: C, 62.89; H, 6.25; N, 7.37

3) Synthesis of Boc-Arg(Tos)-D-Lys(COCH$_2$Ph)-Tyr(Br-Z)-D-Trp-Leu-OPac:

Boc-D-Lys(COCH$_2$Ph)-Tyr(Br-Z)-D-Trp-Leu-OPac (1.51 g) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.26 ml) and Boc-Arg(Tos)-ONB (prepared from Boc-Arg(Tos)-OH.¼ H$_2$O.¾ AcOEt (972 mg), HONB (420 mg) and DCC (483 mg)) were added thereto and stirred overnight while cooling with ice. The solvent was removed by distillation, the residue was dissolved in AcOEt, and N,N-diisopropylethylamine (0.26 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 680 mg (35.6%)

R$_f$: 0.66 m.p.: 107.0–109.0° C.

Elementary analysis: as C$_{74}$H$_{87}$N$_{10}$O$_{15}$BrS.0.75 H$_2$O

Calculated: C, 59.97; H, 6.02; N, 9.45

Measured: C, 59.70; H, 5.98; N, 9.21

4) Synthesis of cyclo(-Arg-D-Lys(COCH$_2$Ph)-Tyr-D-Trp-Leu-):

Boc-Arg(Tos)-D-Lys(COCH$_2$Ph)-Tyr(Br-Z)-D-Trp-Leu-OPac (400 mg) was dissolved in 90%-acetic acid (20 ml), and Zn (1.06 g) was added thereto and stirred for 30 minutes.

Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (98 mg) and DCC (112 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.50 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 24.0 mg (30.6%)

Amino acid analysis (after hydrolyzed in 6 N-HCl at 110° C. for 24 hours) (Parenthesized are the theoretical data.):

Leu 1.00 (1); Tyr 0.92 (1); Lys 0.96 (1); Arg 0.95 (1)

FAB-MS (M+H)$^+$: 865 (theoretical value: 865)

Example 7

Synthesis of cyclo(-Arg-Lys(SO$_2$Nap(2))-Tyr-D-Trp-Leu-)

1) Synthesis of Boc-Lys(SO$_2$Nap(2))-OH.CHA:

Boc-Lys-OH (2.00 g) was dissolved in dioxane (28 ml)-water (14 ml), and 1 N-NaOH (17.1 ml) and a dioxane solution (10 ml) of 2-naphthalenesulfonyl chloride (2.03 g) were dropwise added thereto and stirred while cooling with ice. The solvent was removed by distillation, the residue was dissolved in AcOEt (100 ml)-water (100 ml), then 1 N-HCl was added to the resulting solution, while cooling with ice, to thereby make it acidic, and the AcOEt layer was separated. The AcOEt layer was washed with saturated saline solution (100 ml×2), dried with anhydrous sodium sulfate and concentrated. The resulting concentrate was dissolved in CHCl$_3$, then cyclohexylamine (1.01 ml) was added thereto, and the solvent was removed by distillation. Petroleum ether was added to the residue, and the intended product was obtained as a precipitate.

Yield: 2.67 g (61.4%)

m.p.: 99.0–102.0° C.

FAB-MS (M+H)$^+$ (as Boc-Lys(SO$_2$Nap(2))-OH): 436 (theoretical value: 436)

2) Synthesis of Boc-Lys(SO$_2$Na(1))-Tyr(Br-Z)-D-Trp-Leu-OPac:

Boc-Tyr(Br-Z)-D-Trp-Leu-OPac (1.37 g) as obtained in Example 1–3) was dissolved in 10 N-HCl/dioxane (10 ml) and stirred for 30 minutes, while cooling with ice. The solvent was removed by distillation, and the residue was dried in the presence of sodium hydroxide.

This was dissolved in DMF (5 ml), and diisopropylethylamine (0.30 ml) and Boc-Lys(SO$_2$Nap(2))-ONB (prepared from Boc-Lys(SO$_2$Nap(1))-OH.CHA (964 mg), HONB (376 mg) and DCC (433 mg)) were added thereto and stirred overnight while cooling with ice. The solvent was removed by distillation, the residue was dissolved in AcOEt, and N,N-diisopropylethylamine (0.24 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.87 g (100.0%)
R$_f$: 0.70
m.p.: 99.0–100.0° C.
Elementary analysis: as C$_{63}$H$_{69}$N$_6$O$_{13}$BrS.0.25 H$_2$O
Calculated: C, 61.28; H, 5.67; N, 6.80
Measured: C, 61.32; H, 6.15; N, 7.07

3) Synthesis of Boc-Arg(Tos)-Lys(SO$_2$Nap(2))-Tyr(Br-Z)-D-Trp-Leu-OPac:

Boc-Lys(SO$_2$Na(2))-Tyr(Br-Z)-D-Trp-Leu-OPac (1.60 g) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.26 ml) and Boc-Arg(Tos)-ONB (prepared from Boc-Arg(Tos)-OH.¼ H$_2$O.¾ AcOEt (972 mg), HONB (420 mg) and DCC (483 mg)) were added thereto and stirred overnight while cooling with ice. The solvent was removed by distillation, the residue was dissolved in AcOEt, and N,N-diisopropylethylamine (0.26 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 1.00 g (49.9%)
R$_f$: 0.67
m.p.: 110.0–112.0° C.
Elementary analysis: as C$_{76}$H$_{87}$N$_{10}$O$_{16}$BrS$_2$.0.5 H$_2$O
Calculated: C, 58.91; H, 5.72; N, 9.04
Measured: C, 58.61; H, 5.82; N, 8.78

4) Synthesis of cyclo(-Arg-Lys(SO$_2$Nap(2))-Tyr-D-Trp-Leu-):

Boc-Arg(Tos)-Lys(SO$_2$Nap(2))-Tyr(Br-Z)-D-Trp-Leu-OPac (500 mg) was dissolved in 90%-acetic acid (20 ml), and Zn (1.06 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (117 mg) and DCC (135 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 49.0 mg (48.3%)
Amino acid analysis (after hydrolyzed in 6 N-HCl at 110° C. for 24 hours) (Parenthesized are the theoretical data.):
Leu 1.00 (1); Tyr 0.90 (1); Lys 0.17 (1); Arg 0.96 (1)
FAB-MS (M+H)$^+$: 937 (theoretical value: 937)

Example 8

Synthesis of cyclo(-Arg-D-Glu(NHCH$_2$CH$_2$Ph)-Tyr-D-Trp-Leu-)

1) Synthesis of Boc-D-Glu(NHCH$_2$CH$_2$Ph)-OBzl:

HONB (0.73 g) and DCC (0.84 g) were added to an acetonitrile (80 ml) solution of Boc-D-Glu-OBzl (1.25 g), while cooling with ice, and then stirred at room temperature for 3 hours. The DCU formed was removed by filtration, and the resulting filtrate was added to an acetonitrile (50 ml) solution of b-phenethylamine (0.72 g) and then directly stirred for 11 hours. The solvent was removed by distillation, then the residue was suspended in AcOEt (50 ml) and water (30 ml), and 1 N-HCl (6 ml) was added to the resulting suspension, while stirring and cooling with ice, to thereby make it acidic. The AcOEt (50 ml) was separated and washed with water. Next, N,N-diisopropylethylamine (0.48 ml) was added to the AcOEt layer and stirred for 10 minutes. The AcOEt layer was washed with saturated saline solution, aqueous saturated sodium hydrogencarbonate solution and saturated saline solution, dried with anhydrous sodium sulfate and then concentrated. Petroleum ether was added to the resulting concentrate, and the intended product was obtained as a precipitate.

Yield: 1.59 g (97.5%)
m.p.: 89.0–90.0° C.
Elementary analysis: as C$_{25}$H$_{32}$N$_2$O$_5$
Calculated: C, 68.16; H, 7.32; N, 6.36
Measured: C, 68.13; H. 7.42; N, 6.60

2) Synthesis of Boc-D-Glu(NHCH$_2$CH$_2$Ph)-Tyr(Br-Z)-D-Trp-Leu-OPac:

Boc-D-Glu(NHCH$_2$CH$_2$Ph)-OBzl (793 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (376 mg) and DCC (433 mg) were added thereto and directly stirred for 5 hours, while cooling with ice (Boc-D-Glu(NHCH$_2$CH$_2$Ph)-ONB).

Boc-Tyr(Br-Z)-D-Trp-Leu-OPac (1.37 g) as obtained in Example 1–3) was dissolved in 10 N-HCl/dioxane (10 ml)

and stirred for 30 minutes, while cooling with ice. The solvent was removed by distillation, and the residue was dried in the presence of sodium hydroxide. This was dissolved in DMF (5 ml), and diisopropylethylamine (0.30 ml) and the previously-prepared Boc-D-Glu(NHCH$_2$CH$_2$Ph)-ONB were added thereto and stirred overnight while cooling with ice. The solvent was removed by distillation, the residue was dissolved in AcOEt, and N,N-diisopropylethylamine (0.24 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.04 g (60.6%)
$R_f$: 0.74
m.p.: 149.0–150.5° C.
Elementary analysis: as $C_{60}H_{67}N_6O_{12}Br \cdot 0.5\ H_2O$
Calculated: C, 62.50; H, 5.94; N, 7.29
Measured: C, 62.39; H, 5.94; N, 7.17

3) Synthesis of Boc-Arg(Tos)-D-Glu(NHCH$_2$CH$_2$Ph)-Tyr(Br-Z)-D-Trp-Leu-OPac:

Boc-D-Glu (NHCH$_2$CH$_2$Ph)-Tyr(Br-Z)-D-Trp-Leu-OPac (708 mg) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg (Tos)-ONB (prepared from Boc-Arg(Tos)-OH·¼ H$_2$O·¾ AcOEt (464 mg), HONB (200 mg) and DCC (230 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 3% methanol-chloroform), and the intended product was obtained as a precipitate from chloroform-petroleum ether.

Yield: 750 mg (83.3%)
$R_f$: 0.65
m.p.: 98.0–100.0 ° C.
Elementary analysis: as $C_{73}H_{85}N_{10}O_{15}BrS$
Calculated: C, 60.28; H, 5.89; N, 9.63
Measured: C, 60.22; H, 6.34; N, 9.54

4) Synthesis of cyclo(-Arg-D-Glu(NHCH$_2$CH$_2$Ph)-Tyr-D-Trp-Leu-):

Boc-Arg (Tos)-D-Glu (NHCH$_2$CH$_2$Ph)-Tyr(Br-Z)-D-Trp-Leu-OPac (400 mg) was dissolved in 90%-acetic acid (20 ml), and Zn (899 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (99 mg) and DCC (113 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 24.0 mg (30.9%)
Amino acid analysis (after hydrolyzed in 6 N-HCl at 110° C. for 24 hours) (Parenthesized are the theoretical data.):
Leu 1.00 (1); Tyr 0.93 (1); Glu 1.04 (1); Arg 0.93 (1)
FAB-MS (M+H)$^+$: 851 (theoretical value: 851)

Example 9

Synthesis of cyclo(-Arg-D-Glu(NHCH$_2$Ph)-Tyr-D-Trp-Leu-)

1) Synthesis of Boc-D-Glu(NHCH$_2$Ph)-OBzl:

HONB (0.73 g) and DCC (0.84 g) were added to an acetonitrile (80 ml) solution of Boc-D-Glu-OBzl (1.25 g), while cooling with ice, and then stirred at room temperature for 3 hours. The DCU formed was removed by filtration, and the resulting filtrate was added to an acetonitrile (50 ml) solution of benzylamine (0.63 g) and then directly stirred for 11 hours. The solvent was removed by distillation, then the residue was suspended in AcOEt (50 ml) and water (30 ml), and 1 N-HCl (6 ml) was added to the resulting suspension, while stirring and cooling with ice, to thereby make it acidic. The AcOEt (50 ml) was separated and washed with water. Next, N,N-diisopropylethylamine (0.48 ml) was added to the AcOEt layer and stirred for 10 minutes. The AcOEt layer was washed with saturated saline solution, aqueous saturated sodium hydrogencarbonate solution and saturated saline solution, dried with anhydrous sodium sulfate and then concentrated. Petroleum ether was added to the resulting concentrate, and the intended product was obtained as a precipitate.

Yield: 1.54 g (97.5%)
m.p.: 92.0–94.0° C.
Elementary analysis: as $C_{24}H_{30}N_2O_5$
Calculated: C, 67.59; H. 7.09; N, 6.57
Measured: C, 67.59; H, 7.05; N, 6.87

2) Synthesis of Boc-D-Glu(NHCH$_2$Ph)-Tyr(Br-Z)-D-Trp-Leu-OPac:

Boc-D-Glu(NHCH$_2$Ph)-OBzl (768 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (376 mg) and DCC (433 mg) were added thereto and directly stirred for 5 hours, while cooling with ice (Boc-D-Glu(NHCH$_2$Ph)-ONB).

Boc-Tyr(Br-Z)-D-Trp-Leu-OPac (1.37 g) as obtained in Example 1–3) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.30 ml) and the previously-prepared Boc-D-Glu(NHCH$_2$Ph)-ONB were added thereto and stirred overnight while cooling with ice. The solvent was removed by distillation, the residue was dissolved in AcOEt, and N,N-diisopropylethylamine (0.23 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.04 g (61.3%)
$R_f$: 0.77
m.p.: 139.0–140.0° C.
Elementary analysis: as $C_{59}H_{65}N_6O_{12}Br.0.5\ H_2O$
Calculated: C, 62.21; H, 5.84; N, 7.38
Measured: C, 62.19; H, 5.94; N, 7.39

3) Synthesis of Boc-Arg(Tos)-D-Glu(NHCH$_2$Ph)-Tyr(Br-Z)-D-Trp-Leu-OPac:

Boc-D-Glu(NHCH$_2$Ph)-Tyr(Br-Z)-D-Trp-Leu-OPac (700 mg) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg(Tos)-ONB (prepared from Boc-Arg(Tos)-OH.¼ H$_2$O.¾ AcOEt (464 mg), HONB (200 mg) and DCC (230 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 3% methanol-chloroform), and the intended product was obtained as a precipitate from chloroform-petroleum ether.

Yield: 710 mg (79.6%)
$R_f$: 0.57
m.p.: 102.0–104.0° C.
Elementary analysis: as $C_{72}H_{83}N_{10}O_{15}BrS$
Calculated: C, 60.04; H, 5.81; N, 9.72
Measured: C, 59.97; H, 6.18; N, 9.50

4) Synthesis of cyclo(-Arg-D-Glu(NHCH$_2$Ph)-Tyr-D-Trp-Leu-):

Boc-Arg(Tos)-D-Glu(NHCH$_2$Ph)-Tyr(Br-Z)-D-Trp-Leu-OPac (400 mg) was dissolved in 90%-acetic acid (20 ml), and Zn (908 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (100 mg) and DCC (115 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 21.0 mg (27.1%)
Amino acid analysis (after hydrolyzed in 6 N-HCl at 110° C. for 24 hours) (Parenthesized are the theoretical data.):
Leu 1.00 (1); Tyr 0.92 (1); Glu 1.02 (1); Arg 0.93 (1)
FAB-MS (M+H)$^+$: 837 (theoretical value: 837)

Example 10

Synthesis of cyclo(-Arg-D-Glu(NHCHPh$_2$)-Tyr-D-Trp-Leu-)

1) Synthesis of Boc-D-Glu(NHCHPh$_2$)-OBzl:

HONB (0.73 g) and DCC (0.84 g) were added to an acetonitrile (80 ml) solution of Boc-D-Glu-OBzl (1.25 g), while cooling with ice, and then stirred at room temperature for 3 hours. The DCU formed was removed by filtration, and the resulting filtrate was added to an acetonitrile (50 ml) solution of aminodiphenylmethanol (1.08 g) and then directly stirred for 11 hours. The solvent was removed by distillation, then the residue was suspended in AcOEt (50 ml) and water (30 ml), and 1 N-HCl (6 ml) was added to the resulting suspension, while stirring and cooling with ice, to thereby make it acidic. The AcOEt (50 ml) was separated and washed with water. Next, N,N-diisopropylethylamine (0.48 ml) was added to the AcOEt layer and stirred for 10 minutes. The AcOEt layer was washed with saturated saline solution, aqueous saturated sodium hydrogencarbonate solution and saturated saline solution, dried with anhydrous sodium sulfate and then concentrated. Petroleum ether was added to the resulting concentrate, and the intended product was obtained as a precipitate.

Yield: 1.88 g (100.0%)
m.p.: 130.0–131.5° C.
Elementary analysis: as $C_{30}H_{34}N_2O_5$
Calculated: C, 71.69; H, 6.82; N, 5.57
Measured: C, 71.36; H, 6.87; N, 5.67

2) Synthesis of Boc-D-Glu(NHCHPh$_2$)-Tyr(Br-Z)-D-Trp-Leu-OPac:

Boc-D-Glu(NHCHPh$_2$)-OBzl (905 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (376 mg) and DCC (433 mg) were added thereto and directly stirred for 5 hours, while cooling with ice (Boc-D-Glu(NHCHPh$_2$)-ONB).

Boc-Tyr(Br-Z)-D-Trp-Leu-OPac (1.37 g) as obtained in Example 1–3) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.30 ml) and the previously-prepared Boc-D-Glu(NHCHPh$_2$)-ONB were added thereto and stirred overnight while cooling with ice. The solvent was removed by distillation, the residue was dissolved in AcOEt, and N,N-diisopropylethylamine (0.23 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.14 g (63.0%)
R$_f$: 0.82
m.p.: 131.0–133.0° C.
Elementary analysis: as C$_{65}$H$_{69}$N$_6$O$_{12}$Br
Calculated: C, 64.73; H, 5.77; N, 6.97
Measured: C, 64.51; H, 5.89; N, 6.96

3) Synthesis of Boc-Arg(Tos)-D-Glu(NHCHPh$_2$)-Tyr(Br-Z)-D-Trp-Leu-OPac:

Boc-D-Glu(NHCHPh$_2$)-Tyr(Br-Z)-D-Trp-Leu-OPac (700 mg) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg (Tos)-ONB (prepared from Boc-Arg(Tos)-OH.¼ H$_2$O.¾ AcOEt (464 mg), HONB (200 mg) and DCC (230 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 3% methanol-chloroform), and the intended product was obtained as a precipitate from chloroform-petroleum ether.

Yield: 950 mg (100.0%)
R$_f$: 0.57
m.p.: 108.0–110.0° C.
Elementary analysis: as C$_{78}$H$_{87}$NO$_{10}$O$_{15}$BrS.H$_2$O
Calculated: C, 61.05; H, 5.84; N. 9.12
Measured: C, 61.28; H, 6.23; N, 8.84

4) Synthesis of cyclo(-Arg-D-Glu(NHCHPh$_2$)-Tyr-D-Trp-Leu-):

Boc-Arg(Tos)-D-Glu(NHCHPh$_2$)-Tyr(Br-Z)-D-Trp-Leu-OPac (400 mg) was dissolved in 90%-acetic acid (20 ml), and Zn (862 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (95 mg) and DCC (109 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.50 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 21.0 mg (26.1%)
Amino acid analysis (after hydrolyzed in 6 N-HCl at 110° C. for 24 hours) (Parenthesized are the theoretical data.):
Leu 1.00 (1); Tyr 0.93 (1); Glu 1.22 (1); Arg 1.08 (1)
FAB-MS (M+H)$^+$: 913 (theoretical value: 913)

Example 11

Synthesis of cyclo(-Arg-D-Glu(NHCH$_2$Nap(1))-Tyr-D-Trp-Leu-)

1) Synthesis of Boc-D-Glu(NHCH$_2$Nap(1))-OBzl:

HONB (0.73 g) and DCC (0.84 g) were added to an acetonitrile (80 ml) solution of Boc-D-Glu-OBzl (1.25 g), while cooling with ice, and then stirred at room temperature for 3 hours. The DCU formed was removed by filtration, and the resulting filtrate was added to an acetonitrile (50 ml) solution of 1-naphthalenemethylamine (0.93 g) and then directly stirred for 11 hours. The solvent was removed by distillation, then the residue was suspended in AcOEt (50 ml) and water (30 ml), and 1 N-HCl (6 ml) was added to the resulting suspension, while stirring and cooling with ice, to thereby make it acidic. The AcOEt (50 ml) was separated and washed with water. Next, N,N-diisopropylethylamine (0.48 ml) was added to the AcOEt layer and stirred for 10 minutes. The AcOEt layer was washed with saturated saline solution, aqueous saturated sodium hydrogencarbonate solution and saturated saline solution, dried with anhydrous sodium sulfate and then concentrated. Petroleum ether was added to the resulting concentrate, and the intended product was obtained as a precipitate.

Yield: 1.76 g (98.7%)
m.p.: 99.0–100.5° C.
Elementary analysis: as C$_{28}$H$_{32}$N$_2$O$_5$
Calculated: C, 70.57; H, 6.77; N, 5.88
Measured: C, 70.47; H, 6.82; N, 5.73

2) Synthesis of Boc-D-Glu(NHCH$_2$Nap(1))-Tyr(Br-Z)-D-Trp-Leu-OPac:

Boc-D-Glu(NHCH$_2$Nap(1))-OBzl (858 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (376 mg) and DCC (433 mg) were added thereto and directly stirred for 5 hours, while cooling with ice (Boc-D-Glu(NHCH$_2$Nap(1))-ONB).

Boc-Tyr(Br-Z)-D-Trp-Leu-OPac (1.37 g) as obtained in Example 1–3) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.30 ml) and the previously-prepared Boc-D-Glu(NHCH$_2$Nap(1))-ONB were added thereto and stirred overnight while cooling with ice. The solvent was removed by distillation, the residue was dissolved in AcOEt, and N,N-diisopropylethylamine (0.23 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 770 mg (43.5%)
$R_f$: 0.63
m.p.: 122.0–124.0° C.
Elementary analysis: as $C_{63}H_{67}N_6O_{12}Br.0.5\ H_2O$
Calculated: C, 63.63; H, 5.76; N, 7.02
Measured: C, 63.55; H, 5.83; N, 6.94

3) Synthesis of Boc-Arg(Tos)-D-Glu(NHCH$_2$Nap(1))-Tyr(Br-Z)-D-Trp-Leu-OPac:

Boc-D-Glu(NHCH$_2$Nap(1))-Tyr(Br-Z)-D-Trp-Leu-OPac (730 mg) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg(Tos)-ONB (prepared from Boc-Arg(Tos)-OH.¼ H$_2$O.¾ AcOEt (464 mg), HONB (200 mg) and DCC (230 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 3% methanol-chloroform), and the intended product was obtained as a precipitate from chloroform-petroleum ether.

Yield: 920 mg (99.7%)
$R_f$: 0.58
m.p.: 109.0–112.0° C.
Elementary analysis: as $C_{76}H_{85}N_{10}O_{15}BrS.0.75\ H_2O$
Calculated: C, 60.09; H, 5.79; N, 9.31
Measured: C, 61.00; H, 6.20; N, 9.00

4) Synthesis of cyclo(-Arg-D-Glu(NHCH$_2$Nap(1))-Tyr-D-Trp-Leu-):

Boc-Arg(Tos)-D-Glu(NHCH$_2$Nap(1))-Tyr(Br-Z)-D-Trp-Leu-OPac (400 mg) was dissolved in 90%-acetic acid (20 ml), and Zn (877 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (96 mg) and DCC (111 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.49 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 45.0 mg (56.7%)
Amino acid analysis (after hydrolyzed in 6 N-HCl at 110° C. for 24 hours) (Parenthesized are the theoretical data.):
Leu 1.00 (1); Tyr 0.93 (1); Glu 1.04 (1); Arg 0.97 (1)
FAB-MS (M+H)$^+$: 887 (theoretical value: 887)

Example 12

Synthesis of cyclo(-Arg-D-Glu(Php)-Tyr-D-Trp-Leu-)

1) Synthesis of Boc-D-Glu(Php)-OBzl:

HONB (0.73 g) and DCC (0.84 g) were added to an acetonitrile (80 ml) solution of Boc-D-Glu-OBzl (1.25 g), while cooling with ice, and then stirred at room temperature for 3 hours. The DCU formed was removed by filtration, and the resulting filtrate was added to an acetonitrile (50 ml) solution of phenylpiperazine (0.96 g) and then directly stirred for 11 hours. The solvent was removed by distillation, then the residue was suspended in AcOEt (50 ml) and water (30 ml), and 1 N-HCl (6 ml) was added to the resulting suspension, while stirring and cooling with ice, to thereby make it acidic. The AcOEt (50 ml) was separated and washed with water. Next, N,N-diisopropylethylamine (0.48 ml) was added to the AcOEt layer and stirred for 10 minutes. The AcOEt layer was washed with saturated saline solution, aqueous saturated sodium hydrogencarbonate solution and saturated saline solution, dried with anhydrous sodium sulfate and then concentrated. Petroleum ether was added to the resulting concentrate, and the intended product was obtained as a precipitate.

Yield: 1.70 g (95.4%)
m.p.: 138.0–140.0° C.
Elementary analysis: as $C_{27}H_{35}N_3O_5$
Calculated: C, 67.34; H, 7.33; N, 8.73
Measured: C, 67.28; H, 7.43; N, 8.83

2) Synthesis of Boc-D-Glu(Php)-Tyr(Br-Z)-D-Trp-Leu-OPac:

Boc-D-Glu(Php)-OBzl (867 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (376 mg) and DCC (433 mg)

were added thereto and directly stirred for 5 hours, while cooling with ice (Boc-D-Glu(Php)-ONB).

Boc-Tyr(Br-Z)-D-Trp-Leu-OPac (1.37 g) as obtained in Example 1–3) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.30 ml) and the previously-prepared Boc-D-Glu(Php)-ONB were added thereto and stirred overnight while cooling with ice. The solvent was removed by distillation, the residue was dissolved in AcOEt, and N,N-diisopropylethylamine (0.23 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 880 mg (45.9%)
$R_f$: 0.80
m.p.: 99.0–100.0° C.
Elementary analysis: as $C_{62}H_{70}N_7O_{12}Br \cdot 0.75 H_2O$
Calculated: C, 62.12; H, 6.01; N, 8.18
Measured: C, 61.87; H, 5.84; N, 7.87

3) Synthesis of Boc-Arg(Tos)-D-Glu(Php)-Tyr(Br-Z)-D-Trp-Leu-OPac:

Boc-D-Glu(Php)-Tyr(Br-Z)-D-Trp-Leu-OPac (734 mg) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg(Tos)-ONB (prepared from Boc-Arg(Tos)-OH·¼ $H_2O$·¾ AcOEt (464 mg), HONB (200 mg) and DCC (230 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 3% methanol-chloroform), and the intended product was obtained as a precipitate from chloroform-petroleum ether.

Yield: 910 mg (98.2%)
$R_f$: 0.50
m.p.: 111.0–113.5° C.
Elementary analysis: as $C_{75}H_{88}N_{11}O_{15}BrS \cdot 0.88 H_2O$
Calculated: C, 59.60; H, 5.99; N, 10.19
Measured: C, 59.93; H, 6.46; N, 9.77

4) Synthesis of cyclo(-Arg-D-Glu(Php)-Tyr-D-Trp-Leu-):

Boc-Arg(Tos)-D-Glu(Php)-Tyr(Br-Z)-D-Trp-Leu-OPac (400 mg) was dissolved in 90%-acetic acid (20 ml), and Zn (874 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (96 mg) and DCC (110 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.49 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 57.0 mg (71.7%)
Amino acid analysis (after hydrolyzed in 6 N-HCl at 110° C. for 24 hours) (Parenthesized are the theoretical data.):
Leu 1.00 (1); Tyr 0.92 (1); Glu 0.98 (1); Arg 0.92 (1)
FAB-MS $(M+H)^+$: 892 (theoretical value: 892)

Example 13

Synthesis of cyclo(-Arg-D-Glu(Bzlp)-Tyr-D-Trp-Leu-)

1) Synthesis of Boc-D-Glu(Bzlp)-OBzl:

HONB (0.73 g) and DCC (0.84 g) were added to an acetonitrile (80 ml) solution of Boc-D-Glu-OBzl (1.25 g), while cooling with ice, and then stirred at room temperature for 3 hours. The DCU formed was removed by filtration, and the resulting filtrate was added to an acetonitrile (50 ml) solution of benzylpiperazine (1.30 g) and then directly stirred for 11 hours. The solvent was removed by distillation, then the residue was suspended in AcOEt (50 ml) and water (30 ml), and 1 N-HCl (8 ml) was added to the resulting suspension, while stirring and cooling with ice, to thereby make it acidic. The AcOEt (50 ml) was separated and washed with water. Next, N,N-diisopropylethylamine (0.48 ml) was added to the AcOEt layer and stirred for 10 minutes. The AcOEt layer was washed with saturated saline solution, aqueous saturated sodium hydrogencarbonate solution and saturated saline solution, dried with anhydrous sodium sulfate and then concentrated. Petroleum ether was added to the resulting concentrate, and the intended product was obtained as a precipitate.

Yield: 1.61 g (87.8%)
m.p.: 118.0–119.0° C.
Elementary analysis: as $C_{28}H_{37}N_3O_5$
Calculated: C, 67.86; H, 7.52; N, 8.48
Measured: C, 67.56; H, 7.57; N, 8.34

2) Synthesis of Boc-D-Glu(Bzlp)-Tyr(Br-Z)-D-Trp-Leu-OPac:

Boc-D-Glu(Bzlp)-OBzl (893 mg) was dissolved in dioxane (50 ml), and 1 N-NaOH (2.0 ml) was added thereto and stirred for 30 minutes while cooling with ice. The solvent was removed by distillation, then the residue was suspended in AcOEt (50 ml) and water (30 ml), and 1 N-HCl (8 ml) was added to the resulting suspension, while stirring and cooling with ice, to thereby make it acidic. The aqueous layer was separated and washed with AcOEt (50 ml). The AcOEt layers were combined, washed with saturated saline solution (100 ml), dried with anhydrous sodium sulfate and dried. Then, the solvent was removed by distillation under reduced pressure. DMF (10 ml) was added to the residue to dissolve it. HONB (376 mg) and DCC (433 mg) were added thereto and directly stirred for 5 hours, while cooling with ice (Boc-D-Glu(Bzlp)-ONB).

Boc-Tyr(Br-Z)-D-Trp-Leu-OPac (1.37 g) as obtained in Example 1–3) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.30 ml) and the previously-prepared Boc-D-Glu(Bzlp)-ONB were added thereto and stirred overnight while cooling with ice. The solvent was removed by distillation, the residue was dissolved in AcOEt, and N,N-diisopropylethylamine (0.23 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.34 g (74.5%)
$R_f$: 0.58
m.p.: 102.0–104.0° C.
Elementary analysis: as $C_{63}H_{72}N_7O_{12}Br$
Calculated: C, 63.10; H, 6.05; N, 8.18
Measured: C, 62.92; H, 6.26; N, 8.10

3) Synthesis of Boc-Arg(Tos)-D-Glu(Bzlp)-Tyr(Br-Z)-D-Trp-Leu-OPac:

Boc-D-Glu(Bzlp)-Tyr(Br-Z)-D-Trp-Leu-OPac (742 mg) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg(Tos)-ONB (prepared from Boc-Arg(Tos)-OH.¼ $H_2O$.¾ AcOEt (464 mg), HONB (200 mg) and DCC (230 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 1.07 g (100.0%)
$R_f$: 0.55
m.p.: 112.0–114.0° C.
Elementary analysis: as $C_{76}H_{90}N_{11}O_{15}BrS.H_2O$
Calculated: C, 59.75; H, 6.07; N, 10.09
Measured: C, 59.33; H, 6.03; N, 10.00

4) Synthesis of cyclo(-Arg-D-Glu(Bzlp)-Tyr-D-Trp-Leu-):

Boc-Arg(Tos)-D-Glu(Bzlp)-Tyr(Br-Z)-D-Trp-Leu-OPac (500 mg) was dissolved in 90%-acetic acid (20 ml), and Zn (1.09 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (119 mg) and DCC (128 mg) were added thereto while cooling with ice and then stirred at room temperature for 2 hours. The DCU formed was removed, and the solvent was removed by distillation. Next, 10 N-HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 21.6 mg (21.6%)
Amino acid analysis (after hydrolyzed in 6 N-HCl at 110° C. for 24 hours) (Parenthesized are the theoretical data.):
Leu 1.00 (1); Tyr 0.92 (1); Glu 0.98 (1); Arg 0.91 (1)
FAB-MS $(M+H)^+$: 906 (theoretical value: 906)

Example 14

Synthesis of cyclo(-Arg-D-Glu((2)-Pyp)-Tyr-D-Trp-Leu-)

1) Synthesis of Boc-D-Glu((2)-Pyp)-OBzl:

HONB (0.73 g) and DCC (0.84 g) were added to an acetonitrile (80 ml) solution of Boc-D-Glu-OBzl (1.25 g), while cooling with ice, and then stirred at room temperature for 3 hours. The DCU formed was removed by filtration, and the resulting filtrate was added to an acetonitrile (50 ml) solution of 2-pyridylpiperazine (1.13 g) and then directly stirred for 11 hours. The solvent was removed by distillation, then the residue was dissolved in AcOEt (100 ml), and N,N-diisopropylethylamine (0.48 ml) was added thereto and stirred for 10 minutes. The AcOEt layer was washed with 1 N-HCl, saturated saline solution, aqueous saturated sodium hydrogencarbonate solution and saturated saline solution, dried with anhydrous sodium sulfate and then concentrated. Petroleum ether was added to the resulting concentrate, and the intended product was obtained as a precipitate.

Yield: 1.30 g (72.8%)
m.p.: 137.0–138.5° C.
Elementary analysis: as $C_{26}H_{34}N_4O_5.0.75\ H_2O$
Calculated: C, 62.94; H, 7.21; N, 11.29
Measured: C, 62.86; H, 7.05; N, 11.21

2) Synthesis of Boc-D-Glu((2)-Pyp)-Tyr(Br-Z)-D-Trp-Leu-OPac:

Boc-D-Glu((2)-Pyp)-OBzl (869 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (376 mg) and DCC (433 mg) were added thereto and directly stirred for 5 hours, while cooling with ice (Boc-D-Glu((2)-Pyp)-ONB).

Boc-Tyr(Br-Z)-D-Trp-Leu-OPac (1.37 g) as obtained in Example 1–3) was dissolved in 10 N-HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.30 ml) and the previously-prepared Boc-D-Glu((2)-Pyp)-ONB were added thereto and stirred overnight while cooling with ice. The solvent was removed by distillation, the residue was dissolved in AcOEt, and N,N-diisopropylethylamine (0.23 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.30 g (73.1%)
$R_f$: 0.66
m.p.: 107.0–110.0° C.
Elementary analysis: as $C_{61}H_{69}N_8O_{12}Br$
Calculated: C, 61.77; H, 5.86; N, 9.45
Measured: C, 61.68; H, 6.12; N, 9.17

3) Synthesis of Boc-Arg(Tos)-D-Glu((2)-Pyp)-Tyr(Br-Z)-D-Trp-Leu-OPac:

Boc-D-Glu((2)-Pyp)-Tyr(Br-Z)-D-Trp-Leu-OPac (734 mg) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg(Tos)-ONB (prepared from Boc-Arg(Tos)-OH.4/5 AcOEt (464 mg), HONB (200 mg) and DCC (230 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 930 mg (100.0%)
$R_f$: 0.62
m.p.: 116.0–118.0° C.
Elementary analysis: as $C_{74}H_{87}N_{12}O_{15}BrS.H_2O$. Calculated: C, 58.69; H, 5.92; N, 11.10. Measured: C, 58.52; H, 6.00; N, 10.85.

4) Synthesis of cyclo(-Arg-D-Glu((2)-Pyp)-Tyr-D-Trp-Leu-):

Boc-Arg(Tos)-D-Glu((2)-Pyp)-Tyr(Br-Z)-D-Trp-Leu-OPac (500 mg) was dissolved in 90%-acetic acid (20 ml), and Zn (1.09 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (119 mg) and DCC (128 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 12.0 mg (12.1%)
Amino acid analysis (after hydrolyzed in 6 N—HCl at 110° C. for 24 hours) (Parenthesized are the theoretical data.): Leu 1.00 (1); Tyr 0.92 (1); Glu 0.99 (1); Arg 0.93 (1).
FAB-MS $(M+H)^+$: 893 (theoretical value: 893)

Example 15

Synthesis of cyclo(-Arg-D-Glu((2)-MeOPhp)-Tyr-D-Trp-Leu-)

1) Synthesis of Boc-D-Glu((2)-MeOPhp)-OBzl:

HONB (0.73 g) and DCC (0.84 g) were added to an acetonitrile (80 ml) solution of Boc-D-Glu-OBzl (1.25 g), while cooling with ice, and then stirred at room temperature for 3 hours. The DCU formed was removed by filtration, and the resulting filtrate was added to an acetonitrile (50 ml) solution of 2-methoxyphenylpiperazine (854 mg) and then directly stirred for 11 hours. The solvent was removed by distillation, then the residue was dissolved in AcOEt (50 ml), and N,N-diisopropylethylamine (0.48 ml) was added thereto and stirred for 10 minutes. The AcOEt layer was washed with 1 N—HCl, saturated saline solution, aqueous saturated sodium hydrogencarbonate solution and saturated saline solution, dried with anhydrous sodium sulfate and then concentrated, to obtain the intended product as an oily substance.

Yield: 1.90 g (100.0%)
FAB-MS $(M+H)^+$: 511 (theoretical value: 511)

2) Synthesis of Boc-D-Glu((2)-MeOPhp)-Tyr(Br-Z)-D-Trp-Leu-OPac:

Boc-D-Glu((2)-MeOPhp)-OBzl (921 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (376 mg) and DCC (433 mg) were added thereto and directly stirred for 5 hours, while cooling with ice (Boc-D-Glu((2)-MeOPhp)-ONB).

Boc-Tyr(Br-Z)-D-Trp-Leu-OPac (1.37 g) as obtained in Example 1-3) was dissolved in 10 N—HCl/dioxane (10 ml)

and stirred for 30 minutes, while cooling with ice. The solvent was removed by distillation, and the residue was dried in the presence of sodium hydroxide. This was dissolved in DMF (5 ml), and diisopropylethylamine (0.30 ml) and the previously-prepared Boc-D-Glu((2)-MeOPhp)-ONB were added thereto and stirred overnight while cooling with ice. The solvent was removed by distillation, the residue was dissolved in AcOEt, and N,N-diisopropylethylamine (0.23 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 780 mg (42.8%)
$R_f$: 0.70
m.p.: 92.0–94.0° C.
Elementary analysis: as $C_{63}H_{72}N_7O_{13}Br \cdot 0.5\ H_2O$. Calculated: C, 61.84; H, 6.09; N, 8.01. Measured: C, 61.97; H, 6.40; N, 8.15.

3) Synthesis of Boc-Arg(Tos)-D-Glu((2)-MeOPhp)-Tyr(Br-Z)-D-Trp-Leu-OPac:

Boc-D-Glu((2)-MeOPhp)-Tyr(Br-Z)-D-Trp-Leu-OPac (752 mg) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg(Tos)-ONB (prepared from Boc-Arg(Tos)-OH.4/5 AcOEt (464 mg), HONB (200 mg) and DCC (230 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 950 mg (100.0%)
$R_f$: 0.54
m.p.: 112.0–114.0° C.
FAB-MS $(M+H)^+$: 1525 (theoretical value: 1525)

4) Synthesis of cyclo(-Arg-D-Glu((2)-MeOPhp)-Tyr-D-Trp-Leu-):

Boc-Arg(Tos)-D-Glu((2)-MeOPhp)-Tyr(Br-Z)-D-Trp-Leu-OPac (500 mg) was dissolved in 90%-acetic acid (20 ml), and Zn (1.09 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (119 mg) and DCC (128 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 9.3 mg (9.20%)
Amino acid analysis (after hydrolyzed in 6 N—HCl at 110° C. for 24 hours) (Parenthesized are the theoretical data.): Leu 1.00 (1); Tyr 0.90 (1); Glu 1.01 (1); Arg 0.93 (1).
FAB-MS $(M+H)^+$: 922 (theoretical value: 922)

Example 16

Synthesis of cyclo(-Arg-D-Glu((4)-MeOPhp)-Tyr-D-Trp-Leu-)

1) Synthesis of Boc-D-Glu((4)-MeOPhp)-OBzl:

HONB (0.73 g) and DCC (0.84 g) were added to an acetonitrile (80 ml) solution of Boc-D-Glu-OBzl (1.25 g), while cooling with ice, and then stirred at room temperature for 3 hours. The DCU formed was removed by filtration, and the resulting filtrate was added to an acetonitrile (50 ml) solution of 2-methoxyphenylpiperazine (854 mg) and then directly stirred for 11 hours. The solvent was removed by distillation, then the residue was dissolved in AcOEt (50 ml), and N,N-diisopropylethylamine (0.48 ml) was added thereto and stirred for 10 minutes. The AcOEt layer was washed with 1 N—HCl, saturated saline solution, aqueous saturated sodium hydrogencarbonate solution and saturated saline solution, dried with anhydrous sodium sulfate and then concentrated, to obtain the intended product as an oily substance.

Yield: 1.90 g (100.0%)
FAB-MS $(M+H)^+$: 511 (theoretical value: 511)

2) Synthesis of Boc-D-Glu((4)-MeOPhp)-Tyr(Br-Z)-D-Trp-Leu-OPac:

Boc-D-Glu((4)-MeOPhp)-OBzl (921 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (376 mg) and DCC (433 mg) were added thereto and directly stirred for 5 hours, while cooling with ice (Boc-D-Glu((4)-MeOPhp)-ONB).

Boc-Tyr(Br-Z)-D-Trp-Leu-OPac (1.37 g) as obtained in Example 1-3) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.30 ml) and the previously-prepared Boc-D-Glu((4)-MeOPhp)-ONB were added thereto and stirred overnight while cooling with ice. The solvent was removed by distillation, the residue was dissolved in AcOEt, and N,N- diisopropylethylamine (0.23 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.24 g (68.9%)

$R_f$: 0.70 m.p.: 96.0–98.0° C.

Elementary analysis: as $C_{63}H_{72}N_7O_{13}Br$. Calculated: C, 62.27; H, 5.97; N, 8.07. Measured: C, 61.94; H, 6.27; N, 8.03.

3) Synthesis of Boc-Arg(Tos)-D-Glu((4)-MeOPhp)-Tyr(Br-Z)-D-Trp-Leu-OPac:

Boc-D-Glu((4)-MeOPhp)-Tyr(Br-Z)-D-Trp-Leu-OPac (752 mg) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg(Tos)-ONB (prepared from Boc-Arg(Tos)-OH.4/5 AcOEt (464 mg), HONB (200 mg) and DCC (230 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 950 mg (100.0%)

$R_f$: 0.53 m.p.: 115.0–117.0° C.

Elementary analysis: as $C_{76}H_{90}N_{11}O_{16}BrS.0.5\ H_2O$. Calculated: C, 59.58; H, 5.97; N, 10.04. Measured: C, 59.10; H, 6.26; N, 9.82.

4) Synthesis of cyclo(-Arg-D-Glu((4)-MeOPhp)-Tyr-D-Trp-Leu-):

Boc-Arg(Tos)-D-Glu((4)-MeOPhp)-Tyr(Br-Z)-D-Trp-Leu-OPac (500 mg) was dissolved in 90%-acetic acid (20 ml), and Zn (1.09 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (119 mg) and DCC (128 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 24.6 mg (24.4%)

Amino acid analysis (after hydrolyzed in 6 N—HCl at 110° C. for 24 hours) (Parenthesized are the theoretical data.): Leu 1.00 (1); Tyr 0.90 (1); Glu 1.02 (1); Arg 0.92 (1).

FAB-MS $(M+H)^+$: 922 (theoretical value: 922)

Example 17

Synthesis of cyclo(-Arg-Glu(Php)-Tyr-D-Trp-Leu-)

1) Synthesis of Boc-Glu(Php)-OBzl:

HONB (0.73 g) and DCC (0.84 g) were added to an acetonitrile (80 ml) solution of Boc-Glu-OBzl (1.25 g), while cooling with ice, and then stirred at room temperature for 3 hours. The DCU formed was removed by filtration, and the resulting filtrate was added to an acetonitrile (50 ml) solution of phenylpiperazine (0.96 g) and then directly stirred for 11 hours. The solvent was removed by distillation, then the residue was dissolved in AcOEt (100 ml), and N,N-diisopropylethylamine (0.48 ml) was added thereto and stirred for 10 minutes. The AcOEt layer was washed with 1 N—HCl, saturated saline solution, aqueous saturated sodium hydrogencarbonate solution and saturated saline solution, dried with anhydrous sodium sulfate and then concentrated. Petroleum ether was added to the resulting concentrate, and the intended product was obtained as a precipitate.

Yield: 1.60 g (89.8%)

m.p.: 140.0–141.5° C.

Elementary analysis: as $C_{27}H_{35}N_3O_5$. Calculated: C, 67.34; H, 7.33; N, 8.73. Measured: C, 67.28; H, 7.43; N, 8.83.

2) Synthesis of Boc-Glu(Php)-Tyr(Br-Z)-D-Trp-Leu-OPac:

Boc-Glu(Php)-OBzl (867 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (376 mg) and DCC (433 mg) were added thereto and directly stirred for 5 hours, while cooling with ice (Boc-Glu(Php)-ONB).

Boc-Tyr(Br-Z)-D-Trp-Leu-OPac (1.37 g) as obtained in Example 1-3) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.30 ml) and the previously-prepared Boc-Glu(Php)-ONB were added thereto and stirred overnight while cooling with ice. The solvent was removed by distillation, the residue was dissolved in AcOEt, and N,N-diisopropylethylamine (0.23 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.23 g (69.2%)

$R_f$: 0.70 m.p.: 95.0–98.0° C.

Elementary analysis: as $C_{62}H_{70}N_7O_{12}Br$. Calculated: C, 62.83; H, 5.95; N, 8.27. Measured: C, 62.59; H, 6.14; N, 8.18.

3) Synthesis of Boc-Arg(Tos)-Glu(Php)-Tyr(Br-Z)-D-Trp-Leu-O Pac:

Boc-Glu(Php)-Tyr(Br-Z)-D-Trp-Leu-OPac (734 mg) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg(Tos)-ONB (prepared from Boc-Arg(Tos)-OH.4/5 AcOEt (464 mg), HONB (200 mg) and DCC (230 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 930 mg (100.0%)

m.p.: 110.0–112.0° C.

Elementary analysis: as $C_{75}H_{88}N_{11}O_{15}BrS.0.25\ H_2O$. Calculated: C, 60.05; H, 5.95; N, 10.27. Measured: C, 59.65; H, 6.06; N, 9.97.

4) Synthesis of cyclo(-Arg-Glu(Php)-Tyr-D-Trp-Leu-):

Boc-Arg(Tos)-Glu(Php)-Tyr(Br-Z)-D-Trp-Leu-OPac (500 mg) was dissolved in 90%-acetic acid (20 ml), and Zn (874 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (119 mg) and DCC (128 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 22.5 mg (22.7%)

Amino acid analysis (after hydrolyzed in 6 N—HCl at 110° C. for 24 hours) (Parenthesized are the theoretical data.): Leu 1.00 (1); Tyr 0.91 (1); Glu 0.99 (1); Arg 0.91 (1).

FAB-MS $(M+H)^+$: 892 (theoretical value: 892)

Example 18

Synthesis of cyclo(-Lys-D-Glu(Php)-Tyr-D-Trp-Leu-)

1) Synthesis of Boc-Lys(Cl-Z)-D-Glu(Php)-Tyr(Br-Z)-D-Trp-Leu-OPac:

Boc-D-Glu(Php)-Tyr(Br-Z)-D-Trp-Leu-OPac (734 mg) as produced in Example 12-2) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Lys(Cl-Z)-ONB (prepared from Boc-Lys(Cl-Z)-OH (309 mg), HONB (155 mg) and DCC (179 mg)) were added thereto and stirred overnight while cooling with ice. The solvent was removed by distillation, the residue was dissolved in AcOEt, and N,N-diisopropylethylamine (0.12 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 920 mg (100.0%)

$R_f$: 0.68 m.p.: 99.0–101.0° C.

Elementary analysis: as $C_{76}H_{87}N_9O_{15}BrCl$. Calculated: C, 61.60; H, 5.92; N, 8.51. Measured: C, 61.65; H, 6.22; N, 8.64.

2) Synthesis of cyclo(-Lys-D-Glu(Php)-Tyr-D-Trp-Leu-):

Boc-Lys(Cl-Z)-D-Glu(Php)-Tyr(Br-Z)-D-Trp-Leu-OPac (500 mg) was dissolved in 90%-acetic acid (20 ml), and Zn (1.10 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (121 mg) and DCC (139 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 22.8 mg (23.5%)

Amino acid analysis (after hydrolyzed in 6 N—HCl at 110° C. for 24 hours) (Parenthesized are the theoretical data.): Leu 1.00 (1); Tyr 0.91 (1); Glu 1.00 (1); Arg 0.94 (1).

FAB-MS $(M+H)^+$: 864 (theoretical value: 864)

Example 19

Synthesis of cyclo(-Arg-D-Lys($COCH_2CH_2CH_2Ph$)-Tyr-D-Trp-Leu-)

1) Synthesis of Boc-D-Lys($COCH_2CH_2CH_2Ph$)-OH:

HONB (430 mg) and DCC (495 mg) were added to a DMF (20 ml) solution of 4-phenyl-n-butyric acid (381 mg) and then directly stirred for 11 hours, while cooling with ice ($PhCH_2CH_2CH_2CONB$).

Diisopropylethylamine (0.40 ml) and the previously-prepared $PhCH_2CH_2CH_2CONB$ were added to a DMF (15 ml) solution of Boc-D-Lys-OH (2.00 g) and then directly stirred for 11 hours, while cooling with ice. The solvent was removed by distillation, the residue was dissolved in AcOEt (100 ml)-water (100 ml), and 0.1 N—HCl was added to the resulting solution, while cooling with ice, to make it acidic. Then, the AcOEt layer was separated. The thus-separated AcOEt layer was washed with saturated saline solution (100 ml×2), dried with anhydrous sodium sulfate and concentrated, and the thus-obtained oily product was directly used in the next step 2) without being purified.

2) Synthesis of Boc-D-Lys($COCH_2CH_2CH_2Ph$)-Tyr(Br-Z)-D-Trp-Leu-Arg(Tos)-OPac:

Boc-Tyr(Br-Z)-D-Trp-Leu-Arg(Tos)-OPac (800 mg) as produced in Example 2-5) was dissolved in 10 N—HCl/dioxane (20 ml) and stirred for 30 minutes, while cooling with ice. The solvent was removed by distillation, and the residue was dried in the presence of sodium hydroxide. This was dissolved in DMF (10 ml), and diisopropylethylamine (0.13 ml) and Boc-D-Lys($COCH_2CH_2CH_2Ph$)-ONB (prepared from Boc-D-Lys($COCH_2CH_2CH_2Ph$)-OH obtained in the previous step 1), HONB (358 mg) and DCC (413 mg)) were added thereto and stirred overnight while cooling with ice. The solvent was removed by distillation, the residue was dissolved in AcOEt, and N,N-diisopropylethylamine (0.26 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 720 mg (73.4%)

$R_f$: 0.45 m.p.: 112.0–115.0° C.

Elementary analysis: as $C_{76}H_{91}N_{10}O_{15}BrS \cdot 0.17\ H_2O$.
Calculated: C, 60.51; H, 6.17; N, 9.28. Measured: C, 60.89; H, 6.57; N, 9.49.

3) Synthesis of cyclo(-Arg-D-Lys($COCH_2CH_2CH_2Ph$)-Tyr-D-Trp-Leu-):

Boc-D-Lys ($COCH_2CH_2CH_2Ph$)-Tyr (Br-Z)-D-Trp-Leu-Arg(Tos)-O Pac (500 mg) was dissolved in 90%-acetic acid (20 ml), and Zn (1.09 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (140 mg) and DCC (161 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (100 ml) solution of diisopropylethylamine (0.50 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 28.5 mg (28.7%)

Amino acid analysis (after hydrolyzed in 6 N—HCl at 110° C. for 24 hours) (Parenthesized are the theoretical data.): Leu 1.00 (1); Tyr 0.90 (1); Lys 0.93 (1); Arg 0.95 (1).

FAB-MS $(M+H)^+$: 893 (theoretical value: 893)

Example 20

Synthesis of cyclo(-Arg-D-Lys($COCH_2CH_2CH_2CH_2CH_2Ph$)-Tyr-D-Trp-Leu-)

1) Synthesis of Boc-D-Lys($COCH_2CH_2CH_2CH_2CH_2Ph$)-OH:

HONB (430 mg) and DCC (495 mg) were added to a DMF (20 ml) solution of 6-phenylhexanoic acid (423 mg) and then directly stirred for 11 hours, while cooling with ice ($PhCH_2CH_2CH_2CH_2CH_2CONB$).

Diisopropylethylamine (0.40 ml) and the previously-prepared $PhCH_2CH_2CH_2CH_2CH_2CONB$ were added to a DMF (15 ml) solution of Boc-D-Lys-OH (2.00 g) and then directly stirred for 11 hours, while cooling with ice. The solvent was removed by distillation, the residue was dissolved in AcOEt (100 ml)-water (100 ml), and 0.1 N—HCl was added to the resulting solution, while cooling with ice, to thereby make it acidic. Then, the AcOEt layer was separated. The thus-separated AcOEt layer was washed with saturated saline solution (100 ml×2), dried with anhydrous sodium sulfate and concentrated, and the thus-obtained oily product was directly used in the next step 2) without being purified.

2) Synthesis of Boc-D-Lys(COCH$_2$CH$_2$CH$_2$CH$_2$CH$_2$Ph)-Tyr(Br-Z)-D-Trp-Leu-Arg(Tos)-OPac:

Boc-Tyr(Br-Z)-D-Trp-Leu-Arg(Tos)-OPac (800 mg) as produced in Example 2-5) was dissolved in 10 N—HCl/dioxane (20 ml) and stirred for 30 minutes, while cooling with ice. The solvent was removed by distillation, and the residue was dried in the presence of sodium hydroxide. This was dissolved in DMF (10 ml), and diisopropylethylamine (0.13 ml) and Boc-D-Lys (COCH$_2$CH$_2$CH$_2$CH$_2$CH$_2$Ph)-ONB (prepared from Boc-D-Lys (COCH$_2$CH$_2$CH$_2$CH$_2$CH$_2$Ph)-OH obtained in the previous step 1), HONB (358 mg) and DCC (413 mg)) were added thereto and stirred overnight while cooling with ice. The solvent was removed by distillation, the residue was dissolved in AcOEt, and N,N-diisopropylethylamine (0.26 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 820 mg (80.1%)

R$_f$: 0.59 m.p.: 107.0–110.0° C.

FAB-MS (M+H)$^+$: 1524 (theoretical value: 1524)

3) Synthesis of cyclo (-Arg-D-Lys(COCH$_2$CH$_2$CH$_2$CH$_2$CH$_2$Ph)-Tyr-D-Trp-Leu-):

Boc-D-Lys (COCH$_2$CH$_2$CH$_2$CH$_2$CH$_2$Ph)-Tyr(Br-Z)-D-Trp-Leu-Arg(Tos)-OPac (500 mg) was dissolved in 90%-acetic acid (20 ml), and Zn (1.07 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (140 mg) and DCC (161 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (100 ml) solution of diisopropylethylamine (0.50 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 27.0 g (26.8%)

Amino acid analysis (after hydrolyzed in 6 N—HCl at 110° C. for 24 hours) (Parenthesized are the theoretical data.): Leu 1.00 (1); Tyr 0.90 (1); Lys 0.93 (1); Arg 0.92 (1).

FAB-MS (M+H)$^+$: 921 (theoretical value: 921)

Example 21

Synthesis of cyclo(-Arg-D-Glu(NHCH$_2$CH$_2$Ph)-Lys(COPh)-D-Trp-Leu-)

1) Synthesis of Boc-Lys(COPh)-OH.CHA:

Boc-Lys-OH (2.00 g) was dissolved in dioxane (28 ml)-water (14 ml), and 1 N-NaOH (17.1 ml) and a dioxane solution (10 ml) of benzoyl chloride (1.26 g) were dropwise added thereto and stirred while cooling with ice. The solvent was removed by distillation, the residue was dissolved in AcOEt (100 ml)-water (100 ml), then 1 N—HCl was added to the resulting solution, while cooling with ice, to thereby make it acidic, and the AcOEt layer was separated. The AcOEt layer was washed with saturated saline solution (100 ml×2), dried with anhydrous sodium sulfate and concentrated. The resulting concentrate was dissolved in CHCl$_3$, then cyclohexylamine (1.01 ml) was added thereto, and the solvent was removed by distillation. Petroleum ether was added to the residue, and the intended product was obtained as a precipitate.

Yield: 2.16 g (59.2%)

m.p.: 92.0–95.5° C.

FAB-MS (M+H)$^+$(as Boc-Lys(COPh)-OH): 350 (theoretical value: 350)

2) Synthesis of Boc-Lys(COPh)-D-Trp-Leu-OPac:

Boc-D-Trp-Leu-OPac (1.07 g) was dissolved in 10 N—HCl/dioxane (15 ml) and stirred for 30 minutes, while cooling with ice. The solvent was removed by distillation, and the residue was dried in the presence of sodium hydroxide. This was dissolved in DMF (100 ml), and diisopropylethylamine (0.44 ml) and Boc-Lys(COPh)-ONB (prepared from Boc-Lys(COPh)-OH.CHA (1.08 g) obtained in the previous step 1), HONB (466 mg) and DCC (537 mg)) were added thereto and stirred overnight while cooling with ice. The solvent was removed by distillation, the residue was dissolved in AcOEt, and N,N-diisopropylethylamine (4.68 ml) was added thereto and stirred for 10 minutes. Water (300 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.53 g (100.0%)

R$_f$: 0.58 m.p.: 91.0–93.0° C.

Elementary analysis: as C$_{43}$H$_{53}$N$_5$O$_8$.0.75H$_2$O. Calculated: C, 66.09; H, 7.03; N, 8.96. Measured: C, 66.42; H, 7.34; N, 8.82.

3) Synthesis of Boc-D-Glu(NHCH$_2$CH$_2$Ph)-Lys(COPh)-D-Trp-Leu-OPac:

Boc-D-Glu(NHCH$_2$CH$_2$Ph)-OBzl (793 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (387 mg) and DCC (446 mg) were added thereto and directly stirred for 5 hours, while cooling with ice (Boc-D-Glu(NHCH$_2$CH$_2$Ph)-ONB).

Boc-Lys(COPh)-D-Trp-Leu-OPac (1.34 g) prepared in the previous step 2) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.35 ml) and the previously-prepared Boc-D-Glu(NHCH$_2$CH$_2$Ph)-ONB were added thereto and stirred overnight while cooling with ice. The solvent was removed by distillation, the residue was dissolved in AcOEt, and N,N-diisopropylethylamine (0.32 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.24 g (70.8%)
R$_f$: 0.50
m.p.: 202.0–204.5° C.
Elementary analysis: as C$_{56}$H$_{69}$N$_7$O$_{10}$. Calculated: C, 67.25; H, 6.95; N, 9.80. Measured: C, 66.95; H, 6.89; N, 9.74.

4) Synthesis of Boc-Arg(Tos)-D-Glu(NHCH$_2$CH$_2$Ph)-Lys(COPh)-D-Trp-Leu-OPac:

Boc-D-Glu (NHCH$_2$CH$_2$Ph)-Lys (COPh)-D-Trp-Leu-OPac (1.14 g) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.23 ml) and Boc-Arg(Tos)-ONB (prepared from Boc-Arg(Tos)-OH.3/5 AcOEt.1/5 H$_2$O (829 mg), HONB (306 mg) and DCC (353 mg)) were added thereto and stirred overnight while cooling with ice. The solvent was removed by distillation, the residue was dissolved in AcOEt, and N,N-diisopropylethylamine (0.22 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 2% methanol-chloroform), and the intended product was obtained as a precipitate from chloroform-petroleum ether.

Yield: 1.44 g (96.3%)
R$_f$: 0.37
m.p.: 125.0–128.0° C.
Elementary analysis: as C$_{69}$H$_{87}$N$_{11}$O$_{13}$S.1.5H$_2$O. Calculated: C, 61.95; H, 6.78; N, 11.52. Measured: C, 61.74; H, 6.56; N, 11.47.

5) Synthesis of cyclo(-Arg-D-Glu(NHCH$_2$CH$_2$Ph)-Lys(COPh)-D-Trp-Leu-):

Boc-Arg (Tos)-D-Glu (NHCH$_2$CH$_2$Ph)-Lys (COPh)-D-Trp-Leu-OPac (500 mg) was dissolved in 90%-acetic acid (20 ml), and Zn (1.25 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (140 mg) and DCC (161 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (100 ml) solution of diisopropylethylamine (0.70 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 67.5 mg (57.6%)
Amino acid analysis (after hydrolyzed in 6 N—HCl at 110° C. for 24 hours) (Parenthesized are the theoretical data.): Leu 1.00 (1); Lys 0.84 (1); Glu 0.92 (1); Arg 0.83 (1).
FAB-MS (M+H)$^+$: 920 (theoretical value: 920)

Example 22

Synthesis of cyclo(-Arg-D-Glu(NHCH$_2$CH$_2$Ph)-Asp(NHCH$_2$Ph)-D-Trp-Leu-)

1) Synthesis of Boc-Asp(NHCH$_2$Ph)-OBzl:

HONB (0.73 g) and DCC (0.84 g) were added to an acetonitrile (80 ml) solution of Boc-Asp-OBzl(1.20 g), while cooling with ice, and then stirred at room temperature for 3 hours. The DCU formed was removed by filtration, and the resulting filtrate was added to an acetonitrile (50 ml) solution of benzylamine (0.43 g) and then directly stirred for 11 hours.

The solvent was removed by distillation, then the residue was dissolved in AcOEt (100 ml), and N,N-diisopropylethylamine (0.48 ml) was added thereto and stirred for 10 minutes. Water (100 ml) was added to this to separate the AcOEt layer, which was then washed with saturated saline solution, aqueous saturated sodium hydrogencarbonate solution and saturated saline solution, dried with anhydrous sodium sulfate and then concentrated. Petroleum ether was added to the resulting concentrate, and the intended product was obtained as a precipitate.

Yield: 1.54 g (100.0%)
m.p.: 123.0–125.0° C.
Elementary analysis: as C$_{23}$H$_{28}$N$_2$O$_5$. Calculated: C, 66.97; H, 6.84; N, 6.79. Measured: C, 67.39; H, 6.95; N, 7.17.

2) Synthesis of Boc-Asp(NHCH$_2$Ph)-D-Trp-Leu-OPac:

Boc-Asp(NHCH$_2$Ph)-OBzl (990 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (466 mg) and DCC (537 mg) were added thereto and directly stirred for 5 hours, while cooling with ice (Boc-Asp(NHCH$_2$Ph)-ONB). Boc-D-Trp-Leu-OPac (1.07 g) was dissolved in 10 N—HCl/dioxane (15 ml) and stirred for 30 minutes, while cooling with ice. The solvent was removed by distillation, and the residue was dried in the presence of sodium hydroxide. This was dissolved in DMF (100 ml), and diisopropylethylamine (0.44 ml) and the previously-prepared Boc-Asp (NHCH$_2$Ph)-ONB were added thereto and stirred overnight while cooling with ice. The solvent was removed by distillation, the residue was dissolved in AcOEt, and N,N-diisopropylethylamine (0.32 ml) was added thereto and stirred for 10 minutes. Water (300 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.35 g (91.0%)
R$_f$: 0.57
m.p.: 100.0–103.0° C.
Elementary analysis: as C$_{41}$H$_{49}$N$_5$O$_8$.H$_2$O. Calculated: C, 64.98; H, 6.78; N, 9.24. Measured: C, 64.68; H, 6.89; N, 9.21.

3) Synthesis of Boc-D-Glu(NHCH$_2$CH$_2$Ph)-Asp (NHCH$_2$Ph)-D-Trp-Leu-OPac:

Boc-D-Glu(NHCH$_2$CH$_2$Ph)-OBzl (793 mg) was dissolved in methanol (100 ml) and stirred for 1 hour in a hydrogen stream in the presence of 10%-Pd-C. The catalyst was removed by filtration, and then the solvent was removed by distillation under reduced pressure. DMF (10 ml) was added to the residue to dissolve it. HONB (387 mg) and DCC (446 mg) were added thereto and directly stirred for 5 hours, while cooling with ice (Boc-D-Glu(NHCH$_2$CH$_2$Ph)-ONB).

Boc-Asp(NHCH$_2$Ph)-D-Trp-Leu-OPac (1.29 g) as produced in the previous step 2) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.38 ml) and the previously-prepared Boc-D-Glu(NHCH$_2$CH$_2$Ph)-ONB were added thereto and stirred overnight while cooling with ice. The solvent was removed by distillation, the residue was dissolved in AcOEt, and N,N-diisopropylethylamine (0.24 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 3% methanol-chloroform), and the intended product was obtained as a precipitate from chloroform-petroleum ether.

Yield: 360 mg (21.1%)
R$_f$: 0.24
m.p.: 165.0–168.0° C.
Elementary analysis: as C$_{54}$H$_{65}$N$_7$O$_{10}$.0.75 H$_2$O. Calculated: C, 65.80; H, 6.80; N, 9.94. Measured: C, 65.59; H, 6.69; N, 10.21.

4) Synthesis of Boc-Arg(Tos)-D-Glu(NHCH$_2$CH$_2$Ph)-Asp (NHCH$_2$Ph)-D-Trp-Leu-OPac:

Boc-D-Glu (NHCH$_2$CH$_2$Ph)-Asp (NHCH$_2$Ph)-D-Trp-Leu-OPac (350 mg) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml) and diisopropylethylamine (0.39 ml) and Boc-Arg(Tos)-ONB (prepared from Boc-Arg(Tos)-OH.3/5 AcOEt.1/5 H$_2$O (359 mg), HONB (146 mg) and DCC (167 mg)) were added thereto and stirred overnight while cooling with ice. The solvent was removed by distillation, the residue was dissolved in AcOEt, and N,N-diisopropylethylamine (0.10 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. The intended product was obtained as a precipitate from chloroform-petroleum ether.

Yield: 410 mg (91.3%)
R$_f$: 0.39
m.p.: 148.0–150.0° C.
Elementary analysis: as C$_{67}$H$_{83}$N$_{11}$O$_{13}$.2.5 H$_2$O. Calculated: C, 60.60; H, 6.68; N, 11.60. Measured: C, 60.70; H, 6.57; N, 11.88.

5) Synthesis of cyclo(-Arg-D-Glu(NHCH$_2$CH$_2$Ph)-Asp (NHCH$_2$Ph)-D-Trp-Leu-):

Boc-Arg (Tos)-D-Glu (NHCH$_2$CH$_2$Ph)-Asp (NHCH$_2$Ph)-D-Trp-Leu-O Pac (360 mg) was dissolved in 90%-acetic acid (20 ml), and Zn (1.28 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (140 mg) and DCC (161 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (100 ml) solution of diisopropylethylamine (0.70 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 5.6 mg (6.72%)
Amino acid analysis (after hydrolyzed in 6 N—HCl at 110° C. for 24 hours) (Parenthesized are the theoretical data.): Leu 1.00 (1); Asp 0.63 (1); Glu 1.05 (1); Arg 0.96 (1).
FAB-MS (M+H)$^+$: 892 (theoretical value: 892)

Example 23

Synthesis of cyclo(-D-Tyr-Arg-D-Trp-Leu-D-Lys (SO$_2$Nap(1))-)

1) Synthesis of Boc-Arg(Tos)-D-Trp-Leu-OPac

Boc-D-Trp-Leu-OPac (2.14 g) as produced in Example 1-2) was dissolved in 10 N—HCl/dioxane (15 ml) and stirred for 30 minutes, while cooling with ice. The solvent was removed by distillation, and the residue was dried in the presence of sodium hydroxide. This was dissolved in DMF (15 ml), and diisopropylethylamine (0.79 ml) and Boc-Arg(Tos)-ONB (prepared from Boc-Arg(Tos)-OH.3/4 AcOEt.1/4 H$_2$O (3.59 g), HONB (1.58 g) and DCC (1.82 g)) were added thereto and stirred overnight while cooling with ice. The solvent was removed by distillation, the residue was dissolved in AcOEt, and N,N-diisopropylethylamine (0.94 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. The intended product was obtained as a precipitate from chloroform-petroleum ether.

Yield: 3.37 g (100.0%)
R$_f$: 0.53
m.p.: 94.0–96.5° C.
Elementary analysis: as C$_{43}$H$_{55}$N$_7$O$_9$S.0.5 H$_2$O
Calculated: C, 60.40; H, 6.60; N, 11.47. Measured: C, 60.13; H, 6.81; N, 11.52.

2) Synthesis of Boc-D-Tyr(Br-Z)-Arg(Tos)-D-Trp-Leu-OPac:

Boc-Arg(Tos)-D-Trp-Leu-OPac (1.69 g) was dissolved in 10 N—HCl/dioxane (15 ml) and stirred for 30 minutes, while cooling with ice. The solvent was removed by distillation, and the residue was dried in the presence of sodium hydroxide. This was dissolved in DMF (100 ml), and diisopropylethylamine (0.79 ml) and Boc-D-Tyr(Br-Z)-ONB (prepared from Boc-D-Tyr(Br-Z)-OH (1.09 g), HONB (430 mg) and DCC (495 mg)) were added thereto and stirred overnight while cooling with ice. The solvent was removed by distillation, the residue was dissolved in AcOEt, and N,N-diisopropylethylamine (0.29 ml) was added thereto and stirred for 10 minutes. Water (300 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 2.09 g (93.7%)
R$_f$: 0.62
m.p.: 105.0–107.5° C.
Elementary analysis: as C$_{60}$H$_{69}$N$_8$O$_{13}$BrS.2.5 H$_2$O. Calculated: C, 56.86; H, 5.58; N, 8.84. Measured: C, 56.52; H, 5.76; N, 8.88.

3) Synthesis of Boc-D-Lys(SO$_2$Nap(1))-D-Tyr(Br-Z)-Arg(Tos)-D-Trp-Leu-OPac:

Boc-D-Tyr(Br-Z)-Arg(Tos)-D-Trp-Leu-OPac (800 mg) was dissolved in 10 N—HCl/dioxane (10 ml) and stirred for 30 minutes, while cooling with ice. The solvent was removed by distillation, and the residue was dried in the presence of sodium hydroxide.

This was dissolved in DMF (5 ml), and diisopropylethylamine (0.26 ml) and Boc-D-Lys(SO$_2$Nap(1))-ONB (prepared from Boc-D-Lys(SO$_2$Nap(1))OH.CHA(643 mg) obtained in Example 1-4), HONB (251 mg) and DCC (289 mg)) were added thereto and stirred overnight while cooling with ice. The solvent was removed by distillation, the residue was dissolved in AcOEt, and N,N-diisopropylethylamine (0.16 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. The intended product was obtained as a precipitate from chloroform-petroleum ether.

Yield: 0.99 g (98.1%)
R$_f$: 0.65
m.p.: 112.0–115.0° C.
Elementary analysis: as C$_{76}$H$_{87}$N$_{10}$O$_{16}$BrS$_2$.Calculated: C, 59.25; H, 5.69; N, 9.09. Measured: C, 58.95; H, 6.08; N, 9.09.

4) Synthesis of cyclo(-D-Tyr-Arg-D-Trp-Leu-D-Lys (SO$_2$Nap(1))-):

Boc-D-Lys (SO$_2$Nap(1))-D-Tyr(Br-Z)-Arg(Tos)-D-Trp-Leu-OPac (530 mg) was dissolved in 90%-acetic acid (20 ml), and Zn (1.12 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (123 mg) and DCC (142 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (100 ml) solution of diisopropylethylamine (0.62 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 58.5 mg (54.3%)
Amino acid analysis (after hydrolyzed in 6 N—HCl at 110° C. for 24 hours) (Parenthesized are the theoretical data.): Leu 1.00 (1); Tyr 1.03 (1); Lys (0.20 (1); Arg 0.99 (1).
FAB-MS (M+H)$^+$: 937 (theoretical value: 937)

Example 24

Synthesis of cyclo(-D-Leu-Lys(SO$_2$Nap(1))-D-Tyr-Arg-D-Trp-)

1) Synthesis of H-D-Leu-OBzl.HCl:

An aqueous solution (50 ml) of Cs$_2$CO$_3$ (16.29 g) was dropwise added to a methanol (500 ml)-water (50 ml) solution of Boc-D-Leu-OH.H$_2$O (24.93 g). The solvent was removed by distillation, and the residue was dissolved in DMF (50 ml). A DMF (30 ml) solution of benzyl bromide (17.1 g) was added thereto and stirred overnight. Then, the solvent was removed by distillation, and the residue was dissolved in AcOEt (500 ml), washed with saturated saline solution, aqueous saturated sodium hydrogencarbonate solution and saturated saline solution, dried with anhydrous sodium sulfate and concentrated, to obtain an oily product.

10 N—HCl/dioxane (300 ml) was added to this and stirred for 30 minutes, while cooling with ice. The solvent was removed by distillation, and the residue was dried in the presence of sodium hydroxide. Then, the intended product was obtained as a precipitate from chloroform-petroleum ether.

The product obtained herein was directly used in the next step 2), without being purified.

2) Synthesis of Boc-D-Trp-D-Leu-OPac

H-D-Leu-OBzl.HCl (5.16 g) was dissolved in acetonitrile (200 ml) and cooled with ice, and diisopropylethylamine (3.96 ml) and Boc-D-Trp-ONB (prepared from Boc-D-Trp-OH (6.69 g), HONB (4.30 g) and DCC (4.95 g)) were added thereto and stirred overnight. The DCU formed was removed by filtration, the resulting filtrate was concentrated, and the concentrate was dissolved in AcOEt (500 ml). Next, N,N-diisopropylethylamine (10.0 ml) was added to the resulting solution and stirred for 10 minutes. Water (500 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was dissolved in methanol (500 ml) and then subjected to catalytic reduction in a hydrogen stream in the presence of a catalyst of 10%-Pd-carbon. After the reduction, the catalyst used was removed by filtration, the resulting filtrate was concentrated to 50 ml, and an aqueous solution (10 ml) of $Cs_2CO_3$ (3.26 g) was dropwise added thereto. The solvent was removed by distillation, the residue was dissolved in DMF (30 ml), and a DMF (30 ml) solution of phenacyl bromide (3.98 g) was added thereto and stirred overnight. The solvent was removed by distillation, the residue was dissolved in AcOEt (300 ml). Then, the resulting solution was washed with aqueous 10%-citric acid solution, saturated saline solution, aqueous saturated sodium hydrogencarbonate solution and saturated saline solution, dried with anhydrous sodium sulfate and concentrated. The intended product was obtained as a precipitate from chloroform-petroleum ether. The thus-obtained product was directly used in the next step 3) without being purified.

Yield: 9.53 g (89.0%)

$R_f$: 0.81 m.p.: 111–113° C.

Elementary analysis: as $C_{30}H_{37}N_3O_6$. Calculated: C, 67.27; H, 6.96; N, 7.84. Measured: C, 67.59; H, 7.28; N, 7.45.

3) Synthesis of Boc-Arg(Tos)-D-Trp-D-Leu-OPac:

Boc-D-Trp-D-Leu-OPac (2.14 g) was dissolved in 10 N—HCl/dioxane (15 ml) and stirred for 30 minutes while cooling with ice. The solvent was removed by distillation, and the residue was dried in the presence of sodium hydroxide. This was dissolved in DMF (15 ml), and diisopropylethylamine (0.79 ml) and Boc-Arg(Tos)-ONB (prepared from Boc-Arg(Tos)-OH.3/4 AcOEt.1/4 $H_2O$ (3.59 g), HONB (1.58 g) and DCC (1.83 g)) were added thereto and stirred overnight while cooling with ice. The solvent was removed by distillation, the residue was dissolved in AcOEt, and N,N-diisopropylethylamine (0.94 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 3.37 g (100.0%)

$R_f$: 0.53 m.p.: 108.0–110° C.

Elementary analysis: as $C_{43}H_{55}N_7O_9S$. Calculated: C, 61.05; H, 6.55; N, 11.59. Measured: C, 61.04; H, 6.91; N, 10.99.

4) Synthesis of Boc-D-Tyr(Br-Z)-Arg(Tos)-D-Trp-D-Leu-OPac:

Boc-Arg(Tos)-D-Trp-D-Leu-OPac (1.69 g) was dissolved in 10 N—HCl/dioxane (15 ml) and stirred for 30 minutes while cooling with ice. The solvent was removed by distillation, and the residue was dried in the presence of sodium hydroxide. This was dissolved in DMF (100 ml), and diisopropylethylamine (0.79 ml) and Boc-D-Tyr(Br-Z)ONB (prepared from Boc-D-Tyr(Br-Z)-OH (1.09 g), HONB (430 mg) and DCC (495 mg)) were added thereto and stirred overnight while cooling with ice. The solvent was removed by distillation, the residue was dissolved in AcOEt, and N,N-diisopropylethylamine (0.29 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.69 g (69.1%)

$R_f$: 0.59 m.p.: 105.0–107.0° C.

Elementary analysis: as $C_{60}H_{69}N_8O_{13}BrS.H_2O$. Calculated: C, 58.11; H, 5.77; N, 9.03. Measured: C, 57.75; H, 5.97; N, 8.90.

5) Synthesis of Boc-Lys($SO_2$Nap(1))-OH.CHA:

Boc-Lys-OH (2.00 g) was dissolved in dioxane (28 ml)-water (14 ml), and 1 N-NaOH (17.1 ml), and a dioxane solution (10 ml) of 1-naphthalenesulfonyl chloride (2.03 g) were dropwise added thereto and stirred while cooling with ice. The solvent was removed by distillation, the residue was dissolved in AcOEt (100 ml)-water (100 ml), 1 N—HCl was added to the resulting solution, while cooling with ice, to thereby make it acidic, and the AcOEt layer was separated. The AcOEt layer was washed with saturated saline solution (100 ml×2), dried with anhydrous sodium sulfate and concentrated. The resulting concentrate was dissolved in $CHCl_3$, cyclohexylamine (1.01 ml) was added thereto, and the solvent was removed by distillation. Petroleum ether was added to the residue, and the intended product was obtained as a precipitate.

Yield: 3.28 g (75.4%)

m.p.: 90.0–93.5° C.

FAB-MS (M+H)$^+$ (as Boc-Lys($SO_2$Nap(1))-OH): 436 (theoretical value: 436)

6) Synthesis of Boc-Lys($SO_2$Na(1))-D-Tyr(Br-Z)-Arg(Tos)-D-Trp-D-Leu-OPac:

Boc-D-Tyr(Br-Z)-Arg(Tos)-D-Trp-D-Leu-OPac (800 mg) was dissolved in 10 N—HCl/dioxane (10 ml) and stirred for 30 minutes, while cooling with ice. The solvent was removed by distillation, and the residue was dried in the presence of sodium hydroxide.

This was dissolved in DMF (5 ml), and diisopropylethylamine (0.26 ml) and Boc-Lys($SO_2$Nap(1))-ONB (prepared from Boc-Lys($SO_2$Nap(1))-OH.CHA (643 mg) as produced in Example 1-4), HONB (251 mg) and DCC (289 mg)) were added thereto and stirred overnight while cooling with ice. The solvent was removed by distillation, the residue was dissolved in AcOEt, and N,N-diisopropylethylamine (0.16 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.01 g (100.0%)

$R_f$: 0.60 m.p.: 115.0–117.0° C.

Elementary analysis: as $C_{76}H_{87}N_{10}O_{16}BrS_2 \cdot 0.25\ H_2O$. Calculated: C, 59.08; H, 5.68; N, 9.07. Measured: C, 58.96; H, 6.11; N, 9.01.

7) Synthesis of cyclo(-D-Leu-Lys(SO$_2$Nap(1))-D-Tyr-Arg-D-Trp-):

Boc-Lys(SO$_2$Na(1))-D-Tyr(Br-Z)-Arg(Tos)-D-Trp-D-Leu-OPac (530 mg) was dissolved in 90%-acetic acid (20 ml), and Zn (1.12 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (123 mg) and DCC (142 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (100 ml) solution of diisopropylethylamine (0.62 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 56.1 mg (52.2%)

Amino acid analysis (after hydrolyzed in 6 N—HCl at 110° C. for 24 hours) (Parenthesized are the theoretical data.): Leu 1.00 (1); Tyr 0.89 (1); Lys 0.17 (1); Arg 0.86 (1).

FAB-MS (M+H)$^+$: 937 (theoretical value: 937)

Example 25

Synthesis of cyclo(-D-Tyr-Arg(Tos)-D-Trp-Leu-D-Lys(SO$_2$Nap(1))-)

Boc-D-Lys (SO$_2$Nap(1))-D-Tyr(Br-Z)-Arg(Tos)-D-Trp-Leu-OPac (530 mg) obtained in Example 23-3) was dissolved in 90%-acetic acid (20 ml), and Zn (1.12 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (123 mg) and DCC (142 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (100 ml) solution of diisopropylethylamine (0.62 ml) and directly stirred overnight. The solvent was removed by distillation, the residue was washed for a total of two times with AcOEt (100 ml), and a pale yellow powder was obtained. The thus-obtained pale yellow powder (50 mg) was dissolved in DMF (50 ml) and subjected to catalytic reduction in a hydrogen stream in the presence of a catalyst of Pd-black. After the reduction, the catalyst used was removed by filtration, and the residue was purified by silica gel column chromatography (Merck Kieselgel 60, 10% methanol-chloroform) to obtain the intended product.

Yield: 7.0 mg (16.9%)

Amino acid analysis (after hydrolyzed in 6 N—HCl at 110° C. for 24 hours) (Parenthesized are the theoretical data.): Leu 1.00 (1); Tyr 0.95 (1); Lys 0.25 (1); Arg 0.65 (1).

FAB-MS (M+H)$^+$: 1091 (theoretical value: 1091)

Example 26

Synthesis of cyclo(-Arg(Tos)-D-Lys (SO$_2$Nap (1))-Tyr-D-Trp-Leu-)

Boc-Arg (Tos)-D-Lys (SO$_2$Nap (1))-Tyr(Br-Z)-D-Trp-Leu-OPac (530 mg) obtained in Example 1-6) was dissolved in 90%-acetic acid (20 ml), and Zn (1.12 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (123 mg) and DCC (142 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (100 ml) solution of diisopropylethylamine (0.62 ml) and directly stirred overnight. The solvent was removed by distillation, the residue was washed for a total of two times with AcOEt (100 ml), and a pale yellow powder was obtained. The thus-obtained pale yellow powder (80 mg) was dissolved in DMF (50 ml) and subjected to catalytic reduction in a hydrogen stream in the presence of a catalyst of Pd-black. After the reduction, the catalyst used was removed by filtration, and the solvent was removed by distillation. Then, the intended product was obtained as a precipitate from chloroform-petroleum ether.

Yield: 66 mg (100%)

Amino acid analysis (after hydrolyzed in 6 N—HCl at 110° C. for 24 hours) (Parenthesized are the theoretical data.): Leu 1.00 (1); Tyr 0.91 (1); Lys 0.22 (1); Arg 0.52 (1).

FAB-MS (M+H)$^+$: 1091 (theoretical value: 1091)

Example 27

Synthesis of cyclo(-Arg-D-Glu (NHCH$_2$CH$_2$Ph)-Tyr-D-Trp-Phe-)

1) Synthesis of Boc-Phe-Arg(Tos)-OPac:

In the same manner as in Example 2-2, the Boc group of Boc-Arg(Tos)-OBzl (520 mg) was removed in 10 N—HCl/dioxane (10 ml), and diisopropylethylamine (0.4 ml) and Boc-Phe-ONB (prepared from Boc-Phe-OH (531 mg), HONB (394 mg) and DCC (454 mg)) were added to the resulting compound to obtain Boc-Phe-Arg(Tos)-OBzl. Next, in the same manner as in Example 2-3, the Bzl group of the compound was removed by catalytic reduction in methanol in the presence of 10%-Pd-carbon, and the thus-reduced compound was treated with Cs$_2$CO$_3$ (358 mg) and phenacyl bromide (418 mg) to obtain the intended product.

Yield: 693 mg (100%)

R$_f$: 0.62 m.p.: 85.0–87.5° C.

Elementary analysis: as C$_{35}$H$_{43}$N$_5$O$_8$S. Calculated: C, 60.59; H, 6.25; N, 10.09. Measured: C, 60.40; H, 6.27; N, 9.95.

2) Synthesis of Boc-D-Trp-Phe-Arg(Tos)-OPac:

In the same manner as in Example 4-1, the Boc group of Boc-Phe-Arg(Tos)-OPac (690 mg) was removed in 10 N—HCl/dioxane (10 ml), and diisopropylethylamine (0.4 ml) and Boc-D-Trp-ONB (prepared from Boc-D-Trp-OH (670 mg), HONB (430 mg) and DCC (495 mg)) were added to the resulting compound to obtain the intended product.

Yield: 660 mg (75.0%)

R$_f$: 0.56 m.p.: 113.0–115.0° C.

Elementary analysis: as C$_{46}$H$_{53}$N$_7$O$_9$S. Calculated: C, 62.78; H, 6.07; N, 11.14. Measured: C, 62.52; H, 6.00; N, 11.00.

3) Synthesis of Boc-Tyr(Br-Z)-D-Trp-Phe-Arg(Tos)-OPac:

In the same manner as in Example 1-3, the Boc group of Boc-D-Trp-Phe-Arg(Tos)-OPac (315 mg) was removed in 10 N—HCl/dioxane (10 ml), and diisopropylethylamine (0.4 ml) and Boc-Tyr(Br-Z)-ONB (prepared from Boc-Tyr (Br-Z)-OH (988 mg), HONB (394 mg) and DCC (413 mg)) were added to the resulting compound to obtain the intended product.

Yield: 410 mg (91.2%)

R$_f$: 0.60 m.p.: 108.0–110.0° C.

Elementary analysis: as C$_{63}$H$_{67}$N$_8$O$_{13}$BrS.H$_2$O. Calculated: C, 59.38; H, 5.30; N, 8.79. Measured: C, 59.34; H, 5.05; N, 8.85.

4) Synthesis of Boc-D-Glu(NHCH$_2$CH$_2$Ph)-Tyr(Br-Z)-D-Trp-Phe-Arg(Tos)-OPac:

In the same manner as in Example 8-2), the Boc group of Boc-Tyr(Br-Z)-D-Trp-Phe-Arg(Tos)-OPac (390 mg) was removed in 10 N—HCl/dioxane (10 ml), and diisopropyl-ethylamine (0.4 ml) and Boc-D-Glu(NHCH$_2$CH$_2$Ph)-ONB (prepared by removing the Bzl group of Boc-D-Glu (NHCH$_2$CH$_2$Ph)-OBzl (441 mg) by catalytic reduction with 10%-Pd-C followed by adding HONB (197 mg) and DCC (227 mg) thereto) were added to the resulting compound to obtain the intended product.

Yield: 470 mg (100%)

R$_f$: 0.58 m.p.: 101.0–103.0° C.

Elementary analysis: as C$_{76}$H$_{83}$N$_{10}$O$_{15}$BrS.H$_2$O. Calculated: C, 61.14; H, 5.60; N, 9.38. Measured: C, 60.95; H, 5.55; N, 9.27.

5) Synthesis of cyclo(-Arg-D-Glu(NHCH$_2$CH$_2$Ph)-Tyr-D-Trp-Phe-):

In the same manner as in Example 2-8), Boc-D-Glu (NHCH$_2$CH$_2$Ph)-Tyr(Br-Z)-D-Trp-Phe-Arg(Tos)-OPac (450 mg) was dissolved in 90%-acetic acid (20 ml), and Zn (987 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in chloroform (20 ml), and HONB (541 mg) and DCC (623 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (30 ml), then dropwise added to a DMF (250 ml) solution of diisopropylethylamine (0.54 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 99.0 mg (37.0%)

Amino acid analysis (after hydrolyzed in 6 N—HCl at 110° C. for 24 hours) (Parenthesized are the theoretical data.): Phe 1.00 (1); Tyr 0.93 (1); Glu 1.02 (1); Arg 1.02 (1).

FAB-MS (M+H)$^+$: 885 (theoretical value: 885)

Example 28

Synthesis of cyclo(-Arg-D-Glu(NHCH$_2$CH$_2$Ph)-Tyr-D-Trp-Trp-)

1) Synthesis of Boc-Trp-Arg(Tos)-OPac:

In the same manner as in Example 2-2), the Boc group of Boc-Arg(Tos)-OBzl (520 mg) was removed in 10 N—HCl/dioxane (10 ml), and diisopropylethylamine (0.4 ml) and Boc-Trp-ONB (prepared from Boc-Trp-OH (670 mg), HONB (430 mg) and DCC (495 mg)) were added to the resulting compound to obtain Boc-Trp-Arg(Tos)-OBzl. Next, in the same manner as in Example 2-3), the Bzl group of the compound was removed by catalytic reduction in methanol in the presence of 10%-Pd-carbon, and the thus-reduced compound was treated with Cs$_2$CO$_3$ (358 mg) and phenacyl bromide (418 mg) to obtain the intended product.

Yield: 734 mg (100%)

R$_f$: 0.60 m.p.: 107.0–109.0° C.

Elementary analysis: as C$_{37}$H$_{44}$N$_6$O$_8$S. Calculated: C, 60.64; H, 6.05; N, 11.47. Measured: C, 60.50; H, 5.97; N, 11.28.

2) Synthesis of Boc-D-Trp-Trp-Arg(Tos)-OPac:

In the same manner as in Example 4-1), the Boc group of Boc-Trp-Arg(Tos)-OPac (734 mg) was removed in 10 N—HCl/dioxane (10 ml), and diisopropylethylamine (0.4 ml) and Boc-D-Trp-ONB (prepared from Boc-D-Trp-OH (670 mg), HONB (430 mg) and DCC (495 mg)) were added to the resulting compound to obtain the intended product.

Yield: 900 mg (97.9%)

$R_f$: 0.50 m.p.: 124.0–125.0 C.

Elementary analysis: as $C_{48}H_{54}N_8O_9S$. Calculated: C, 62.73; H, 5.92; N, 12.19. Measured: C, 62.55; H, 5.71; N, 11.90.

3) Synthesis of Boc-Tyr(Br-Z)-D-Trp-Trp-Arg(Tos)-OPac:

In the same manner as in Example 1-3), the Boc group of Boc-D-Trp-Trp-Arg(Tos)-OPac (450 mg) was removed in 10 N—HCl/dioxane (10 ml), and diisopropylethylamine (0.4 ml) and Boc-Tyr(Br-Z)-ONB (prepared from Boc-Tyr (Br-Z)-OH (988 mg), HONB (394 mg) and DCC (413 mg)) were added to the resulting compound to obtain the intended product.

Yield: 530 mg (83.5%)

$R_f$: 0.50 m.p.: 122.0–124.0° C.

Elementary analysis: as $C_{63}H_{68}N_9O_{13}BrS \cdot 0.25\ H_2O$. Calculated: C, 60.06; H, 5.27; N, 9.70. Measured: C, 59.94; H, 5.27; N, 9.55.

4) Synthesis of Boc-D-Glu(NHCH$_2$CH$_2$Ph)-Tyr(Br-Z)-D-Trp-Trp-Arg(Tos)-OPac:

In the same manner as in Example 8-2), the Boc group of Boc-Tyr(Br-Z)-D-Trp-Trp-Arg(Tos)-OPac (510 mg) was removed in 10 N—HCl/dioxane (10 ml), and diisopropylethylamine (0.4 ml) and Boc-D-Glu(NHCH$_2$CH$_2$Ph)-ONB (prepared by removing the Bzl group of Boc-D-Glu (NHCH$_2$CH$_2$Ph)-OBzl (441 mg) by catalytic reduction with 10%-Pd-C followed by adding HONB (197 mg) and DCC (227 mg) thereto) were added to the resulting compound to obtain the intended product.

Yield: 590 mg (98.0%)

$R_f$: 0.50 m.p.: 112.0–114.0° C.

Elementary analysis: as $C_{78}H_{84}N_{11}O_{15}BrS \cdot 0.75\ H_2O$. Calculated: C, 60.79; H, 5.49; N, 10.00. Measured: C, 60.49; H, 5.45; N, 9.87.

5) Synthesis of cyclo(-Arg-D-Glu(NHCH$_2$CH$_2$Ph)-Tyr-D-Trp-Trp-):

In the same manner as in Example 2-8), Boc-D-Glu (NHCH$_2$CH$_2$Ph)-Tyr(Br-Z)-D-Trp-Trp-Arg(Tos)-OPac (570 mg) was dissolved in 90%-acetic acid (20 ml), and Zn (1.22 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in chloroform (20 ml), and HONB (668 mg) and DCC (770 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (30 ml), then dropwise added to a DMF (250 ml) solution of diisopropylethylamine (0.67 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 51.0 mg (14.8%) Amino acid analysis (after hydrolyzed in 6 N—HCl at 110° C. for 24 hours) (Parenthesized are the theoretical data.): Tyr 0.93 (1); Glu 1.00 (1); Arg 1.02 (1)

FAB-MS (M+H)$^+$: 924 (theoretical value: 924).

Example 29

Synthesis of cyclo(-Arg-D-Glu(NHCH$_2$CH$_2$Ph)-Lys (COPh)-D-Trp-Phe-)

1) Synthesis of Boc-Lys(COPh)-D-Trp-Phe-Arg(Tos)-OPac:

In the same manner as in Example 21-2), the Boc group of Boc-D-Trp-Phe-Arg(Tos)-OPac (450 mg) was removed in 10 N—HCl/dioxane (10 ml), and diisopropylethylamine (0.4 ml) and Boc-Lys(COPh)-ONB (prepared from Boc-Lys (COPh)-OH·CHA (449 mg), HONB (197 mg) and DCC (227 mg)) were added to the resulting compound to obtain the intended product.

Yield: 330 mg (60.5%)

$R_f$: 0.57 m.p.: 116.0–118.5° C.

Elementary analysis: as $C_{59}H_{69}N_9O_{11}S \cdot 0.25\ H_2O$. Calculated: C, 63.45; H, 6.23; N, 11.29. Measured: C, 63.24; H, 6.17; N, 10.99.

2) Synthesis of Boc-D-Glu(NHCH$_2$CH$_2$Ph)-Lys(COPh)-D-Trp-Phe-Arg(Tos)-OPac:

In the same manner as in Example 8-2), the Boc group of Boc-Lys(COPh)-D-Trp-Phe-Arg(Tos)-OPac (310 mg) was removed in 10 N—HCl/dioxane (10 ml), and diisopropylethylamine (0.4 ml) and Boc-D-Glu(NHCH$_2$CH$_2$Ph)-ONB (prepared by removing the Bzl group of Boc-D-Glu (NHCH$_2$CH$_2$Ph)-OBzl (441 mg) by catalytic reduction with 10%-Pd-C followed by adding HONB (197 mg) and DCC (227 mg) thereto) were added to the resulting compound to obtain the intended product.

Yield: 376 mg (100%)

$R_f$: 0.58 m.p.: 119.0–121.5° C.

Elementary analysis: as $C_{72}H_{85}N_{11}O_{13}S \cdot 1.5\ H_2O$. Calculated: C, 63.05; H, 6.25; N, 11.23. Measured: C, 62.77; H, 6.23; N, 10.95.

3) Synthesis of cyclo(-Arg-D-Glu(NHCH$_2$CH$_2$Ph)-Lys (COPh)-D-Trp-Phe-):

In the same manner as in Example 2-8), Boc-D-Glu (NHCH$_2$CH$_2$Ph)-Lys(COPh)-D-Trp-Phe-Arg(Tos)-OPac (480 mg) was dissolved in 90%-acetic acid (20 ml), and Zn (1.17 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in chloroform (20 ml), and HONB (640 mg) and DCC (737 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (30 ml), then dropwise added to a DMF (250 ml) solution of diisopropylethylamine (0.64 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 19.5 mg (5.7%)

Amino acid analysis (after hydrolyzed in 6 N—HCl at 110° C. for 24 hours) (Parenthesized are the theoretical data.): Phe 1.00 (1); Lys 0.84 (1); Glu 1.02 (1); Arg 1.02 (1).

FAB-MS (M+H)$^+$: 954 (theoretical value: 954)

Example 30

Synthesis of cyclo(-Arg-D-Glu(NHCH$_2$CH$_2$Ph)-Lys (COPh)-D-Trp-Trp-)

1) Synthesis of Boc-Lys(COPh)-D-Trp-Trp-Arg(Tos)-OPac:

In the same manner as in Example 21-2), the Boc group of Boc-D-Trp-Trp-Arg(Tos)-OPac (450 mg) was removed in 10 N—HCl/dioxane (10 ml), and diisopropylethylamine (0.4 ml) and Boc-Lys(COPh)-ONB (prepared from Boc-Lys (COPh)-OH.CHA (449 mg), HONB (197 mg) and DCC (227 mg)) were added to the resulting compound to obtain the intended product.

Yield: 510 mg (90.4%)

R$_f$: 0.46 m.p.: 128.0–131.0° C.

Elementary analysis: as C$_{61}$H$_{70}$N$_{10}$O$_{11}$S. Calculated: C, 63.64; H, 6.13; N, 12.17. Measured: C, 63.51; H, 6.10; N, 12.03.

2) Synthesis of Boc-D-Glu(NHCH$_2$CH$_2$Ph)-Lys(COPh)-D-Trp-Trp-Arg(Tos)-OPac:

In the same manner as in Example 8-2), the Boc group of Boc-Lys(COPh)-D-Trp-Trp-Arg(Tos)-OPac (310 mg) was removed in 10 N—HCl/dioxane (10 ml), and diisopropylethylamine (0.4 ml) and Boc-D-Glu(NHCH$_2$CH$_2$Ph)-ONB (prepared by removing the Bzl group of Boc-D-Glu (NHCH$_2$CH$_2$Ph)-OBzl (441 mg) by catalytic reduction with 10%-Pd-C followed by adding HONB (197 mg) and DCC (227 mg) thereto) were added to the resulting compound to obtain the intended product.

Yield: 386 mg (100%)

R$_f$: 0.50 m.p.: 118.0–120.0° C.

3) Synthesis of cyclo(-Arg-D-Glu(NHCH$_2$CH$_2$Ph)-Lys (COPh)-D-Trp-Trp-):

In the same manner as in Example 2-8), Boc-D-Glu (NHCH$_2$CH$_2$Ph)-Lys(COPh)-D-Trp-Trp-Arg(Tos)-OPac (360 mg) was dissolved in 90%-acetic acid (20 ml), and Zn (851 mg) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in chloroform (20 ml), and HONB (466 mg) and DCC (536 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (30 ml), then dropwise added to a DMF (250 ml) solution of diisopropylethylamine (0.47 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 36 mg (13.9%)

Amino acid analysis (after hydrolyzed in 6 N—HCl at 110° C. for 24 hours) (Parenthesized are the theoretical data.): Lys 0.84 (1); Glu 1.02 (1); Arg 1.02 (1)

FAB-MS (M+H)$^+$: 993 (theoretical value: 993).

Example 31

Synthesis of cyclo(-Arg-D-Glu(NHCH$_2$CH$_2$Ph)-Lys (CONap(1))-D-Trp-Leu-)

1) Synthesis of Boc-Lys(Cl-Z)-D-Trp-Leu-Arg(Tos)-OPac:

In the same manner as in Example 2-4), the Boc group of Boc-D-Trp-Leu-Arg(Tos)-OPac (29.7 g) was removed in 10 N—HCl/dioxane (100 ml). Next, in the same manner as in Example 18-1), diisopropylethylamine (7.60 ml) and Boc-Lys(Cl-Z)-ONB (prepared from Boc-Lys(Cl-Z)-OH (16.1 g), HONB (7.63 g) and DCC (8.79 g)) were added to the resulting compound to obtain the intended product.

Yield: 34.3 g (85.2%)

R$_f$: 0.60 m.p.: 103.0–105° C.

Elementary analysis: as C$_{57}$H$_{72}$N$_9$O$_{12}$ClS.0.75 H$_2$O. Calculated: C, 59.21; H, 6.28; N, 10.90. Measured: C, 59.14; H, 6.25; N, 10.88.

2) Synthesis of Boc-D-Glu(NHCH$_2$CH$_2$Ph)-Lys(Cl-Z)-D-Trp-Leu-Arg(Tos)-OPac:

In the same manner as in Example 8-2), the Boc group of Boc-Lys(Cl-Z)-D-Trp-Leu-Arg(Tos)-OPac (25.0 g) was removed in 10 N—HCl/dioxane (200 ml), and diisopropylethylamine (4.40 ml) and Boc-D-Glu(NHCH$_2$CH$_2$Ph)-ONB (prepared by removing the Bzl group of Boc-D-Glu (NHCH$_2$CH$_2$Ph)-OBzl (10.7 g) by catalytic reduction with 10%-Pd-C followed by adding HONB (4.77 g) and DCC (5.49 g) thereto) were added to the resulting compound to obtain the intended product.

Yield: 27.1 g (90.0%)

R$_f$: 0.60 m.p.: 102.0–104.0° C.

Elementary analysis: as C$_{70}$H$_{88}$N$_{11}$O$_{14}$ClS.0.25 H$_2$O. Calculated: C, 60.94; H, 6.43; N, 11.17. Measured: C, 60.77; H, 6.37; N, 10.89.

3) Synthesis of cyclo(-Arg(Tos)-D-Glu(NHCH$_2$CH$_2$Ph)-Lys (Cl-Z)-D-Trp-Leu-):

In the same manner as in Example 30-3), Boc-D-Glu (NHCH$_2$CH$_2$Ph)-Lys(Cl-Z)-D-Trp-Leu-Arg(Tos)-OPac (5.00 g) was dissolved in 90%-acetic acid (200 ml), and Zn (11.9 g) was added thereto and stirred for 30 minutes. Zn was removed, then the solvent was removed by distillation, and AcOEt (500 ml) and water (500 ml) were added to the residue. The aqueous layer was separated and washed with AcOEt (500 ml). The AcOEt layers were combined, washed with saturated saline solution (500 ml), dried with anhydrous sodium sulfate and concentrated, to obtain an oily product. Diethyl ether was added thereto to obtain a colorless precipitate. This was dissolved in chloroform (300 ml), and HONB (1.30 g) and DCC (1.50 g) were added thereto while cooling with ice and then stirred at 4° C. for 2 hours. The DCU formed was removed, and the solvent was removed by distillation. Next, 10 N—HCl/dioxane (200 ml) was added to the residue and stirred for 30 minutes while cooling with ice. The solvent was removed by distillation, and the residue was dried in the presence of sodium hydroxide. This was dissolved in DMF (300 ml), then dropwise added to a DMF (3000 ml) solution of diisopropylethylamine (6.30 ml) and directly stirred overnight. The solvent was removed by distillation, the residue was washed for a total of two times with ethanol (100 ml), and a pale yellow powder was obtained.

Yield: 2.88 g (72.3%)
FAB-MS (M+H)$^+$: 1138 (theoretical value: 1138)

4) Synthesis of cyclo(-Arg(Tos)-D-Glu(NHCH$_2$CH$_2$Ph)-Lys(CONap(1))-D-Trp-L eu-):

HONB (224 mg) and DCC (258 mg) were added to a DMF (20 ml) solution of 1-naphthoic acid (193 mg) and directly stirred for 11 hours (Nap(1)CO-ONB). Cyclo(-Arg(Tos)-D-Glu(NHCH$_2$CH$_2$Ph)-Lys(Cl-Z)-D-Trp-Leu-) (710 mg) was dissolved in DMF (150 ml) and then stirred for 3 days in a hydrogen stream in the presence of Pd-black. Then, the catalyst was removed by filtration, and the solvent was concentrated to 20 ml. Diisopropylethylamine (0.23 ml) and the previously-prepared Nap(1)CO-ONB were added to the resulting concentrate and directly stirred at room temperature for 11 hours. The solvent was removed by distillation under reduced pressure, and the residue was washed for a total of two times with ethanol (100 ml). Thus, the intended product was obtained.

Yield: 490 mg (70.0%)
FAB-MS (M+H)$^+$: 1124 (theoretical value: 1124)

5) Synthesis of cyclo(-Arg-D-Glu(NHCH$_2$CH$_2$Ph)-Lys(CONap(1))-D-Trp-Leu-):

Cyclo(-Arg(Tos)-D-Glu(NHCH$_2$CH$_2$Ph)-Lys(CONap(1))-D-Trp-Leu-) (150 mg) was dissolved in HF (5 ml) in the presence of p-cresol (200 mg) and 1,4-butane-dithiol (0.2 ml) and stirred for 1 hour. HF was removed by distillation, diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 117 mg (90.7%)
Amino acid analysis (after hydrolyzed in 6 N—HCl at 110° C. for 24 hours) (Parenthesized are the theoretical data.): Leu 1.00 (1); Lys 0.84 (1); Glu 1.02 (1); Arg 1.02 (1).
FAB-MS (M+H)$^+$: 970 (theoretical value: 970)

Example 32

Synthesis of cyclo(-Lys(isopropyl)-D-Glu(NHCH$_2$CH$_2$Ph)-Tyr-D-Lys (Nic)-Leu-)

1) Synthesis of Boc-D-Lys(Nic)-Leu-OBzl:

H-Leu-OBzl.Tos (1.12 g) was dissolved in DMF (100 ml) and cooled with ice, and diisopropylethylamine (0.52 ml) and Boc-D-Lys(Nic)-ONB (prepared from Boc-D-Lys(Nic)-OH (1.00 g), HONB (613 mg) and DCC (706 mg)) were added thereto and stirred overnight. The DCU formed was removed by filtration, the resulting filtrate was concentrated, then the concentrate was dissolved in AcOEt (100 ml), and N,N-diisopropylethylamine (0.37 ml) was added to the resulting solution and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and then concentrated to obtain an oily product.

Yield: 1.54 g (97.5%)
FAB-MS (M+H)$^+$: 554 (theoretical value: 554)

2) Synthesis of Boc-D-Lys(Nic)-Leu-OPac:

Boc-D-Lys(Nic)-Leu-OBzl (1.45 g) was dissolved in methanol (300 ml) and subjected to catalytic reduction in a hydrogen stream in the presence of a catalyst of 10%-Pd-carbon. The catalyst was removed by filtration, the resulting filtrate was concentrated to 10 ml, and an aqueous solution (15 ml) of Cs$_2$CO$_3$ (430 g) was dropwise added thereto. The solvent was removed by distillation, the residue was dissolved in DMF (20 ml), and a DMF (50 ml) solution of phenacyl bromide (521 mg) was added thereto and stirred overnight. The solvent was removed by distillation, and the residue was dissolved in AcOEt (150 ml). Then, the resulting solution was washed with aqueous 10%-citric acid solution, saturated saline solution, aqueous saturated sodium hydrogencarbonate solution and saturated saline solution, dried with anhydrous sodium sulfate and concentrated to obtain an oily product.

Yield: 1.25 g (82.1%)
R$_f$: 0.59
FAB-MS (M+H)$^+$: 582 (theoretical value: 582)

3) Synthesis of Boc-Tyr(Br-Z)-D-Lys(Nic)-Leu-OPac:

Boc-D-Lys(Nic)-Leu-OPac (1.97 g) was dissolved in 10 N—HCl/dioxane (20 ml) and stirred for 30 minutes while cooling with ice. The solvent was removed by distillation, and the residue was dried in the presence of sodium hydroxide. This was dissolved in DMF (100 ml), and diisopropylethylamine (0.75 ml) and Boc-Tyr(Br-Z)-ONB (prepared from Boc-Tyr(Br-Z)-OH (1.42 g), HONB (562 mg) and DCC (646 mg)) were added thereto and stirred overnight while cooling with ice. The solvent was removed by distillation, the residue was dissolved in AcOEt, and N,N-diisopropylethylamine (0.38 ml) was added thereto and stirred for 10 minutes. Water (300 ml) was added to the resulting mixture, and the AcOEt layer was separated. This was washed with aqueous 10 %-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.89 g (100%)
R$_f$: 0.60
m.p.: 106.0–108.0° C.
Elementary analysis: as C$_{48}$H$_{56}$N$_5$O$_{11}$Br. Calculated: C, 60.12; H, 5.89; N, 7.30. Measured: C, 60.10; H, 5.74; N, 7.28.

4) Synthesis of Boc-D-Glu(NHCH$_2$CH$_2$Ph)-Tyr(Br-Z)-D-Lys(Nic)-Leu-OPac:

In the same manner as in Example 8-2), the Boc group of Boc-Tyr(Br-Z)-D-Lys(Nic)-Leu-OPac (1.68 g) was removed in 10 N—HCl/dioxane (200 ml), and diisopropylethylamine (0.66 ml) and Boc-D-Glu(NHCH$_2$CH$_2$Ph)-ONB (prepared by removing the Bzl group of Boc-D-Glu(NHCH$_2$CH$_2$Ph)-OBzl (793 mg) by catalytic reduction with 10%-Pd-C followed by adding HONB (387 mg) and DCC (446 mg) thereto) were added to the resulting compound to obtain the intended product.

Yield: 1.22 g (58.5%)
R$_f$: 0.59
m.p.: 145.0–148.0° C.
Elementary analysis: as C$_{61}$H$_{72}$N$_7$O$_{13}$Br. Calculated: C, 60.82; H, 6.02; N, 8.14. Measured: C, 60.73; H, 5.88; N, 7.95.

5) Synthesis of Boc-Lys(Z, isopropyl)-D-Glu (NHCH$_2$CH$_2$Ph)-Tyr(Br-Z)-D-Lys(Nic)-Leu-O Pac:

Boc-D-Glu (NHCH$_2$CH$_2$Ph)-Tyr (Br-Z)-D-Lys (Nic)-Leu-OPac (1.02 g) was dissolved in 10 N—HCl/dioxane (20 ml) and stirred for 30 minutes while cooling with ice. The solvent was removed by distillation, and the residue was dried in the presence of sodium hydroxide. This was dissolved in DMF (100 ml), and diisopropylethylamine (0.17 ml) and Boc-Lys(Z, isopropyl)-ONB (prepared from Boc-Lys(Z, isopropyl)-OH (854 mg), HONB (394 mg) and DCC (454 mg)) were added thereto and stirred overnight while cooling with ice. The solvent was removed by distillation, the residue was dissolved in AcOEt, and N,N-diisopropylethylamine (0.17 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 1.28 g (100%)
R$_f$: 0.63
m.p.: 148.0–150.0° C.
Elementary analysis: as C$_{78}$H$_{96}$N$_9$O$_{16}$Br. Calculated: C, 62.64; H, 6.47; N, 8.43. Measured: C, 62.47; H, 6.44; N, 8.39.

6) Synthesis of cyclo(-Lys(isopropyl)-D-Glu (NHCH$_2$CH$_2$Ph)-Tyr-D-Lys(Nic)-Leu-):

In the same manner as in Example 2-8), Boc-Lys(Z, isopropyl)-D-Glu (NHCH$_2$CH$_2$Ph)-Tyr (Br-Z)-D-Lys (Nic)-Leu-OPac (500 mg) was dissolved in 90%-acetic acid (20 ml), and Zn (1.09 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in chloroform (20 ml), and HONB (140 mg) and DCC (161 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (30 ml), then dropwise added to a DMF (250 ml) solution of diisopropylethylamine (0.70 ml) and directly stirred overnight. The solvent was removed by distillation, the residue was washed for a total of two times with ethanol (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 135 mg (44.3%)
Amino acid analysis (after hydrolyzed in 6 N—HCl at 110° C. for 24 hours) (Parenthesized are the theoretical data.): Lys 0.84 (1); Glu 1.02 (1); Leu 1.00 (1); Tyr 0.92 (1).
FAB-MS (M+H)$^+$: 912 (theoretical value: 912)

Example 33

Synthesis of cyclo(-Arg-D-Lys(Ac)-Tyr-D-Trp-Leu-)

1) Synthesis of Boc-D-Lys(Ac)-OH.CHA:

Boc-D-Lys-OH (1.00 g) was suspended in dichloromethane (30 ml), and diisopropylethylamine (0.80 ml) and AcONB (prepared from acetic acid (0.26 ml), HONB (873 mg) and DCC (1.00 g)) were added thereto and stirred for 11 hours while cooling with ice. Then, the solvent was removed by distillation, the residue was dissolved in AcOEt (100 ml), and N,N-diisopropylethylamine (0.58 ml) was added thereto and stirred for 10 minutes. Water (100 ml) was added to the resulting mixture, and the AcOEt layer was separated. This was washed with 1 N-H$_2$SO$_4$, then dried with anhydrous sodium sulfate and concentrated. The resulting concentrate was dissolved in CHCl$_3$, cyclohexylamine (0.51 ml) was added thereto, and the solvent was removed by distillation. Thus, the intended product was obtained as an oily substance.

Yield: 1.56 g (100%)
FAB-MS (M+H)$^+$: 288 (theoretical value: 288)

2) Synthesis of Boc-D-Lys(Ac)-Tyr(Br-Z)-D-Trp-Leu-Arg (Tos)-OPac:

Boc-Tyr(Br-Z)-D-Trp-Leu-Arg(Tos)-OPac (1.38 g) as obtained in Example 2-5) was dissolved in 10 N—HCl/dioxane (20 ml) and stirred for 30 minutes, while cooling with ice. The solvent was removed by distillation, and the residue was dried in the presence of sodium hydroxide. This was dissolved in DMF (10 ml), and diisopropylethylamine (0.41 ml) and Boc-D-Lys(Ac)-ONB (prepared from Boc-D-Lys(Ac)-OH.CHA (1.55 g), HONB (873 mg) and DCC (1.00 g)) were added thereto and stirred overnight while cooling with ice. The solvent was removed by distillation, the residue was dissolved in AcOEt, and N,N-diisopropylethylamine (0.52 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 990 mg (62.9%)
R$_f$: 0.60
m.p.: 105.0–108.0° C.
Elementary analysis: as C$_{68}$H$_{83}$N$_{10}$O$_{15}$BrS.0.88 H$_2$O. Calculated: C, 58.00; H, 5.94; N, 9.95 . Measured: C, 57.74; H, 5.75; N, 9.80.

3) Synthesis of cyclo(-Arg-D-Lys(Ac)-Tyr-D-Trp-Leu-):

In the same manner as in Example 2-8), Boc-D-Lys(Ac)-Tyr(Br-Z)-D-Trp-Leu-Arg(Tos)-OPac (530 mg) was dissolved in 90%-acetic acid (50 ml), and Zn (1.24 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in chloroform (20 ml), and HONB (137 mg) and DCC (157 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (30 ml), then dropwise added to a DMF (250 ml) solution of diisopropylethylamine (0.69 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 70.5 mg (23.9%)

Amino acid analysis (after hydrolyzed in 6 N—HCl at 110° C. for 24 hours) (Parenthesized are the theoretical data.): Leu 1.00 (1); Tyr 0.90 (1); Lys 0.21 (1); Arg 0.94 (1).

FAB-MS (M+H)$^+$: 772 (theoretical value: 772)

Example 34

Synthesis of cyclo(-Leu-D-Arg-Lys(SO$_2$Nap(1))-D-Tyr-Trp-)

1) Synthesis of Boc-Trp-Leu-OPac:

In the same manner as in Example 1-1) and -2), H-Leu-OBzl.Tos (7.87 g) was dissolved in DMF (100 ml) and cooled with ice, and diisopropylethylamine (3.96 ml) and Boc-Trp-ONB (prepared from Boc-Trp-OH (6.69 g), HONB (4.30 g) and DCC (4.95 g)) were added thereto and stirred overnight. The DCU formed was removed by filtration, the filtrate was concentrated, the concentrate was dissolved in AcOEt (200 ml), and N,N-diisopropylethylamine (2.86 ml) was added to the resulting solution and stirred for 10 minutes. Water (500 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was dissolved in methanol (500 ml) and subjected to catalytic reduction in a hydrogen stream in the presence of 10%-Pd-carbon as the catalyst. The catalyst was removed by filtration, the resulting filtrate was concentrated to 100 ml, and an aqueous solution (10 ml) of Cs$_2$CO$_3$ (3.26 g) was dropwise added thereto. The solvent was removed by distillation, the residue was dissolved in DMF (200 ml), and a DMF (50 ml) solution of phenacyl bromide (3.98 g) was added thereto and stirred overnight. The solvent was removed by distillation, and the residue was dissolved in AcOEt (300 ml). Then, the resulting solution was washed with aqueous 10%-citric acid solution, saturated saline solution, aqueous saturated sodium hydrogencarbonate solution and saturated saline solution, dried with anhydrous sodium sulfate and concentrated. Thus, the intended product was obtained as an oily substance.

Yield: 9/84 g (92.0%)

R$_f$: 0.82

FAB-MS (M+H)$^+$: 535 (theoretical value: 535)

2) Synthesis of Boc-D-Tyr (Br-Z )-Trp-Leu-OPac:

Boc-Trp-Leu-OPac (12.14 g) was dissolved in 10 N—HCl/dioxane (20 ml) and stirred for 30 minutes, while cooling with ice. The solvent was removed by distillation, and the residue was dried in the presence of sodium hydroxide. This was dissolved in DMF (100 ml), and diisopropylethylamine (0.79 ml) and Boc-D-Tyr(Br-Z)-ONB (prepared from Boc-D-tyr(Br-Z)-OH (2.18 g), HONB (0.86 g) and DCC (0.99 g)) were added thereto and stirred overnight while cooling with ice. The solvent was removed by distillation, the residue was dissolved in AcOEt, and N,N-diisopropylethylamine (0.57 ml) was added thereto and stirred for 10 minutes. Water (300 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily product. This was purified by silica gel column chromatography (Merck Kieselgel 60, 0.5% methanol-chloroform), and the intended product was obtained as a precipitate from chloroform-petroleum ether.

Yield: 3.63 g (100.0%)

R$_f$: 0.79 m.p.: 176.0–178.0° C.

Elementary analysis: as C$_{47}$H$_{51}$N$_4$O$_{10}$OBr. Calculated: C, 61.91; H, 5.64; N, 6.14. Measured: C, 61.57; H, 5.72; N, 6.17.

3) Synthesis of Boc-Lys(SO$_2$Nap(1))-D-Tyr(Br-Z)-Trp-Leu-OPac:

Boc-D-Tyr(Br-Z)-Trp-Leu-OPac (912 mg) was dissolved in 10 N—HCl/dioxane (10 ml) and stirred for 30 minutes, while cooling with ice. The solvent was removed by distillation, and the residue was dried in the presence of sodium hydroxide.

This was dissolved in DMF (5 ml), and diisopropylethylamine (0.26 ml) and Boc-Lys(SO$_2$Nap(1))-ONB (prepared from Boc-Lys(SO$_2$Nap(1))-OH.CHA (643 mg) as produced in Example 1-4), HONB (251 mg) and DCC (289 mg)) were added thereto and stirred overnight while cooling with ice. The solvent was removed by distillation, the residue was dissolved in AcOEt, and N,N-diisopropylethylamine (0.16 ml) was added thereto and stirred for 10 minutes.

Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated. Then, the intended product was obtained as a precipitate from chloroform-petroleum ether.

Yield: 0.99 g (80.5%)

R$_f$: 0.72 m.p.: 108.0–110.0° C.

Elementary analysis: as C$_{63}$H$_{69}$N$_6$O$_{13}$BrS.H$_2$O. Calculated: C, 60.02; H, 5.57; N, 6.73. Measured: C, 60.59; H, 5.54; N, 6.57.

4) Synthesis of Boc-D-Arg(Tos)-Lys(SO₂Nap(1))-D-Tyr(Br-Z)-Trp-Leu-OPac:

Boc-Lys(SO₂Nap(1))-D-Tyr(Br-Z)-Trp-Leu-OPac (0.95 g) was dissolved in 10 N—HCl/dioxane (10 ml) and stirred for 30 minutes, while cooling with ice. The solvent was removed by distillation, and the residue was dried in the presence of sodium hydroxide. This was dissolved in DMF (5 ml), and diisopropylethylamine (0.15 ml) and Boc-Arg(Tos)-ONB (prepared from Boc-Arg(Tos)-OH.1/4 H₂O.3/4 AcOEt (562 mg), HONB (249 mg) and DCC (287 mg)) were added thereto and stirred overnight while cooling with ice. The solvent was removed by distillation, the residue was dissolved in AcOEt (100 ml), and N,N-diisopropylethylamine (0.15 ml) was added thereto and stirred for 10 minutes. Water (100 ml) was added to the resulting mixture, and the AcOEt layer was separated. This was washed with aqueous 10%-citric acid solution, saturated saline solution, aqueous saturated sodium hydrogencarbonate solution and saturated saline solution, dried with anhydrous sodium sulfate and concentrated to obtain an oily substance. Then, the intended product was obtained as a precipitate from chloroform-petroleum ether.

Yield: 0.88 g (74.0%)

$R_f$: 0.65 m.p.: 113.0–115.0° C.

Elementary analysis: as $C_{76}H_{87}N_{10}O_{16}BrS_2H_2O$. Calculated: C, 58.57; H, 5.76; N, 8.99. Measured: C, 58.20; H, 5.70; N, 8.74.

5) Synthesis of cyclo(-Leu-D-Arg-Lys(SO₂Nap(1)-D-Tyr-Trp-):

Boc-D-Arg(Tos)-Lys(SO₂Nap(1))-D-Tyr(Br-Z)-Trp-Leu-OPac (530 mg) was dissolved in 90%-acetic acid (20 ml), and Zn (1.12 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in dichloromethane (20 ml), and HONB (123 mg) and DCC (142 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (5 ml), then dropwise added to a DMF (300 ml) solution of diisopropylethylamine (0.62 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 68 mg (21.1%)

Amino acid analysis (after hydrolyzed in 6 N—HCl at 110C. for 24 hours) (Parenthesized are the theoretical data.): Leu 1.00 (1); Tyr 0.92 (1); Lys 0.23 (1); Arg 0.99 (1).

FAB-MS (M+H)⁺: 937 (theoretical value: 937)

Example 35

Synthesis of cyclo(-Phe-D-Arg-(Mtr)-Phe-D-Ala-Trp-)

1) Synthesis of Fmoc-D-Ala-Trp-Phe-D-Arg(Mtr)-Phe-OH:

Fmoc-Phe-Wang Resin (417 mg, 0.25 mmol) was condensed with the constitutive Fmoc-amino acids (1 mmol each) in order, using HBTU-HOBt as a condensing agent and removing Fmoc by the use of 20%-piperidine, whereby the peptide chain was stepwise extended to give Fmoc-D-Ala-Trp-Phe-D-Arg(Mtr)-Phe-Wang Resin. A peptide synthesizer of Model 431A (produced by ABI Co.) was used herein for the peptide synthesis. Next, the thus-obtained peptide-resin (244 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-D-Ala-Trp-Phe-D-Arg(Mtr)-Phe-OH.

Yield: 96 mg (82.8%)

FAB-MS (M+H)⁺: 1161 (theoretical value: 1161)

Elution time: 36.2 min

2) Synthesis of cyclo(-Phe-D-Arg(Mtr)-Phe-D-Ala-Trp-):

Fmoc-D-Ala-Trp-Phe-D-Arg(Mtr)-Phe-OH (87 mg) obtained in Example 35-1) was stirred in 10%-diethylamine/DMF (10 ml) for 2 hours. The reaction mixture was concentrated under reduced pressure and dissolved in DMF (75 ml), and PyBOP (78 mg) and DIEA (26 ml) were added thereto while cooling with ice and then stirred overnight at room temperature. After having been concentrated under reduced pressure, water was added to this, and the precipitate formed was collected by filtration. Thus, a crude cyclo(-Phe-D-Arg(Mtr)-Phe-D-Ala-Trp-) was obtained. A half of the crude product thus obtained was purified by HPLC using a column for partitioning purification of D-ODS-5-ST (2 cm×15 cm; produced by YMC Co.) to obtain cyclo(-Phe-D-Arg(Mtr)-Phe-D-Ala-Trp-).

Yield: 2.0 mg (5.8%)

FAB-MS (M+H)⁺: 920 (theoretical value: 920)

Elution time: 32.6 min

Example 36

Synthesis of cyclo(-Phe-D-Arg-Phe-D-Ala-Trp-)

The crude cyclo(-Phe-D-Arg(Mtr)-Phe-D-Ala-Trp-) (10 mg) as obtained in Example 35-2) was stirred in Reagent K (82.5%-TFA, 5%-thioanisole, 5%-H₂O, 2.5%-ethanedithiol) (5 ml) for 12 hours. After having been concentrated under reduced pressure, this was washed with ether, and the residue was purified by HPLC using a column for partitioning purification of D-ODS-5-ST (2 cm×15 cm; produced by YMC Co.) to obtain cyclo(-Phe-D-Arg-Phe-D-Ala-Trp-).

Yield; 3.0 mg (39.0%)

FAB-MS (M+H)⁺: 708 (theoretical value: 708)

Elution time: 26.5 min

Example 37

Synthesis of cyclo(-Phe-D-Arg(Tos)-Phe-D-Ala-Trp-)

Fmoc-D-Ala-Wang Resin (417 mg, 0.25 mmol) was condensed with the constitutive Fmoc-amino acids (1 mmol each) in the same manner as in Example 35-1), to obtain Fmoc-Trp-Phe-D-Arg(Tos)-Phe-D-Ala-Wang Resin. Next, the thus-obtained peptide-resin (562 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-Trp-Phe-D-Arg(Tos)-Phe-D-Ala-OH (yield: 245 mg, 96.7%). Then, the Fmoc-Trp-Phe-D-Arg(Tos)-Phe-D-Ala-OH (220 mg) was cyclized in the same manner as in Example 35-2) to obtain a crude cyclo(-Phe-D-Arg(Tos)-Phe-D-Ala-Trp-). 10 mg of this crude product was purified by HPLC to obtain cyclo(-Phe-D-Arg(Tos)-Phe-D-Ala-Trp-).

Yield: 0.7 mg (10.8%)

FAB-MS (M+H)$^+$: 862 (theoretical value: 862)

Elution time: 30.2 min

Example 38

Synthesis of cyclo(-pClPhe-D-Arg(Tos)-Phe-D-Ala-Trp-)

Fmoc-D-Ala-Wang Resin (417 mg, 0.25 mmol) was condensed with the constitutive Fmoc-amino acids (1 mmol each) in the same manner as in Example 35-1), to obtain Fmoc-Trp-pClPhe-D-Arg(Tos)-Phe-D-Ala-Wang Resin. Next, the thus-obtained peptide-resin (572 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-Trp-pClPhe-D-Arg(Tos)-Phe-D-Ala-OH (yield: 259 mg, 99.1%). Then, the Fmoc-Trp-pClPhe-D-Arg(Tos)-Phe-D-Ala-OH (179 mg) was cyclized in the same manner as in Example 35-2) to obtain a crude cyclo(-pClPhe-D-Arg(Tos)-Phe-D-Ala-Trp-). 10 mg of this crude product was purified by HPLC to obtain cyclo(-pClPhe-D-Arg(Tos)-Phe-D-Ala-Trp-).

Yield: 0.5 mg (7.5%)

FAB-MS (M+H)$^+$: 896 (theoretical value: 896)

Elution time: 31.4 min

Example 39

Synthesis of cyclo(-pClPhe-D-Arg-Phe-D-Ala-Trp-)

The crude cyclo(-pClPhe-D-Arg(Tos)-Phe-D-Ala-Trp-) (100 mg) as obtained in Example 38 was treated with HF in the presence of p-cresol (100 mg) and ethanedithiol (100 ml) for 2 hours, while cooling with ice. After HF was removed by distillation, ether was added to the residue and the precipitate formed was collected by filtration. This was purified by gel chromatography (G-25; 2 cm×80 cm). Finally, ⅕ of the product was further purified by HPLC using a column for partitioning purification of D-ODS-5-ST (2 cm×15 cm; produced by YMC Co.) to obtain cyclo(-pClPhe-D-Arg-Phe-D-Ala-Trp-).

Yield: 4.3 mg (21.5%)

FAB-MS (M+H)$^+$: 742 (theoretical value: 742)

Elution time: 27.8 min

Example 40

Synthesis of cyclo(-Phe-D-Arg(Tos)-Nal(2)-D-Ala-Trp-)

Fmoc-D-Ala-Wang Resin (417 mg, 0.25 mmol) was condensed with the constitutive Fmoc-amino acids (1 mmol each) in the same manner as in Example 35-1), to obtain Fmoc-Trp-Phe-D-Arg(Tos)-Nal(2)-D-Ala-Wang Resin. Next, the thus-obtained peptide-resin (576 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-Trp-Phe-D-Arg(Tos)-Nal(2)-D-Ala-OH (yield: 244 mg, 92.1%). Then, the Fmoc-Trp-Phe-D-Arg(Tos)-Nal(2)-D-Ala-OH (182 mg) was cyclized in the same manner as in Example 35-2) to obtain a crude cyclo(-Phe-D-Arg(Tos)-Nal(2)-D-Ala-Trp-). 10 mg of this crude product was purified by HPLC to obtain cyclo(-Phe-D-Arg(Tos)-Nal(2)-D-Ala-Trp-).

Yield: 1.1 mg (15.5%)

FAB-MS (M+H)$^+$: 912 (theoretical value: 912)

Elution time: 32.1 min

Example 41

Synthesis of cyclo(-Phe-D-Arg-Nal(2)-D-Ala-Trp-)

From the crude cyclo(-Phe-D-Arg(Tos)-Nal(2)-D-Ala-Trp-) (100 mg) as obtained in Example 40, obtained was cyclo(-Phe-D-Arg-Nal(2)-D-Ala-Trp-) in the same manner as in Example 39.

Yield: 7.8 mg (39.0%)

FAB-MS (M+H)$^+$: 758 (theoretical value: 758)

Elution time: 28.2 min

Example 42

Synthesis of cyclo(-Phe-Arg(Tos)-Phe-D-Ala-Trp-)

Fmoc-D-Ala-Wang Resin (417 mg, 0.25 mmol) was condensed with the constitutive Fmoc-amino acids (1 mmol each) in the same manner as in Example 35-1), to obtain Fmoc-Trp-Phe-Arg(Tos)-Phe-D-Ala-Wang Resin. Next, the thus-obtained peptide-resin (562 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-Trp-Phe-Arg(Tos)-Phe-D-Ala-OH (yield: 250 mg, 98.6%). Then, the Fmoc-Trp-Phe-Arg(Tos)-Phe-D-Ala-OH (172 mg) was cyclized in the same manner as in Example 35-2) to obtain a crude cyclo(-Phe-Arg(Tos)-Phe-D-Ala-Trp-). 15 mg of this crude product was purified by HPLC to obtain cyclo(-Phe-Arg(Tos)-Phe-D-Ala-Trp-).

Yield: 8.6 mg (71.5%)

FAB-MS (M+H)$^+$: 862 (theoretical value: 862)

Elution time: 30.2 min

Example 43

Synthesis of cyclo(-Phe-Arg-Phe-D-Ala-Trp-)

From the crude cyclo(-Phe-Arg(Tos)-Phe-D-Ala-Trp-) (100 mg) as obtained in Example 42, obtained was cyclo(-Phe-Arg-Phe-D-Ala-Trp-) in the same manner as in Example 39.

Yield: 12.6 mg (63.0%)

FAB-MS (M+H)$^+$: 708 (theoretical value: 708)

Elution time: 25.5 min

Example 44

Synthesis of cyclo(-Phe-D-Arg(Tos)-Phe-D-Leu-Trp-)

Fmoc-Phe-Wang Resin (610 mg, 0.25 mmol) was condensed with the constitutive Fmoc-amino acids (1 mmol each) in the same manner as in Example 35-1), to obtain Fmoc-D-Leu-Trp-Phe-D-Arg(Tos)-Phe-Wang Resin. Next, the thus-obtained peptide-resin (735 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-D-Leu-Trp-Phe-D-Arg (Tos)-Phe-OH (yield: 232 mg, 88.5%). Then, the Fmoc-D-Leu-Trp-Phe-D-Arg(Tos)-Phe-OH (229 mg) was cyclized in the same manner as in Example 35-2) to obtain a crude cyclo(-Phe-D-Arg(Tos)-Phe-D-Leu-Trp-). 10 mg of this crude product was purified by HPLC to obtain cyclo(-Phe-D-Arg(Tos)-Phe-D-Leu-Trp-).

Yield: 3.0 mg (29.4%)

FAB-MS (M+H)$^+$: 904 (theoretical value: 904)

Elution time: 32.5 min

Example 45

Synthesis of cyclo(-Phe-D-Arg(Tos)-Phe-D-Phe-Trp-)

Fmoc-Phe-Wang Resin (610 mg, 0.25 mmol) was condensed with the constitutive Fmoc-amino acids (1 mmol each) in the same manner as in Example 35-1), to obtain Fmoc-D-Phe-Trp-Phe-D-Arg(Tos)-Phe-Wang Resin. Next, the thus-obtained peptide-resin (742 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-D-Phe-Trp-Phe-D-Arg (Tos)-Phe-OH (yield: 252 mg, 93.0%). Then, the Fmoc-D-Phe-Trp-Phe-D-Arg(Tos)-Phe-OH (236 mg) was cyclized in the same manner as in Example 35-2) to obtain a crude cyclo(-Phe-D-Arg(Tos)-Phe-D-Phe-Trp-). ⅓ of this crude product was recrystallized from methanol-chloroform to obtain cyclo(-Phe-D-Arg(Tos)-Phe-D-Phe-Trp-).

Yield: 44.2 mg (70.6%)

FAB-MS (M+H)$^+$: 938 (theoretical value: 938)

Elution time: 32.7 min

Example 46

Synthesis of cyclo(-Phe-D-Arg(Tos)-Phe-D-Trp-Trp-)

Fmoc-Phe-Wang Resin (610 mg, 0.25 mmol) was condensed with the constitutive Fmoc-amino acids (1 mmol each) in the same manner as in Example 35-1), to obtain Fmoc-D-Trp-Trp-Phe-D-Arg(Tos)-Phe-Wang Resin. Next, the thus-obtained peptide-resin (750 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-D-Trp-Trp-Phe-D-Arg (Tos)-Phe-OH (yield: 268 mg, 95.7%). Then, the Fmoc-D-Trp-Trp-Phe-D-Arg(Tos)-Phe-OH (244 mg) was cyclized in the same manner as in Example 35-2) to obtain a crude cyclo(-Phe-D-Arg(Tos)-Phe-D-Trp-Trp-). ⅓ of this crude product was recrystallized from methanol-chloroform to obtain cyclo(-Phe-D-Arg(Tos)-Phe-D-Trp-Trp-).

Yield: 52.5 mg (83.0%)

FAB-MS (M+H)$^+$: 977 (theoretical value: 977)

Elution time: 32.6 min

Example 47

Synthesis of cyclo(-Phe-D-Arg(Tos)-pClPhe-D-Ala-Trp-)

Fmoc-D-Ala-Wang Resin (417 mg, 0.25 mmol) was condensed with the constitutive Fmoc-amino acids (1 mmol each) in the same manner as in Example 35-1), to obtain Fmoc-Trp-Phe-D-Arg(Tos)-pClPhe-D-Ala-Wang Resin. Next, the thus-obtained peptide-resin (565 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-Trp-Phe-D-Arg (Tos)-pClPhe-D-Ala-OH (yield: 235 mg, 89.9%). Then, the Fmoc-Trp-Phe-D-Arg(Tos)-pClPhe-D-Ala-OH (227 mg) was cyclized in the same manner as in Example 35-2) to obtain a crude cyclo(-Phe-D-Arg(Tos)-pClPhe-D-Ala-Trp-). 15 mg of this crude product was purified by HPLC to obtain cyclo(-Phe-D-Arg(Tos)-pClPhe-D-Ala-Trp-).

Yield: 7.8 mg (50.5%)

FAB-MS (M+H)$^+$: 896 (theoretical value: 896)

Elution time: 31.3 min

Example 48

Synthesis of cyclo(-Phg-D-Arg(Tos)-Phe-D-Ala-Trp-)

Fmoc-Phe-Wang Resin (610 mg, 0.25 mmol) was condensed with the constitutive Fmoc-amino acids (1 mmol each) in the same manner as in Example 35-1), to obtain Fmoc-D-Ala-Trp-Phg-D-Arg(Tos)-Phe-Wang Resin. Next, the thus-obtained peptide-resin (725 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-D-Ala-Trp-Phg-D-Arg (Tos)-Phe-OH (yield: 234 mg, 93.5%). Then, the Fmoc-D-Ala-Trp-Phg-D-Arg(Tos)-Phe-OH (217 mg) was cyclized in the same manner as in Example 35-2) to obtain a crude cyclo(-Phg-D-Arg(Tos)-Phe-D-Ala-Trp-). 10 mg of this crude product was purified by HPLC to obtain cyclo(-Phg-D-Arg(Tos)-Phe-D-Ala-Trp-).

Yield: 2.4 mg (28.3%)

FAB-MS (M+H)$^+$: 848 (theoretical value: 848)

Elution time: 28.2 min

Example 49

Synthesis of cyclo(-pFPhe-D-Arg(Tos)-Phe-D-Ala-Trp-)

Fmoc-D-Ala-Wang Resin (417 mg, 0.25 mmol) was condensed with the constitutive Fmoc-amino acids (1 mmol each) in the same manner as in Example 35-1), to obtain Fmoc-Trp-pFPhe-D-Arg(Tos)-Phe-D-Ala-Wang Resin. Next, the thus-obtained peptide-resin (565 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-Trp-pFPhe-D-Arg (Tos)-Phe-D-Ala-OH (yield: 254 mg, 98.6%). Then, the Fmoc-Trp-pFPhe-D-Arg(Tos)-Phe-D-Ala-OH (201 mg) was cyclized in the same manner as in Example 35-2) to obtain a crude cyclo(-pFPhe-D-Arg(Tos)-Phe-D-Ala-Trp-). 15 mg of this crude product was purified by HPLC to obtain cyclo(-pFPhe-D-Arg(Tos)-Phe-D-Ala-Trp-).

Yield: 6.6 mg (58.8%)

FAB-MS (M+H)$^+$: 880 (theoretical value: 880)

Elution time: 30.6 min

Example 50

Synthesis of cyclo(-Phe-D-Arg(Tos)-pFPhe-D-Ala-Trp-)

Fmoc-D-Ala-Wang Resin (417 mg, 0.25 mmol) was condensed with the constitutive Fmoc-amino acids (1 mmol each) in the same manner as in Example 35-2), to obtain Fmoc-Trp-Phe-D-Arg(Tos)-pFPhe-D-Ala-Wang Resin. Next, the thus-obtained peptide-resin (565 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-Trp-Phe-D-Arg(Tos)-pFPhe-D-Ala-OH (yield: 228 mg, 88.5%). Then, the Fmoc-Trp-Phe-D-Arg(Tos)-pFPhe-D-Ala-OH (201 mg) was cyclized in the same manner as in Example 35-2) to obtain a crude cyclo(-Phe-D-Arg(Tos)-pFPhe-D-Ala-Trp-). 15 mg of this crude product was purified by HPLC to obtain cyclo(-Phe-D-Arg(Tos)-pFPhe-D-Ala-Trp-).

Yield: 7.2 mg (65.6%)

FAB-MS (M+H)$^+$: 880 (theoretical value: 880)

Elution time: 30.6 min

Example 51

Synthesis of cyclo(-Ala-D-Arg(Tos)-Phe-D-Ala-Trp-)

Fmoc-D-Ala-Wang Resin (417 mg, 0.25 mmol) was condensed with the constitutive Fmoc-amino acids (1 mmol each) in the same manner as in Example 35-1), to obtain Fmoc-Trp-Ala-D-Arg(Tos)-Phe-D-Ala-Wang Resin. Next, the thus-obtained peptide-resin (547 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-Trp-Ala-D-Arg(Tos)-Phe-D-Ala-OH (yield: 205 mg, 86.9%). Then, the Fmoc-Trp-Ala-D-Arg(Tos)-Phe-D-Ala-OH (185 mg) was cyclized in the same manner as in Example 35-2) to obtain a crude cyclo(-Ala-D-Arg(Tos)-Phe-D-Ala-Trp-). 10 mg of this crude product was purified by HPLC to obtain cyclo(-Ala-D-Arg(Tos)-Phe-D-Ala-Trp-).

Yield: 1.7 mg (21.8%)

FAB-MS (M+H)$^+$: 786 (theoretical value: 786)

Elution time: 27.0 min

Example 52

Synthesis of cyclo(-Phg-D-Arg(Tos)-Phe-D-Ser-Trp-)

Fmoc-Phe-Wang Resin (610 mg, 0.25 mmol) was condensed with the constitutive Fmoc-amino acids (1 mmol each) in the same manner as in Example 35-1), to obtain Fmoc-D-Ser-Trp-Phg-D-Arg(Tos)-Phe-Wang Resin. Next, the thus-obtained peptide-resin (742 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-D-Ser-Trp-Phg-D-Arg(Tos)-Phe-OH (yield: 246 mg, 96.9%). Then, the Fmoc-D-Ser-Trp-Phg-D-Arg(Tos)-Phe-OH (199 mg) was cyclized in the same manner as in Example 35) to obtain a crude cyclo(-Phg-D-Arg(Tos)-Phe-D-Ser-Trp-). 10 mg of this crude product was purified by HPLC to obtain cyclo(-Phg-D-Arg(Tos)-Phe-D-Ser-Trp-).

Yield: 1.2 mg (15.7%)

FAB-MS (M+H)$^+$: 864 (theoretical value: 864)

Elution time: 27.3 min

Example 53

Synthesis of cyclo(-Phg-D-Arg(Tos)-Phe-D-Ala-Phe-)

Fmoc-D-Ala-Wang Resin (417 mg, 0.25 mmol) was condensed with the constitutive Fmoc-amino acids (1 mmol each) in the same manner as in Example 35-1), to obtain Fmoc-Phe-Phg-D-Arg(Tos)-Phe-D-Ala-Wang Resin. Next, the thus-obtained peptide-resin (557 mg) was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give Fmoc-Phe-Phg-D-Arg(Tos)-Phe-D-Ala-OH (yield: 236 mg, 97.8%). Then, the Fmoc-Phe-Phg-D-Arg(Tos)-Phe-D-Ala-OH (191 mg) was cyclized in the same manner as in Example 35-2) to obtain a crude cyclo(-Phg-D-Arg(Tos)-Phe-D-Ala-Phe-). 10 mg of this crude product was purified by HPLC to obtain cyclo(-Phg-D-Arg(Tos)-Phe-D-Ala-Phe-).

Yield: 0.8 mg (13.1%)

FAB-MS (M+H)$^+$: 809 (theoretical value: 809)

Elution time: 29.4 min

Example 54

Synthesis of cyclo(-Thg(2)-D-Arg(Tos)-Phe-D-Ala-Trp-)

Fmoc-Trp-Wang Resin (472 mg, 0.25 mmol) was condensed with the constitutive Fmoc-amino acids (1 mmol each) and Boc-Thg(2) (1 mmol) in the same manner as in Example 35-1), to obtain Boc-Thg(2)-D-Arg(Tos)-Phe-D-Ala-Trp-Wang Resin. Next, the thus-obtained peptide-resin was shaken in 50%-TFA/DCM (20 ml) (containing 2.5%-ethanedithiol) for 30 minutes. Then, the resin removed from the peptide was taken out by filtration, and the mother filtrate was concentrated. Ether was added to the resulting concentrate, which was thus solidified to give TFA.H-Thg(2)-D-Arg(Tos)-Phe-D-Ala-Trp-OH (yield: 181 mg, 72.4%). Then, this was cyclized in the same manner as in Example 35-2) to obtain a crude cyclo(-Thg(2)-D-Arg(Tos)-Phe-D-Ala-Trp-). ⅓ of this crude product was purified by HPLC to obtain cyclo(-Thg(2)-D-Arg(Tos)-Phe-D-Ala-Trp-).

Yield: 2.3 mg (13.8%)

FAB-MS (M+H)$^+$: 854 (theoretical value: 854)

Elution time: 29.0 min

Example 55

Synthesis of cyclo(-Phg-D-Arg-Phe-D-Ala-Trp-)

The crude cyclo(-Phg-D-Arg(Tos)-Phe-D-Ala-Trp-) (100 mg) as obtained in Example 48 was treated with HF in the presence of p-cresol (75 mg) and ethanedithiol (50 ml) for 2 hours while cooling with ice. After HF was removed by distillation, ether was added to the residue and the precipitate formed was collected by filtration. This was purified by gel chromatography (G-25; 2 cm×80 cm). Finally, 20 g of the product was further purified by HPLC using a column for partitioning purification of D-ODS-5-ST (2 cm×15 cm; produced by YMC Co.) to obtain cyclo(-Phg-D-Arg-Phe-D-Ala-Trp-).

Yield: 3.5 mg (17.5%)
FAB-MS (M+H)$^+$: 695 (theoretical value: 695)
Elution time: 25.4 min Example 56

Synthesis of cyclo(-pClPhe-D-Arg(Tos)-Nal(2)-D-Ala-Trp-)

1) Synthesis of Boc-D-Ala-oxime resin:

Oxime resin (1.86 g; substitution of 0.65 mmol/g) was swollen in DCM (10 ml), and Boc-D-Ala (265 mg) and DCC (289 mg) were added thereto and shaken for 24 hours. After having been washed with DCM and MeOH and then dried, obtained was Boc-D-Ala-oxime resin.

Yield: 1.10 g (substitution of 0.59 mmol/g) (92.9%)

2) Synthesis of cyclo(-pClPhe-D-Arg(Tos)-Nal(2)-D-Ala-Trp-):

Boc-D-Ala-oxime resin (1.08 g, 0.65 mmol) as obtained in Example 56-1) was condensed in order with the constitutive Boc-Amino acids (1.95 mmol each), using PyBOP (1.95 mmol) and removing the Boc groups by the use of 25%-TFA-DCM, whereby the peptide chain was stepwise extended to give Boc-Trp-pClPhe-D-Arg(Tos)-Nal(2)-D-Ala-oxime resin. Next, the thus-obtained peptide-resin was treated with 25%-TFA/DCM, washed with DCM and isopropanol and swollen in DMF, and diisopropylethylamine (227 ml) and acetic acid (75 ml) were added thereto and shaken for 18 hours. The resin separated was removed by filtration, and the resulting filtrate was concentrated under reduced pressure. Water was added to the concentrate, and the precipitate thus formed was collected by filtration. Thus, obtained was cyclo(-pClPhe-D-Arg(Tos)-Nal(2)-D-Ala-Trp-).

Yield: 571 mg (92.8%)
FAB-MS (M+H)$^+$: 946 (theoretical value: 946)
Elution time: 33.8 min Example 57

Synthesis of cyclo(-pClPhe-D-Arg-Nal(2)-D-Ala-Trp-)

cyclo(-pClPhe-D-Arg(Tos)-Nal(2)-D-Ala-Trp-) (200 mg) as obtained in Example 56-2 was treated with HF in the presence of p-cresol (150 mg) and ethanedithiol (100 ml) for 2 hours while cooling with ice. After HF was removed by distillation, ether was added to the residue and the precipitate formed was collected by filtration. This was purified by using G15. Finally, a part of the product was further purified by HPLC using a column for partitioning purification of D-ODS-5-ST (2 cm×15 cm; produced by YMC Co.) to obtain cyclo(-pClPhe-D-Arg-Nal(2)-D-Ala-Trp-).

Yield: 5.9 mg (39%)
FAB-MS (M+H)$^+$: 792 (theoretical value: 792)
Elution time: 30.0 min Example 58

Synthesis of cyclo(-pClPhe-Arg(Tos)-Nal(2)-D-Ala-Trp-)

Boc-D-Ala-oxime resin (1.10 g, 0.71 mmol) as obtained in Example 56-1) was condensed with the constitutive Boc-amino acids (2.1 mmol each) in the same manner as in Example 56-2), to obtain cyclo(-pClPhe-Arg(Tos)-Nal(2)-D-Ala-Trp-).

Yield: 397 mg (59.1%)
FAB-MS (M+H)$^+$: 946 (theoretical value: 946)
Elution time: 33.1 min Example 59

Synthesis of cyclo(-pClPhe-Arg-Nal(2)-D-Ala-Trp-)

Cyclo(-pClPhe-Arg(Tos)-Nal(2)-D-Ala-Trp-) (200 mg) as obtained in Example 58 was processed in the same manner as in Example 57, to obtain cyclo(-pClPhe-Arg-Nal(2)-D-Ala-Trp-).

Yield: 5.5 mg (37%)
FAB-MS (M+H)$^+$: 792 (theoretical value: 792)
Elution time: 29.0 min Reference Example 1

Synthesis of cyclo(-Tyr-D-Trp-Leu-Arg-Trp-Pro-)

1) Synthesis of Boc-Pro-Tyr(Br-Z)-D-Trp-Leu-Arg(Tos)-OPac:

Boc-Tyr(Br-Z)-D-Trp-Leu-Arg(Tos)OPac (917 mg) as obtained in Example 2-5) was treated with 10 N—HCl/dioxane (10 ml) to thereby remove its Boc group, and diisopropylethylamine (0.28 ml) and Boc-Pro-ONB (prepared from Boc-Pro-OH (178 mg), HONB (162 mg) and DCC (186 mg)) were added thereto to obtain the intended product.

Yield: 850 mg (85.9%)
$R_f$: 0.24
m.p.: 118.0–121.0 C.
Elementary analysis: as $C_{65}H_{76}N_9O_{14}BrS \cdot 0.25\ H_2O$. Calculated: C, 58.97; H, 5.79; N, 9.46. Measured: C, 58.99; H, 5.81; N, 9.35.

2) Synthesis of Boc-Trp-Pro-Tyr(Br-Z)-D-Trp-Leu-Arg(Tos)-OPac:

Boc-Pro-Tyr(Br-Z)-D-Trp-Leu-Arg(Tos)-OPac (850 mg) was treated with 10 N—HCl/dioxane (10 ml) to thereby remove its Boc group, and diisopropylethylamine (0.25 ml) and Boc-Trp-ONB (prepared from Boc-Trp-OH (178 mg), HONB (162 mg) and DCC (186 mg)) were added thereto to obtain the intended product.

Yield: 800 mg (82.8%)
$R_f$: 0.36
m.p.: 132.0–134.0° C.
Elementary analysis: as $C_{76}H_{86}N_{11}O_{15}BrS \cdot 0.5\ H_2O$. Calculated: C, 60.27; H, 5.72; N, 10.17. Measured: C, 60.00; H, 5.89; N, 9.98.

3) Synthesis of cyclo(-Tyr-D-Trp-Leu-Arg-Trp-Pro-):

In the same manner as in Example 2-8), Boc-Trp-Pro-Tyr(Br-Z)-D-Trp-Leu-Arg(Tos)-OPac (500 mg) was dissolved in 90%-acetic acid (10 ml), and Zn (1.09 g) was added thereto and stirred for 30 minutes. Zn was removed, then the solvent was removed by distillation, and AcOEt (100 ml) and water (100 ml) were added to the residue. The aqueous layer was separated and washed with AcOEt (100 ml). The AcOEt layers were combined, washed with saturated saline solution (200 ml), dried with anhydrous sodium sulfate and concentrated, to obtain an oily product. Diethyl ether was added thereto to obtain a colorless precipitate. This was dissolved in chloroform (20 ml), and HONB (119 mg) and DCC (137 mg) were added thereto while cooling with ice and then stirred at room temperature for 2 hours. The DCU formed was removed, and the solvent was removed by distillation. Next, 10 N—HCl/dioxane (15 ml) was added to the residue and stirred for 30 minutes while cooling with ice. The solvent was removed by distillation, and the residue was dried in the presence of sodium hydroxide. This was dissolved in DMF (30 ml), then dropwise added to a DMF (300 ml) solution of diisopropylethylamine (0.60 ml) and directly stirred overnight. The solvent was removed by distillation, the residue was washed for a total of two times with AcOEt (100 ml), and a pale yellow powder was obtained. The thus-obtained powder (100 mg) was dissolved in HF (5 ml) in the presence of p-cresol (100 mg) and 1,4-butane-dithiol (0.1 ml) and stirred for 1 hour. HF was removed by distillation, then diethyl ether was added to the residue, and the precipitate formed was taken out by filtration. This was dissolved in a small amount of acetic acid, diluted with water and freeze-dried. Finally, this was purified by partitioning liquid chromatography using a column of YMC ODS-25-20 (2 cm×25 cm; produced by YMC Co.), and the intended product was obtained.

Yield: 45.9 mg (15.3%)

Amino acid analysis (after hydrolyzed in 6 N—HCl at 110° C. for 24 hours) (Parenthesized are the theoretical data.): Leu 1.00 (1); Tyr 0.90 (1); Pro 1.11 (1); Arg 0.94 (1).

FAB-MS (M+H)$^+$: 902 (theoretical value: 902)

Reference Example 2

Preparation of Fraction of Cell Membranes of CHO Cells (Collected from Chinese Hamster Ovary) Containing Human LH-RH Receptor Human LH-RH receptor-expressing CHO cells ($10^9$ cells) were floated in a phosphate buffer saline containing 5 mM EDTA (PBS-EDTA) and subjected to centrifugation at 100×g for 5 minutes. 10 ml of a cell homogenate buffer (10 mM NaHCO$_3$, 5 mM EDTA, pH 7.5) was added to the resulting cell pellets, and the resulting mixture was then homogenized in a polytron homogenizer. This was thereafter centrifuged at 400×g for 15 minutes, and the resulting supernatant was collected in an ultra-centrifuger and again centrifuged at 100,000×g for 1 hour to obtain a precipitate of the cell membrane fraction. This precipitate was suspended in 2 ml of an assay buffer and centrifuged at 100,000×g for 1 hour. The cell membrane fraction thus collected as a precipitate was again suspended in 20 ml of an assay buffer, put into plural vials and stored at −80° C. These were individually thawed before use.

Test Example 1

Determination of Percentage of Inhibition of Bonding of $^{125}$I-Leuprorelin to Human LH-RH Receptor The human LH-RH receptor-expressing CHO cell membrane fraction as prepared in Reference Example 2 was diluted with an assay buffer to have a concentration of 200 μg/ml and put into plural tubes at 188 μl/tube. Where the human LH-RH receptor-expressing CHO cell membrane fraction was used, 2 μl of a solution of the test compound (2 mM) as dissolved in 60%-DMSO and 10 μl of $^{125}$I-leuprorelin (38 nM) were added to the dilution of the fraction. In order to measure the maximum amount of the $^{125}$I-leuprorelin as bonded to the receptor, a reaction system comprising 2 μl of 60%-DMSO and 10 μl of $^{125}$I-leuprorelin (38 nM) was prepared. In order to measure the amount of $^{125}$I-leuprorelin as non-specifically bonded to the receptor, a reaction system comprising 2 μl of leuprorelin (100 μM) as dissolved in 60%-DMSO and 10 μl of $^{125}$I-leuprorelin (38 nM) was prepared.

Each system of the present invention comprising the human LH-RH receptor-expressing CHO cell membrane fraction was reacted at 25° C. for 60 minutes. After the reaction, the reaction mixture was filtered under suction through a polyethyleneimine-treated Wattman glass filter (GF-F). After the filtration, the radioactivity of $^{125}$I-leuprorelin in the residue remained on the filter paper was measured using a g-counter.

From the data measured, a value of [(TB-SB)/(TB-NSB)]×100 (where SB is the radioactivity of the test system to which the test compound had been added; TB is the radioactivity of the maximum bonding system; and NSB is the radioactivity of the non-specific bonding system) was calculated, which indicates the bonding-inhibition percentage (%) of the compound tested. The bonding-inhibition percentage of each test compound was obtained by varying the concentration the compound being tested, from which the concentration of the test compound that showed the bonding-inhibition of 50% (IC$_{50}$) was calculated by Hill plotting. The results obtained are shown in [Table 1].

TABLE 1

IC$_{50}$ (μM) in Receptor Assay

| Compound of Example Tested | IC$_{50}$ (μM) |
|---|---|
| 1 | 0.9 |
| 19 | 1.0 |
| 20 | 0.1 |
| 21 | 0.4 |
| 23 | 0.9 |
| 31 | 0.2 |
| 35 | 0.4 |
| 36 | 0.9 |
| 37 | 0.3 |
| 43 | 1.0 |
| 48 | 0.07 |
| 51 | 0.2 |
| 53 | 0.1 |
| 54 | 0.3 |
| 55 | 0.2 |
| Compound of Reference Example Tested | |
| 1 | 10 |

Preparation Example 1

50 mg of the compound as obtained in Example 48 was dissolved in 50 ml of Japanese pharmacopoeial, distilled water for injection, and Japanese pharmacopoeial, distilled water for injection was added thereto to make 100 ml. The resulting solution was filtered under a germ-free condition, and the filtrate of 1 ml each was filled in vials for injection, freeze-dried and sealed therein also under a germ-free condition.

Preparation Example 2

500mg of the compound as obtained in Example 48 was dissolved in 50 ml of Japanese pharmacopoeial, distilled water for injection, and Japanese pharmacopoeial, distilled water for injection was added thereto to make 100 ml. The resulting solution was filtered under a germ-free condition, and the filtrate of 1 ml each was filled in vials for injection, freeze-dried and sealed therein also under a germ-free condition.

Preparation Example 3

0.5 g of a mono-hydrochloride of the compound as obtained in Example 20 was dissolved in 50 ml of Japanese pharmacopoeial, distilled water for injection, and Japanese pharmacopoeial, distilled water for injection was added thereto to make 100 ml. The resulting solution was filtered under a germ-free condition, and the filtrate of 1 ml each was filled in vials for injection, freeze-dried and sealed therein also under a germ-free condition.

Preparation Example 4

1.5 g of a mono-hydrochloride of the compound as obtained in Example 31 was dissolved in 50 ml of Japanese pharmacopoeial, distilled water for injection, and Japanese pharmacopoeial, distilled water for injection was added thereto to make 100 ml. The resulting solution was filtered under a germ-free condition, and the filtrate of 1 ml each was filled in vials for injection, freeze-dried and sealed therein also under a germ-free condition.

2. A method for pregnancy control in a mammal, comprising administering an effective amount of a cyclic pentapeptide or salt thereof of claim 1, to the mammal.

3. A method for menstrual cycle control in a mammal, comprising administering an effective amount of a cyclic pentapeptide or salt thereof according to claim 1, to the mammal.

4. A method for contraception in a mammal, comprising administering an effective amount of a cyclic pentapeptide according to claim 1, to the mammal.

5. A method for antagonizing the luteinizing hormone-releasing hormone (LH-RH) receptor in a mammal in need thereof, comprising administering a therapeutically effective amount of a cyclic pentapeptide of claim 1 to the mammal.

What is claimed is:

1. A cyclic pentapeptide of the formula:

cyclo(-$A_1'$-$A_2'$-$A_3'$-$A_4'$-$A_5'$-)

wherein $A_1'$ is Arg, Arg(Tos) or Arg(Mtr); and $A_2'$, $A_3'$, $A_4'$, and $A_5'$ are defined as follows:

when $A_2'$ is Lys, Lys(Isopropyl), Lys($SO_2$Nap(1)), Lys($SO_2$Nap(2)), Lys(COPh), Lys($COCH_2$Ph), Lys(CO—($CH_2$)$_3$-Ph), Lys(CO—($CH_2$)$_5$-Ph), Lys(Ac), Lys(CO-Nap(1)), Lys(Nic), or Trp then $A_3'$ is Tyr or Trp, $A_4'$ is Tyr or Trp, and $A_5'$ is Leu;

when $A_2'$ is Glu, Glu(NH—$CH_2$—$CH_2$-Ph), Glu(NH—$CH_2$-Ph), Glu(NH—CH-$Ph_2$), Glu(NH—$CH_2$-Nap(1)), Glu(Php), Glu(Bzlp), Glu((2)-Pyp), Glu(2-MeOPhp), or Glu(4-MeOPhp), then $A_3'$, is Lys, Lys(Isopropyl), Lys($SO_2$Nap(1)), Lys($SO_2$Nap(2)), Lys(COPh), Lys($COCH_2$Ph), Lys(CO—($CH_2$)$_3$-Ph), Lys(CO—($CH_2$)$_5$-Ph), Lys(Ac), Lys(CO-Nap(1)), Lys(Nic), or Tyr, $A_4'$ is Trp, and $A_5'$ is Leu; or when $A_2'$ is Phe, (p-Cl)Phe or (p-F)Phe, then $A_3'$ is Ala, $A_4'$ is Trp and $A_5'$ is Phe, (p-Cl)Phe, (p-F)Phe, or Phg;

wherein $A_1'$, $A_3'$ and $A_5'$ have an L-configuration, and $A_2'$ and $A_4'$ have a D-configuration; or $A_2'$, $A_4'$ and $A_5'$ have an L-configuration, and $A_1'$ and $A_3'$ has a D-configuration; or a salt thereof.

6. The method as claimed in claim 5, wherein the administration is for treating sex hormone-dependent disorders.

7. The method as claimed in claim 6, wherein the sex hormone-dependent disorders are sex hormone-dependent cancers.

8. The method as claimed in claim 7, wherein the sex hormone-dependent cancers are prostatic cancer, uterine cancer, mammary cancer or pituitary tumor.

9. The method as claimed in claim 6, wherein the sex hormone-dependent disorders are prostatomegaly, endometriosis, hysteromyoma or puberty precox.

10. A cyclic pentapeptide of the formula:
cyclo(-Arg-D-Lys($SO_2$Nap(1))-Tyr-D-Trp-Leu-),
cyclo(-Arg-D-Lys(COPh)-Tyr-D-Trp-Leu-),
cyclo(-Arg-D-Lys($SO_2$Nap(2))-Trp-D-Trp-Leu-),
cyclo(-Arg-D-Trp-Tyr-D-Trp-Leu-),
cyclo(-Arg-D-Glu(Php)-Tyr-D-Trp-Leu-),
cyclo(-Arg-D-Lys(CO($CH_2$)$_3$Ph)-Tyr-D-Trp-Leu-),
cyclo(-Arg-D-Lys(CO($CH_2$)$_5$Ph)-Tyr-D-Trp-Leu-),
cyclo(-Arg-D-Glu(NH($CH_2$)$_2$Ph)-Lys(COPh)-D-Trp-Leu-),
cyclo(-D-Arg(Mtr)-Phe-D-Ala-Trp-Phe-), or
cyclo(-D-Arg(Tos)-Phe-D-Ala-Trp-Phg-);
or a salt thereof.

11. A method for antagonizing the luteinizing hormone-releasing hormone (LH-RH) receptor in a mammal in need thereof, comprising administering a therapeutically effective amount of a cyclic pentapeptide of claim 10, to the mammal.

12. The method as claimed in claim 11, wherein the administration is for treating sex hormone-dependent disorders.

13. The method as claimed in claim 12, wherein the sex hormone-dependent disorders are sex hormone-dependent cancers.

14. The method as claimed in claim 13, wherein the sex hormone-dependent cancers are prostatic cancer, uterine cancer, mammary cancer or pituitary tumor.

15. The method as claimed in claim 12, wherein the sex hormone-dependent disorders are prostatomegaly, endometriosis, hysteromyoma or puberty precox.

16. A method for pregnancy control in a mammal, comprising administering an effective amount of a cyclic pentapeptide or salt thereof of claim 10, to the mammal.

17. A method for menstrual cycle control in a mammal, comprising administering an effective amount of a cyclic pentapeptide or salt thereof according to claim 10, to the mammal.

18. A method for contraception in a mammal, comprising administering an effective amount of a cyclic pentapeptide according to claim 10, to the mammal.

19. A method for antagonizing the luteinizing hormone-releasing hormone (LH-RH) receptor in a mammal in need thereof, comprising a cyclic pentapeptide selected from the group consisting of cyclo(-Arg-D-Lys($SO_2$Nap(1))-Tyr-D-Trp-Leu)

cyclo(-Arg-D-Lys(CO($CH_2$)$_3$Ph)-Tyr-D-Trp-Leu)

cyclo(-Arg-D-Glu(NH($CH_2$)$_2$Ph)-Lys(CoPh)-D-Trp-Leu)

cyclo(-D-Arg-Phe-D-Ala-Trp-Phg-), and salts thereof.

* * * * *

```
                              SEQUENCE LISTING (1) GENERAL INFORMATION:

(iii) NUMBER OF SEQUENCES:  1

(2) INFORMATION FOR SEQ ID NO:1:

(i) SEQUENCE CHARACTERISTICS:
        (A) LENGTH:  5 amino acids
        (B) TYPE:  amino acid
        (C) STRANDEDNESS:  single
        (D) TOPOLOGY:  circular (ii) MOLECULE TYPE:

(ix) FEATURE:
        (A) NAME/KEY:
        (B) LOCATION:
        (C) IDENTIFICATION METHOD:
        (D) OTHER INFORMATION:   /note= "Xaa independently represent any
            alpha-amino acid residue or derivative thereof"

(xi) SEQUENCE DESCRIPTION: SEQ ID NO:1:

Xaa Xaa Xaa Xaa Xaa
 1               5
```